(12) United States Patent
Kizer et al.

(10) Patent No.: US 8,652,507 B2
(45) Date of Patent: *Feb. 18, 2014

(54) JUVENILE CARTILAGE COMPOSITION

(75) Inventors: Neil Kizer, Crestwood, MO (US);
Robert Spiro, Half Moon Bay, CA (US);
Jian Yao, Austin, TX (US); Cheryl Renee Blanchard, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 43 days.

This patent is subject to a terminal disclaimer.

(21) Appl. No.: 12/976,711

(22) Filed: Dec. 22, 2010

(65) Prior Publication Data
US 2012/0009224 A1  Jan. 12, 2012

Related U.S. Application Data

(63) Continuation of application No. 12/861,404, filed on Aug. 23, 2010, which is a continuation of application No. 11/010,779, filed on Dec. 13, 2004, now Pat. No. 7,824,711.

(60) Provisional application No. 60/528,865, filed on Dec. 11, 2003.

(51) Int. Cl.
*A61F 2/02* (2006.01)

(52) U.S. Cl.
USPC .......................................... 424/426

(58) Field of Classification Search
None
See application file for complete search history.

(56) References Cited

U.S. PATENT DOCUMENTS

| | | |
|---|---|---|
| 1,347,622 A | 7/1920 | Deininger |
| 2,533,004 A | 12/1950 | Ferry et al. |
| 2,621,145 A | 12/1952 | Sano |
| 3,400,199 A | 9/1968 | Balassa |
| 3,474,146 A | 10/1969 | Baker et al. |
| 3,476,855 A | 11/1969 | Balassa |
| 3,478,146 A | 11/1969 | Balassa |
| 3,772,432 A | 11/1973 | Balassal |
| RE28,093 E | 7/1974 | Balassa |
| 3,966,908 A | 6/1976 | Balassa |
| 4,440,680 A | 4/1984 | Cioca |
| 4,453,939 A | 6/1984 | Zimmerman et al. |
| 4,479,271 A | 10/1984 | Bolesky et al. |
| 4,522,096 A | 6/1985 | Niven, Jr. |
| 4,566,138 A | 1/1986 | Lewis et al. |
| 4,587,766 A | 5/1986 | Miyatake et al. |

(Continued)

FOREIGN PATENT DOCUMENTS

| | | |
|---|---|---|
| AU | 199871003 B2 | 10/1998 |
| AU | 2006282754 A2 | 3/2007 |

(Continued)

OTHER PUBLICATIONS

Langer, F. and Gross, A.E., Immunogenicity of Allograft Articular Cartilage, JBJS, 1974, pp. 297-304, vol. 56-A, No. 2.

(Continued)

*Primary Examiner* — Carlos Azpuru
(74) *Attorney, Agent, or Firm* — Schwegman, Lundberg & Woessner P.A.

(57) ABSTRACT

The present invention is directed to compositions having at least one neocartilage particle, juvenile cartilage particle or a combination thereof and a matrix, and methods and devices that include the compositions.

17 Claims, 3 Drawing Sheets

Chondral Defect – Uniform Distribution

(56) References Cited

U.S. PATENT DOCUMENTS

| | | |
|---|---|---|
| 4,609,551 A | 9/1986 | Caplan et al. |
| 4,627,879 A | 12/1986 | Rose et al. |
| 4,640,834 A | 2/1987 | Eibl et al. |
| 4,641,651 A | 2/1987 | Card |
| 4,642,120 A | 2/1987 | Nevo et al. |
| 4,656,137 A | 4/1987 | Balassa |
| 4,660,755 A | 4/1987 | Farling |
| 4,714,457 A | 12/1987 | Alterbaum |
| 4,773,418 A | 9/1988 | Hettich |
| 4,818,633 A | 4/1989 | Dinwoodie et al. |
| 4,846,835 A | 7/1989 | Grande |
| 4,851,354 A | 7/1989 | Winston et al. |
| 4,863,474 A | 9/1989 | Brown et al. |
| 4,863,475 A | 9/1989 | Andersen et al. |
| 4,904,259 A | 2/1990 | Itay |
| 4,911,720 A | 3/1990 | Collier |
| 4,928,603 A | 5/1990 | Rose et al. |
| 4,952,403 A | 8/1990 | Vallee et al. |
| 4,963,489 A | 10/1990 | Naughton et al. |
| 4,997,444 A | 3/1991 | Farling |
| 4,997,445 A | 3/1991 | Hodorek |
| 5,002,071 A | 3/1991 | Harrell |
| 5,002,582 A | 3/1991 | Guire et al. |
| 5,013,324 A | 5/1991 | Zolman et al. |
| 5,018,285 A | 5/1991 | Zolman et al. |
| 5,030,215 A | 7/1991 | Morse et al. |
| 5,032,508 A | 7/1991 | Naughton et al. |
| 5,041,138 A | 8/1991 | Vacanti et al. |
| 5,053,050 A | 10/1991 | Itay |
| 5,067,963 A | 11/1991 | Khouri et al. |
| 5,067,964 A | 11/1991 | Richmond et al. |
| 5,069,881 A | 12/1991 | Clarkin |
| 5,080,674 A | 1/1992 | Jacobs et al. |
| 5,092,887 A | 3/1992 | Gendler |
| 5,130,418 A | 7/1992 | Thompson |
| 5,139,527 A | 8/1992 | Redl et al. |
| 5,189,148 A | 2/1993 | Akiyama et al. |
| 5,198,308 A | 3/1993 | Shetty et al. |
| 5,206,023 A | 4/1993 | Hunziker |
| 5,217,954 A | 6/1993 | Foster et al. |
| 5,219,363 A | 6/1993 | Crowninshield et al. |
| 5,226,914 A | 7/1993 | Caplan et al. |
| 5,236,457 A | 8/1993 | Devanathan |
| 5,254,471 A | 10/1993 | Mori et al. |
| 5,269,785 A | 12/1993 | Bonutti |
| 5,270,300 A | 12/1993 | Hunziker |
| 5,281,422 A | 1/1994 | Badylak et al. |
| 5,282,861 A | 2/1994 | Kaplan |
| 5,290,552 A | 3/1994 | Sierra et al. |
| 5,290,558 A | 3/1994 | O'Leary et al. |
| 5,312,417 A | 5/1994 | Wilk |
| 5,323,954 A | 6/1994 | Shetty et al. |
| 5,326,357 A | 7/1994 | Kandel |
| 5,345,927 A | 9/1994 | Bonutti |
| 5,356,629 A | 10/1994 | Sander et al. |
| 5,368,858 A | 11/1994 | Hunziker |
| 5,372,821 A | 12/1994 | Badylak et al. |
| 5,387,243 A | 2/1995 | Devanathan |
| 5,403,317 A | 4/1995 | Bonutti |
| 5,405,607 A | 4/1995 | Epstein |
| 5,410,016 A | 4/1995 | Hubbell et al. |
| 5,443,454 A | 8/1995 | Tanabe et al. |
| 5,443,510 A | 8/1995 | Shetty |
| 5,443,512 A | 8/1995 | Parr et al. |
| 5,445,833 A | 8/1995 | Badylak et al. |
| 5,456,723 A | 10/1995 | Steinemann |
| 5,456,828 A | 10/1995 | Tersi et al. |
| 5,461,953 A | 10/1995 | Mccormick |
| 5,475,052 A | 12/1995 | Rhee et al. |
| 5,482,929 A | 1/1996 | Fukunaga et al. |
| 5,496,375 A | 3/1996 | Sisk et al. |
| 5,504,300 A | 4/1996 | Devanathan et al. |
| 5,510,396 A | 4/1996 | Prewett et al. |
| 5,514,536 A | 5/1996 | Taylor |
| 5,516,532 A | 5/1996 | Atala et al. |
| 5,516,533 A | 5/1996 | Badylak et al. |
| 5,535,810 A | 7/1996 | Compton et al. |
| 5,545,222 A | 8/1996 | Bonutti |
| 5,549,704 A | 8/1996 | Sutter |
| 5,549,904 A | 8/1996 | Juergensen et al. |
| 5,554,389 A | 9/1996 | Badylak et al. |
| 5,556,429 A | 9/1996 | Felt |
| 5,565,519 A | 10/1996 | Rhee et al. |
| 5,571,187 A | 11/1996 | Devanathan |
| 5,577,517 A | 11/1996 | Bonutti |
| 5,578,492 A | 11/1996 | Fedun |
| 5,585,007 A | 12/1996 | Antanavich et al. |
| 5,605,887 A | 2/1997 | Pines et al. |
| 5,612,028 A | 3/1997 | Sackier et al. |
| 5,618,925 A | 4/1997 | Dupont et al. |
| 5,624,463 A | 4/1997 | Stone et al. |
| 5,639,280 A | 6/1997 | Warner et al. |
| 5,643,192 A | 7/1997 | Hirsh et al. |
| 5,650,494 A | 7/1997 | Cerletti et al. |
| 5,654,166 A | 8/1997 | Kurth |
| 5,655,546 A | 8/1997 | Halpern |
| 5,656,587 A | 8/1997 | Sporn et al. |
| 5,662,710 A | 9/1997 | Bonutti |
| 5,669,544 A | 9/1997 | Schulze et al. |
| 5,672,284 A | 9/1997 | Devanathan et al. |
| 5,673,840 A | 10/1997 | Schulze et al. |
| 5,673,841 A | 10/1997 | Schulze et al. |
| 5,680,982 A | 10/1997 | Schulze et al. |
| 5,681,353 A | 10/1997 | Li et al. |
| 5,692,668 A | 12/1997 | Schulze et al. |
| 5,694,951 A | 12/1997 | Bonutti |
| 5,695,998 A | 12/1997 | Badylak et al. |
| 5,709,854 A | 1/1998 | Griffith-Cima et al. |
| 5,713,374 A | 2/1998 | Pachence et al. |
| 5,714,371 A | 2/1998 | Ramanathan et al. |
| 5,723,010 A | 3/1998 | Yui et al. |
| 5,723,011 A | 3/1998 | Devanathan et al. |
| 5,723,331 A | 3/1998 | Tubo et al. |
| 5,734,959 A | 3/1998 | Krebs et al. |
| 5,735,875 A | 4/1998 | Bonutti et al. |
| 5,736,132 A | 4/1998 | Juergensen et al. |
| 5,736,396 A | 4/1998 | Bruder et al. |
| 5,749,968 A | 5/1998 | Melanson et al. |
| 5,753,485 A | 5/1998 | Dwulet |
| 5,755,791 A | 5/1998 | Whitson et al. |
| 5,769,899 A | 6/1998 | Schwartz et al. |
| 5,770,194 A | 6/1998 | Edwardson et al. |
| 5,782,835 A | 7/1998 | Hart et al. |
| 5,782,915 A | 7/1998 | Stone |
| 5,786,217 A | 7/1998 | Tubo et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,811,094 A | 9/1998 | Caplan et al. |
| 5,824,093 A | 10/1998 | Ray et al. |
| 5,826,776 A | 10/1998 | Schulze et al. |
| 5,827,217 A | 10/1998 | Silver et al. |
| 5,830,741 A | 11/1998 | Dwulet et al. |
| 5,842,477 A | 12/1998 | Naughton et al. |
| 5,853,746 A | 12/1998 | Hunziker |
| 5,853,976 A | 12/1998 | Hesse et al. |
| 5,864,016 A | 1/1999 | Eibl et al. |
| 5,866,415 A | 2/1999 | Villeneuve |
| 5,866,630 A | 2/1999 | Mitra et al. |
| 5,876,208 A | 3/1999 | Mitra et al. |
| 5,876,451 A | 3/1999 | Yui et al. |
| 5,876,452 A | 3/1999 | Athanasiou et al. |
| 5,879,398 A | 3/1999 | Swarts et al. |
| 5,888,219 A | 3/1999 | Bonutti |
| 5,888,491 A | 3/1999 | Mitra et al. |
| 5,890,898 A | 4/1999 | Wada et al. |
| 5,891,455 A | 4/1999 | Sittinger et al. |
| 5,899,936 A | 5/1999 | Goldstein |
| 5,902,741 A | 5/1999 | Purchio et al. |
| 5,919,702 A | 7/1999 | Purchio et al. |
| 5,921,987 A | 7/1999 | Stone |
| 5,922,027 A | 7/1999 | Stone |
| 5,922,846 A | 7/1999 | Cerletti et al. |
| 5,926,685 A | 7/1999 | Krebs et al. |

(56) References Cited

U.S. PATENT DOCUMENTS

| | | |
|---|---|---|
| 5,928,945 A | 7/1999 | Seliktar et al. |
| 5,935,131 A | 8/1999 | Bonutti |
| 5,944,754 A | 8/1999 | Vacanti |
| 5,944,755 A | 8/1999 | Stone |
| 5,948,384 A | 9/1999 | Filler |
| 5,952,215 A | 9/1999 | Dwulet et al. |
| 5,962,405 A | 10/1999 | Seelich |
| 5,964,752 A | 10/1999 | Stone |
| 5,964,805 A | 10/1999 | Stone |
| 5,968,556 A | 10/1999 | Atala et al. |
| 5,985,315 A | 11/1999 | Patat et al. |
| 5,989,269 A | 11/1999 | Vibe-hansen et al. |
| 5,989,888 A | 11/1999 | Dwulet et al. |
| 6,022,361 A | 2/2000 | Epstein et al. |
| 6,025,334 A | 2/2000 | Dupont et al. |
| 6,045,990 A | 4/2000 | Baust et al. |
| 6,048,966 A | 4/2000 | Edwardson et al. |
| 6,051,249 A | 4/2000 | Samuelsen |
| 6,060,053 A | 5/2000 | Atala |
| 6,077,989 A | 6/2000 | Kandel et al. |
| 6,080,194 A | 6/2000 | Pachence et al. |
| 6,080,579 A | 6/2000 | Hanley, Jr. et al. |
| 6,083,383 A | 7/2000 | Huang et al. |
| 6,087,553 A | 7/2000 | Cohen et al. |
| 6,107,085 A | 8/2000 | Coughlin et al. |
| 6,110,209 A | 8/2000 | Stone |
| 6,110,210 A | 8/2000 | Norton et al. |
| 6,110,212 A | 8/2000 | Gregory |
| 6,110,482 A | 8/2000 | Khouri et al. |
| 6,120,514 A | 9/2000 | Vibe-Hansen et al. |
| 6,129,761 A | 10/2000 | Hubbell |
| 6,132,465 A | 10/2000 | Ray et al. |
| 6,132,472 A | 10/2000 | Bonutti |
| 6,140,123 A | 10/2000 | Demetriou et al. |
| 6,140,452 A | 10/2000 | Felt et al. |
| 6,143,214 A | 11/2000 | Barlow |
| 6,150,163 A | 11/2000 | McPherson et al. |
| 6,152,142 A | 11/2000 | Tseng |
| 6,162,241 A | 12/2000 | Coury et al. |
| 6,171,610 B1 | 1/2001 | Vacanti et al. |
| 6,174,313 B1 | 1/2001 | Bonutti |
| 6,179,871 B1 | 1/2001 | Halpern |
| 6,183,737 B1 | 2/2001 | Zaleske et al. |
| 6,187,329 B1 | 2/2001 | Agrawal et al. |
| 6,200,330 B1 | 3/2001 | Benderev et al. |
| 6,203,526 B1 | 3/2001 | McBeth et al. |
| 6,224,893 B1 | 5/2001 | Langer et al. |
| 6,235,316 B1 | 5/2001 | Adkisson |
| 6,242,247 B1 | 6/2001 | Rieser et al. |
| 6,248,114 B1 | 6/2001 | Ysebaert |
| 6,264,659 B1 | 7/2001 | Ross et al. |
| 6,271,320 B1 | 8/2001 | Keller et al. |
| 6,274,090 B1 | 8/2001 | Coelho et al. |
| 6,280,993 B1 | 8/2001 | Yamato et al. |
| 6,294,656 B1 | 9/2001 | Mittl et al. |
| 6,306,169 B1 | 10/2001 | Lee et al. |
| 6,306,177 B1 | 10/2001 | Felt et al. |
| 6,312,668 B2 | 11/2001 | Mitra et al. |
| 6,322,563 B1 | 11/2001 | Cummings et al. |
| 6,327,257 B1 | 12/2001 | Khalifa |
| 6,336,930 B1 | 1/2002 | Stalcup et al. |
| 6,338,878 B1 | 1/2002 | Overton et al. |
| 6,358,266 B1 | 3/2002 | Bonutti |
| 6,361,565 B1 | 3/2002 | Bonutti |
| 6,368,298 B1 | 4/2002 | Beretta et al. |
| 6,368,784 B1 | 4/2002 | Murray |
| 6,370,920 B1 | 4/2002 | Overton et al. |
| 6,378,527 B1 | 4/2002 | Hungerford et al. |
| 6,395,327 B1 | 5/2002 | Shetty |
| 6,417,320 B1 | 7/2002 | Otto et al. |
| 6,423,063 B1 | 7/2002 | Bonutti |
| 6,425,704 B2 | 7/2002 | Voiers et al. |
| 6,436,143 B1 | 8/2002 | Ross et al. |
| 6,437,018 B1 | 8/2002 | Gertzman et al. |
| 6,443,988 B2 | 9/2002 | Felt et al. |
| 6,444,228 B1 | 9/2002 | Baugh et al. |
| 6,447,514 B1 | 9/2002 | Stalcup et al. |
| 6,464,713 B2 | 10/2002 | Bonutti |
| 6,468,289 B1 | 10/2002 | Bonutti |
| 6,468,527 B2 | 10/2002 | Austin et al. |
| 6,472,162 B1 | 10/2002 | Coelho et al. |
| 6,475,764 B1 | 11/2002 | Burtscher et al. |
| 6,482,235 B1 | 11/2002 | Lambrecht et al. |
| 6,485,723 B1 | 11/2002 | Badylak et al. |
| 6,492,163 B1 | 12/2002 | Yoo et al. |
| 6,497,903 B1 | 12/2002 | Hennink et al. |
| 6,503,267 B2 | 1/2003 | Bonutti et al. |
| 6,503,277 B2 | 1/2003 | Bonutti |
| 6,504,079 B2 | 1/2003 | Tucker et al. |
| 6,511,958 B1 | 1/2003 | Atkinson et al. |
| 6,514,514 B1 | 2/2003 | Atkinson et al. |
| 6,514,522 B2 | 2/2003 | Domb |
| 6,528,052 B1 | 3/2003 | Smith et al. |
| 6,533,817 B1 | 3/2003 | Norton et al. |
| 6,534,084 B1 | 3/2003 | Vyakarnam et al. |
| 6,534,591 B2 | 3/2003 | Rhee et al. |
| 6,543,455 B2 | 4/2003 | Bonutti |
| 6,544,472 B1 | 4/2003 | Compton et al. |
| 6,551,355 B1 | 4/2003 | Lewandrowski et al. |
| 6,559,119 B1 | 5/2003 | Burgess et al. |
| 6,575,982 B1 | 6/2003 | Bonutti |
| 6,576,265 B1 | 6/2003 | Spievack |
| 6,579,538 B1 | 6/2003 | Spievack |
| 6,582,960 B1 | 6/2003 | Martin et al. |
| 6,592,531 B2 | 7/2003 | Bonutti |
| 6,596,180 B2 | 7/2003 | Baugh et al. |
| 6,599,515 B1 | 7/2003 | Delmotte |
| 6,607,534 B2 | 8/2003 | Bonutti |
| 6,610,033 B1 | 8/2003 | Melanson et al. |
| 6,620,169 B1 | 9/2003 | Peterson et al. |
| 6,626,859 B2 | 9/2003 | von Segesser |
| 6,626,945 B2 | 9/2003 | Simon et al. |
| 6,626,950 B2 | 9/2003 | Brown et al. |
| 6,630,000 B1 | 10/2003 | Bonutti |
| 6,632,246 B1 | 10/2003 | Simon et al. |
| 6,632,648 B1 | 10/2003 | Kampinga et al. |
| 6,637,437 B1 | 10/2003 | Hungerford et al. |
| 6,638,309 B2 | 10/2003 | Bonutti |
| 6,645,316 B1 | 11/2003 | Brouwer et al. |
| 6,645,764 B1 | 11/2003 | Adkisson |
| 6,649,168 B2 | 11/2003 | Arvinte et al. |
| 6,652,532 B2 | 11/2003 | Bonutti |
| 6,652,872 B2 | 11/2003 | Nevo et al. |
| 6,652,883 B2 | 11/2003 | Goupil et al. |
| 6,653,062 B1 | 11/2003 | DePablo et al. |
| 6,662,805 B2 | 12/2003 | Frondoza et al. |
| 6,663,616 B1 | 12/2003 | Roth et al. |
| 6,676,971 B2 | 1/2004 | Goupil et al. |
| 6,685,987 B2 | 2/2004 | Shetty |
| 6,697,143 B2 | 2/2004 | Freeman |
| 6,705,790 B2 | 3/2004 | Quintero et al. |
| 6,713,772 B2 | 3/2004 | Goodman et al. |
| 6,719,803 B2 | 4/2004 | Bonutti |
| 6,719,901 B2 | 4/2004 | Dolecek et al. |
| 6,730,299 B1 | 5/2004 | Tayot et al. |
| 6,733,515 B1 | 5/2004 | Edwards et al. |
| 6,736,853 B2 | 5/2004 | Bonutti |
| 6,737,072 B1 | 5/2004 | Angele et al. |
| 6,740,186 B2 | 5/2004 | Hawkins et al. |
| 6,743,232 B2 | 6/2004 | Overaker et al. |
| 6,773,458 B1 | 8/2004 | Brauker et al. |
| 6,773,713 B2 | 8/2004 | Bonassar et al. |
| 6,776,938 B2 | 8/2004 | Bonutti |
| 6,797,006 B2 | 9/2004 | Hodorek |
| 6,800,663 B2 | 10/2004 | Asgarzadeh et al. |
| 6,818,008 B1 | 11/2004 | Cates et al. |
| 6,830,762 B2 | 12/2004 | Baugh et al. |
| 6,833,408 B2 | 12/2004 | Sehl et al. |
| 6,835,198 B2 | 12/2004 | Bonutti |
| 6,835,277 B2 | 12/2004 | Park |
| 6,840,960 B2 | 1/2005 | Bubb |
| 6,852,330 B2 | 2/2005 | Bowman et al. |
| 6,860,904 B2 | 3/2005 | Bonutti |
| 6,884,428 B2 | 4/2005 | Binette et al. |

(56) References Cited

U.S. PATENT DOCUMENTS

| | | |
|---|---|---|
| 6,886,568 B2 | 5/2005 | Frondoza et al. |
| 6,893,466 B2 | 5/2005 | Trieu |
| 6,905,517 B2 | 6/2005 | Bonutti |
| 6,919,067 B2 | 7/2005 | Filler et al. |
| 6,919,172 B2 | 7/2005 | DePablo et al. |
| 6,921,633 B2 | 7/2005 | Baust et al. |
| 6,942,880 B1 | 9/2005 | Dolecek |
| 6,949,252 B2 | 9/2005 | Mizuno et al. |
| 6,965,014 B1 | 11/2005 | Delmotte et al. |
| 6,979,307 B2 | 12/2005 | Beretta et al. |
| 6,990,982 B1 | 1/2006 | Bonutti |
| 6,991,652 B2 | 1/2006 | Burg |
| 7,009,039 B2 | 3/2006 | Yayon et al. |
| 7,045,601 B2 | 5/2006 | Metzner et al. |
| 7,067,123 B2 | 6/2006 | Gomes et al. |
| 7,081,125 B2 | 7/2006 | Edwards et al. |
| 7,083,964 B2 | 8/2006 | Kurfurst |
| 7,087,227 B2 | 8/2006 | Adkisson |
| RE39,321 E | 10/2006 | MacPhee et al. |
| 7,134,437 B2 | 11/2006 | Bonutti |
| 7,147,471 B2 | 12/2006 | Frey et al. |
| 7,217,294 B2 | 5/2007 | Kusanagi et al. |
| 7,235,255 B2 | 6/2007 | Austin et al. |
| 7,273,756 B2 | 9/2007 | Adkisson et al. |
| 7,276,235 B2 | 10/2007 | Metzner et al. |
| 7,276,481 B2 | 10/2007 | Golembo et al. |
| 7,299,805 B2 | 11/2007 | Bonutti |
| 7,316,822 B2 | 1/2008 | Binette et al. |
| 7,375,077 B2 | 5/2008 | Mao |
| 7,468,192 B2 | 12/2008 | Mizuno et al. |
| 7,488,348 B2 | 2/2009 | Truncale et al. |
| 7,537,780 B2 | 5/2009 | Mizuno et al. |
| 7,720,533 B2 | 5/2010 | Behravesh |
| 7,824,711 B2 * | 11/2010 | Kizer et al. .................. 424/499 |
| 7,838,040 B2 | 11/2010 | Malinin |
| 7,875,296 B2 | 1/2011 | Binette et al. |
| 7,879,604 B2 | 2/2011 | Seyedin et al. |
| RE42,208 E | 3/2011 | Truncale et al. |
| 7,897,384 B2 | 3/2011 | Binette et al. |
| 7,901,457 B2 | 3/2011 | Truncale et al. |
| 7,901,461 B2 | 3/2011 | Harmon et al. |
| 8,017,394 B2 | 9/2011 | Adkisson, IV et al. |
| 8,025,901 B2 | 9/2011 | Kao et al. |
| 8,137,702 B2 | 3/2012 | Binette et al. |
| 8,163,549 B2 | 4/2012 | Yao et al. |
| 8,480,757 B2 | 7/2013 | Gage et al. |
| 8,497,121 B2 | 7/2013 | Yao et al. |
| 2001/0004710 A1 | 6/2001 | Felt et al. |
| 2001/0006634 A1 | 7/2001 | Zaleske et al. |
| 2001/0014473 A1 | 8/2001 | Rieser et al. |
| 2001/0014475 A1 | 8/2001 | Frondoza et al. |
| 2001/0051834 A1 | 12/2001 | Frondoza et al. |
| 2001/0055621 A1 | 12/2001 | Baugh et al. |
| 2002/0004038 A1 | 1/2002 | Baugh et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0029055 A1 | 3/2002 | Bonutti |
| 2002/0045940 A1 | 4/2002 | Giannetti et al. |
| 2002/0055755 A1 | 5/2002 | Bonutti |
| 2002/0062151 A1 | 5/2002 | Altman et al. |
| 2002/0064512 A1 | 5/2002 | Petersen et al. |
| 2002/0082623 A1 | 6/2002 | Osther et al. |
| 2002/0095160 A1 | 7/2002 | Bonutti |
| 2002/0099401 A1 | 7/2002 | Bonutti |
| 2002/0099448 A1 | 7/2002 | Hiles et al. |
| 2002/0106625 A1 | 8/2002 | Hung et al. |
| 2002/0123142 A1 | 9/2002 | Hungerford et al. |
| 2002/0128683 A1 | 9/2002 | Epstein |
| 2002/0133235 A1 | 9/2002 | Hungerford et al. |
| 2002/0150550 A1 | 10/2002 | Petersen |
| 2002/0151974 A1 | 10/2002 | Bonassar et al. |
| 2002/0159982 A1 | 10/2002 | Bonassar et al. |
| 2002/0159985 A1 | 10/2002 | Baugh et al. |
| 2002/0183850 A1 | 12/2002 | Felt et al. |
| 2002/0198490 A1 | 12/2002 | Wirt et al. |
| 2002/0198599 A1 | 12/2002 | Haldimann |
| 2003/0009147 A1 | 1/2003 | Bonutti |
| 2003/0009235 A1 | 1/2003 | Manrique et al. |
| 2003/0039695 A1 | 2/2003 | Geistlich et al. |
| 2003/0040113 A1 | 2/2003 | Mizuno et al. |
| 2003/0065389 A1 | 4/2003 | Petersen |
| 2003/0069605 A1 | 4/2003 | Bonutti et al. |
| 2003/0077244 A1 | 4/2003 | Petersen |
| 2003/0099620 A1 | 5/2003 | Zaleske et al. |
| 2003/0114936 A1 | 6/2003 | Sherwood et al. |
| 2003/0134032 A1 | 7/2003 | Chaouk et al. |
| 2003/0151974 A1 | 8/2003 | Kutty et al. |
| 2003/0153078 A1 | 8/2003 | Libera et al. |
| 2003/0176602 A1 | 9/2003 | Schmidt et al. |
| 2003/0181939 A1 | 9/2003 | Bonutti |
| 2003/0187387 A1 | 10/2003 | Wirt et al. |
| 2003/0195628 A1 | 10/2003 | Bao et al. |
| 2003/0211073 A1 | 11/2003 | Goupil et al. |
| 2003/0223956 A1 | 12/2003 | Goupil et al. |
| 2004/0030404 A1 | 2/2004 | Noll et al. |
| 2004/0030406 A1 | 2/2004 | Ochi et al. |
| 2004/0033212 A1 | 2/2004 | Thomson et al. |
| 2004/0042960 A1 | 3/2004 | Frey et al. |
| 2004/0044408 A1 | 3/2004 | Hungerford et al. |
| 2004/0048796 A1 | 3/2004 | Hariri et al. |
| 2004/0059416 A1 | 3/2004 | Murray et al. |
| 2004/0064192 A1 | 4/2004 | Bubb |
| 2004/0064193 A1 | 4/2004 | Evans et al. |
| 2004/0073308 A1 | 4/2004 | Kuslich et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0092946 A1 | 5/2004 | Bagga et al. |
| 2004/0097714 A1 | 5/2004 | Maubois et al. |
| 2004/0097829 A1 | 5/2004 | McRury et al. |
| 2004/0117033 A1 | 6/2004 | Frondoza et al. |
| 2004/0127987 A1 | 7/2004 | Evans et al. |
| 2004/0134502 A1 | 7/2004 | Mizuno et al. |
| 2004/0138522 A1 | 7/2004 | Haarstad et al. |
| 2004/0151705 A1 | 8/2004 | Mizuno et al. |
| 2004/0172045 A1 | 9/2004 | Eriksson et al. |
| 2004/0175690 A1 | 9/2004 | Mishra et al. |
| 2004/0176787 A1 | 9/2004 | Mishra et al. |
| 2004/0181240 A1 | 9/2004 | Tseng et al. |
| 2004/0191900 A1 | 9/2004 | Mizuno et al. |
| 2004/0193181 A1 | 9/2004 | Bonutti |
| 2004/0219182 A1 | 11/2004 | Gomes et al. |
| 2004/0228901 A1 | 11/2004 | Trieu et al. |
| 2004/0230303 A1 | 11/2004 | Gomes et al. |
| 2004/0230309 A1 | 11/2004 | DiMauro et al. |
| 2005/0026133 A1 | 2/2005 | Nakatsuji et al. |
| 2005/0038520 A1 | 2/2005 | Binette et al. |
| 2005/0043805 A1 | 2/2005 | Chudik |
| 2005/0043814 A1 | 2/2005 | Kusanagi et al. |
| 2005/0054595 A1 | 3/2005 | Binette et al. |
| 2005/0064042 A1 | 3/2005 | Vunjak-Novakovic et al. |
| 2005/0079159 A1 | 4/2005 | Shastri et al. |
| 2005/0095235 A1 | 5/2005 | Austin et al. |
| 2005/0095666 A1 | 5/2005 | Jhavar et al. |
| 2005/0113736 A1 | 5/2005 | Orr et al. |
| 2005/0113937 A1 | 5/2005 | Binette et al. |
| 2005/0119754 A1 | 6/2005 | Trieu et al. |
| 2005/0123520 A1 | 6/2005 | Eavey et al. |
| 2005/0124038 A1 | 6/2005 | Aguiar et al. |
| 2005/0125077 A1 | 6/2005 | Harmon et al. |
| 2005/0136046 A1 | 6/2005 | Pines et al. |
| 2005/0137600 A1 | 6/2005 | Jacobs et al. |
| 2005/0139656 A1 | 6/2005 | Arnouse |
| 2005/0152882 A1 | 7/2005 | Kizer et al. |
| 2005/0152886 A1 | 7/2005 | Baugh et al. |
| 2005/0152961 A1 | 7/2005 | Austin et al. |
| 2005/0171470 A1 | 8/2005 | Kucklick et al. |
| 2005/0175657 A1 | 8/2005 | Hunter et al. |
| 2005/0175704 A1 | 8/2005 | Petersen |
| 2005/0175711 A1 | 8/2005 | Kralovee et al. |
| 2005/0177249 A1 | 8/2005 | Kladakis et al. |
| 2005/0186247 A1 | 8/2005 | Hunter |
| 2005/0186283 A1 | 8/2005 | Geistlich et al. |

(56) References Cited

U.S. PATENT DOCUMENTS

| | | |
|---|---|---|
| 2005/0186673 A1 | 8/2005 | Geistlich et al. |
| 2005/0192532 A1 | 9/2005 | Kucklick et al. |
| 2005/0196387 A1 | 9/2005 | Seyedin et al. |
| 2005/0196460 A1 | 9/2005 | Malinin |
| 2005/0203342 A1 | 9/2005 | Kucklick et al. |
| 2005/0209601 A1 | 9/2005 | Bowman et al. |
| 2005/0209602 A1 | 9/2005 | Bowman et al. |
| 2005/0222687 A1 | 10/2005 | Vunjak-Novakovic et al. |
| 2005/0226856 A1 | 10/2005 | Ahlfors |
| 2005/0234298 A1 | 10/2005 | Kucklick et al. |
| 2005/0234485 A1 | 10/2005 | Seegert et al. |
| 2005/0244454 A1 | 11/2005 | Elson et al. |
| 2005/0250697 A1 | 11/2005 | Maubois et al. |
| 2005/0250698 A1 | 11/2005 | Maubois et al. |
| 2005/0251268 A1 | 11/2005 | Truncale |
| 2005/0265980 A1 | 12/2005 | Chen et al. |
| 2005/0267584 A1 | 12/2005 | Burdulis, Jr. et al. |
| 2005/0273129 A1 | 12/2005 | Michels et al. |
| 2005/0287218 A1 | 12/2005 | Chaouk et al. |
| 2005/0288796 A1 | 12/2005 | Awad et al. |
| 2006/0008530 A1 | 1/2006 | Seyedin et al. |
| 2006/0009779 A1 | 1/2006 | Collins et al. |
| 2006/0019389 A1 | 1/2006 | Yayon et al. |
| 2006/0024373 A1 | 2/2006 | Shahar et al. |
| 2006/0024826 A1 | 2/2006 | Bonassar et al. |
| 2006/0029679 A1 | 2/2006 | Dolecek |
| 2006/0041270 A1 | 2/2006 | Lenker et al. |
| 2006/0073588 A1 | 4/2006 | Adkisson et al. |
| 2006/0078872 A1 | 4/2006 | Taguchi et al. |
| 2006/0099706 A1 | 5/2006 | Massey et al. |
| 2006/0111738 A1 | 5/2006 | Wenchell |
| 2006/0111778 A1 | 5/2006 | Michalow |
| 2006/0128016 A1 | 6/2006 | Tokushima et al. |
| 2006/0134093 A1 | 6/2006 | Ronfard |
| 2006/0134094 A2 | 6/2006 | Delmotte et al. |
| 2006/0147547 A1 | 7/2006 | Yayon |
| 2006/0153815 A1 | 7/2006 | Seyda et al. |
| 2006/0183224 A1 | 8/2006 | Aerts et al. |
| 2006/0195188 A1 | 8/2006 | O'Driscoll et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0240064 A9 | 10/2006 | Hunter et al. |
| 2006/0240555 A1 | 10/2006 | Ronfard |
| 2006/0251631 A1 | 11/2006 | Adkisson, IV et al. |
| 2006/0264966 A1 | 11/2006 | Armstrong |
| 2006/0275273 A1 | 12/2006 | Seyedin et al. |
| 2006/0281173 A1 | 12/2006 | Fukuda et al. |
| 2006/0292131 A1 | 12/2006 | Binette et al. |
| 2007/0014867 A1 | 1/2007 | Kusanagi et al. |
| 2007/0031471 A1 | 2/2007 | Peyman |
| 2007/0038299 A1 | 2/2007 | Stone et al. |
| 2007/0041952 A1 | 2/2007 | Guilak et al. |
| 2007/0077236 A1 | 4/2007 | Osther |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2007/0191781 A1 | 8/2007 | Richards et al. |
| 2007/0212389 A1 | 9/2007 | Weiss et al. |
| 2007/0213660 A1 | 9/2007 | Richards et al. |
| 2007/0250164 A1 | 10/2007 | Troxel |
| 2007/0292945 A1 | 12/2007 | Lin et al. |
| 2007/0299517 A1 | 12/2007 | Davisson et al. |
| 2008/0009942 A1 | 1/2008 | Mizuno et al. |
| 2008/0031934 A1 | 2/2008 | MacPhee et al. |
| 2008/0033331 A1 | 2/2008 | MacPhee et al. |
| 2008/0033332 A1 | 2/2008 | MacPhee et al. |
| 2008/0033333 A1 | 2/2008 | MacPhee et al. |
| 2008/0039940 A1 | 2/2008 | Hashimoto et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0081369 A1 | 4/2008 | Adkisson, IV et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0199429 A1 | 8/2008 | Hollander et al. |
| 2008/0274157 A1 | 11/2008 | Vunjak-Novakovic et al. |
| 2008/0299214 A1 | 12/2008 | Seyedin et al. |
| 2009/0012629 A1 | 1/2009 | Yao et al. |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale et al. |
| 2009/0319045 A1 | 12/2009 | Truncale et al. |
| 2010/0015202 A1 | 1/2010 | Semler et al. |
| 2010/0086594 A1 | 4/2010 | Amit et al. |
| 2010/0121311 A1 | 5/2010 | Seegert et al. |
| 2010/0168856 A1 | 7/2010 | Long et al. |
| 2010/0209397 A1 | 8/2010 | Maor |
| 2010/0209408 A1 | 8/2010 | Stephen et al. |
| 2010/0274362 A1 | 10/2010 | Yayon et al. |
| 2010/0303765 A1 | 12/2010 | Athanasiou et al. |
| 2010/0322994 A1 | 12/2010 | Kizer et al. |
| 2011/0009963 A1 | 1/2011 | Binnette et al. |
| 2011/0052705 A1 | 3/2011 | Malinin |
| 2011/0070271 A1 | 3/2011 | Truncale et al. |
| 2011/0091517 A1 | 4/2011 | Binette et al. |
| 2011/0097381 A1 | 4/2011 | Binette et al. |
| 2011/0166669 A1 | 7/2011 | Truncale et al. |
| 2011/0177134 A1 | 7/2011 | Harmon et al. |
| 2011/0196508 A1 | 8/2011 | Truncale et al. |
| 2011/0256095 A1 | 10/2011 | Seyedin et al. |
| 2012/0009224 A1 | 1/2012 | Kizer et al. |
| 2012/0009270 A1 | 1/2012 | Kizer et al. |
| 2012/0107384 A1 | 5/2012 | Yao et al. |
| 2012/0156265 A1 | 6/2012 | Binette et al. |
| 2012/0183586 A1 | 7/2012 | Yao et al. |
| 2012/0239146 A1 | 9/2012 | Kizer et al. |

FOREIGN PATENT DOCUMENTS

| | | |
|---|---|---|
| CA | 2261292 A1 | 7/1997 |
| CA | 2261292 C | 7/1997 |
| CA | 2441994 A1 | 3/2002 |
| CA | 2445356 A1 | 10/2003 |
| CA | 2445356 C | 10/2003 |
| CA | 2445558 A1 | 10/2003 |
| CA | 2445558 C | 10/2003 |
| CA | 2449227 A1 | 11/2003 |
| CA | 2449227 C | 11/2003 |
| CA | 2522133 A1 | 4/2004 |
| CA | 2522133 C | 4/2004 |
| CA | 2475905 A1 | 7/2004 |
| CA | 2475905 C | 7/2004 |
| CA | 2480712 A1 | 9/2004 |
| CA | 2487029 A1 | 11/2004 |
| CA | 2487042 A1 | 11/2004 |
| CA | 2522133 C | 11/2004 |
| CA | 2496184 A1 | 2/2005 |
| CA | 2563082 A1 | 3/2005 |
| CA | 2570521 A1 | 3/2006 |
| CA | 2631520 A1 | 6/2007 |
| CA | 2708147 A1 | 12/2008 |
| CA | 2717725 A1 | 3/2009 |
| EP | 0006216 A1 | 1/1980 |
| EP | 0133934 A2 | 3/1985 |
| EP | 0341007 A2 | 4/1989 |
| EP | 1142581 A2 | 11/1991 |
| EP | 0610423 B1 | 10/1992 |
| EP | 0654078 B1 | 6/1993 |
| EP | 0493387 B1 | 10/1993 |
| EP | 0641007 A2 | 1/1994 |
| EP | 0592242 A1 | 4/1994 |
| EP | 0669138 A2 | 2/1995 |
| EP | 0669138 A2 | 8/1995 |

(56) References Cited

FOREIGN PATENT DOCUMENTS

| | | | |
|---|---|---|---|
| EP | 0906069 B1 | 11/1996 |
| EP | 0877632 B1 | 9/1997 |
| EP | 0867193 A2 | 9/1998 |
| EP | 01010356 A1 | 6/2000 |
| EP | 1132061 A2 | 9/2001 |
| EP | 867193 B1 | 12/2002 |
| EP | 1264607 A1 | 12/2002 |
| EP | 1003568 B1 | 4/2003 |
| EP | 0592242 B1 | 7/2003 |
| EP | 1538196 A1 | 8/2003 |
| EP | 1410810 A1 | 10/2003 |
| EP | 1410810 B1 | 10/2003 |
| EP | 1410811 A1 | 10/2003 |
| EP | 1410811 B1 | 10/2003 |
| EP | 1433423 A1 | 10/2003 |
| EP | 1433423 B1 | 10/2003 |
| EP | 1599126 | 3/2004 |
| EP | 1410810 A1 | 4/2004 |
| EP | 1410811 | 4/2004 |
| EP | 1618178 B1 | 4/2004 |
| EP | 1506790 A1 | 8/2004 |
| EP | 1512739 A1 | 9/2004 |
| EP | 1471140 A1 | 10/2004 |
| EP | 1537883 A2 | 12/2004 |
| EP | 1537883 A3 | 12/2004 |
| EP | 1537883 B1 | 12/2004 |
| EP | 1691727 B1 | 12/2004 |
| EP | 1958651 B1 | 12/2004 |
| EP | 2335650 A1 | 12/2004 |
| EP | 2338441 A1 | 12/2004 |
| EP | 2338442 A1 | 12/2004 |
| EP | 2338533 A1 | 12/2004 |
| EP | 1561481 A2 | 2/2005 |
| EP | 1561481 A3 | 2/2005 |
| EP | 1561481 B1 | 2/2005 |
| EP | 1753860 B1 | 2/2005 |
| EP | 1535578 A1 | 6/2005 |
| EP | 1535633 A1 | 6/2005 |
| EP | 1537883 A2 | 6/2005 |
| EP | 1561481 A2 | 8/2005 |
| EP | 1512739 A1 | 9/2005 |
| EP | 1387703 B1 | 7/2006 |
| EP | 1303184 B1 | 9/2006 |
| EP | 1788077 A1 | 5/2007 |
| EP | 0920490 | 2/2008 |
| EP | 1537883 B1 | 4/2008 |
| EP | 1618178 B1 | 7/2008 |
| EP | 2101681 B1 | 8/2011 |
| EP | 2335650 B1 | 10/2012 |
| EP | 2338441 B1 | 1/2013 |
| EP | 2338442 B1 | 1/2013 |
| GB | 2105198 A | 3/1983 |
| GB | 2175507 A | 5/1985 |
| GB | 2404607 A | 9/2005 |
| JP | 59135054 A | 8/1984 |
| JP | 2004136096 A | 5/2004 |
| JP | 2006230749 | 9/2006 |
| JP | 2003102755 A | 4/2008 |
| WO | 8002501 A1 | 5/1980 |
| WO | 8505274 A1 | 5/1985 |
| WO | 9000060 A1 | 1/1990 |
| WO | WO-9101711 A1 | 2/1991 |
| WO | WO-9209697 A1 | 6/1992 |
| WO | 9603160 A1 | 2/1996 |
| WO | WO-9603112 A1 | 2/1996 |
| WO | WO-9639170 A1 | 12/1996 |
| WO | 9711090 A1 | 3/1997 |
| WO | WO-9726847 A1 | 7/1997 |
| WO | 9804681 | 2/1998 |
| WO | 9804681 A2 | 2/1998 |
| WO | WO-9844874 A1 | 10/1998 |
| WO | WO-9907417 A1 | 2/1999 |
| WO | 9951164 A1 | 3/1999 |
| WO | WO-0006216 A1 | 2/2000 |
| WO | 0029484 A1 | 5/2000 |
| WO | WO-0048837 A1 | 8/2000 |
| WO | 0056251 | 9/2000 |
| WO | WO-0056251 A1 | 9/2000 |
| WO | WO-0062832 A1 | 10/2000 |
| WO | WO-0102030 A2 | 1/2001 |
| WO | WO-0105443 A1 | 1/2001 |
| WO | WO-0110356 A2 | 2/2001 |
| WO | WO-0123014 A1 | 4/2001 |
| WO | WO-0123014 A1 | 4/2001 |
| WO | WO-0167961 A1 | 9/2001 |
| WO | WO-0168811 A2 | 9/2001 |
| WO | WO-0168811 A3 | 9/2001 |
| WO | WO-0185225 A2 | 11/2001 |
| WO | WO-0197872 A1 | 12/2001 |
| WO | 0267856 A2 | 2/2002 |
| WO | 0224244 A2 | 3/2002 |
| WO | 0276285 A2 | 3/2002 |
| WO | WO-0185225 A3 | 3/2002 |
| WO | 0280991 A2 | 4/2002 |
| WO | WO-02089868 A1 | 11/2002 |
| WO | 03077794 A2 | 3/2003 |
| WO | WO-03093433 A2 | 11/2003 |
| WO | WO-03100417 A1 | 12/2003 |
| WO | 2004078032 A2 | 3/2004 |
| WO | 2004078032 A3 | 3/2004 |
| WO | 2004028584 A1 | 4/2004 |
| WO | 2004096983 A2 | 4/2004 |
| WO | WO-2004028547 A1 | 4/2004 |
| WO | 2004105576 A2 | 5/2004 |
| WO | WO-03093433 A3 | 7/2004 |
| WO | 2004078032 A2 | 9/2004 |
| WO | WO-2004078032 A3 | 9/2004 |
| WO | WO-2004078035 A2 | 9/2004 |
| WO | WO-2004078955 A1 | 9/2004 |
| WO | WO-2004110308 A2 | 12/2004 |
| WO | WO-2004110512 A2 | 12/2004 |
| WO | 2005081870 A2 | 2/2005 |
| WO | 2005018491 A2 | 3/2005 |
| WO | 2005092208 A1 | 3/2005 |
| WO | 2005092405 A1 | 3/2005 |
| WO | 2005110278 A2 | 3/2005 |
| WO | WO-2004110512 A3 | 5/2005 |
| WO | WO-2005044326 A1 | 5/2005 |
| WO | 2005058207 A1 | 6/2005 |
| WO | 2005060987 A1 | 7/2005 |
| WO | 2005061018 A1 | 7/2005 |
| WO | WO-2005061019 A2 | 7/2005 |
| WO | WO-2005065079 A1 | 7/2005 |
| WO | 2005110278 A2 | 11/2005 |
| WO | WO-2005113751 A1 | 12/2005 |
| WO | 2006002253 A2 | 1/2006 |
| WO | WO-2006002253 A3 | 1/2006 |
| WO | 2006090372 A2 | 2/2006 |
| WO | 2006090372 A3 | 2/2006 |
| WO | WO-2006017176 A2 | 2/2006 |
| WO | 2006033698 A2 | 3/2006 |
| WO | 2006113642 A1 | 4/2006 |
| WO | WO-2006039484 A2 | 4/2006 |
| WO | WO-2006041723 A1 | 4/2006 |
| WO | 2006068972 A2 | 6/2006 |
| WO | WO-2006059198 A1 | 6/2006 |
| WO | WO-2006033698 A3 | 7/2006 |
| WO | WO-2006121612 A1 | 11/2006 |
| WO | WO-2005081870 A3 | 12/2006 |
| WO | WO-2006039484 A3 | 1/2007 |
| WO | 2007025290 A2 | 3/2007 |
| WO | 2007102149 A2 | 3/2007 |
| WO | 2007115336 A2 | 4/2007 |
| WO | 2007054939 A2 | 5/2007 |
| WO | 2007067637 A2 | 6/2007 |
| WO | 2007143726 A2 | 6/2007 |
| WO | WO-2007089942 A2 | 8/2007 |
| WO | WO-2007089948 A2 | 8/2007 |
| WO | WO-2007025290 A3 | 10/2007 |
| WO | 2007143726 A2 | 12/2007 |
| WO | 2008106254 A2 | 1/2008 |
| WO | WO-2007089948 A3 | 1/2008 |
| WO | 2008021127 A2 | 2/2008 |
| WO | WO-2008019127 A2 | 2/2008 |

(56) References Cited

FOREIGN PATENT DOCUMENTS

| WO | WO-2008019128 A2 | 2/2008 |
|---|---|---|
| WO | WO-2008019129 A2 | 2/2008 |
| WO | 2008128075 A1 | 4/2008 |
| WO | 2008079194 A1 | 7/2008 |
| WO | WO-2008079613 A1 | 7/2008 |
| WO | 2009039469 A1 | 3/2009 |
| WO | 2009111069 A1 | 3/2009 |
| WO | 2009076164 A2 | 6/2009 |
| WO | 2010078040 A1 | 7/2010 |

OTHER PUBLICATIONS

Langer, F. et al, The Immunogenicity of Fresh and Frozen Allogeneic Bone, JBJS, 1975, pp. 216-220, vol. 57-A, No. 2.
Lavrishcheva, G.I., Filling Bone Cavities with Minced Cartilage, Ortopediia travmatologiia I protezirovanie, 1955, pp. 80, vol. 1.
Lee, J.W., Preplanned correction of enophthalmos using diced cartilage grafts, British J. Plastic Surg, 2000, pp. 17-23, vol. 53.
Lemperg, R., et al, Transplantation of diced rib cartilage to the hip joint. Experimental study on adult dogs, Acta Soc Med Ups, 1965, pp. 197-212, vol. 70, No. 3.
Lennert, K.H. and Haas, H.G., Fibrin Adhesive in the Surgical Treatment of the Pseudoarthrosis of the Scaphoid Bone-Methods and Results, Unfallchirurgie, 1988, pp. 158-160, vol. 14, No. 3.
Leopold, G., XIV. Experimental Studies into the Etiology of Tumors, Archiv f. path. Anat., 1881, pp. 283-324, vol. LXXXV, No. 2.
Limberg, A.A., Supporting and Contour Plastic Repair by Needle Administration of Minced Carthage, Vestnik khirurgii imeni I.I. Grekova, 1957, pp. 68-73, vol. 78, No. 4.
Limberg, A.A., The use of diced cartilage by injection with a needle. Part 1. Clinical investigations, Plast Reconstr Surg Transplant Bull., 1961, pp. 523-36, vol. 28.
Limberg, A.A., The use of diced cartilage by injection with a needle. Part 2. Morphologic Changes in The Diced Human Cartilage After Auto- and Homoplasty, Plast Reconstr Surg Transplant Bull., 1961, pp. 649-655, vol. 28.
Loeb, L, Autotransplantation and Homoiotransplantation of Cartilage in the Guinea-Pig, Am. J. Pathology, 1926, pp. 111-122, vol. II.
Lu, Y. et al, Minced Cartilage without Cell Culture Serves as an Effective Intraoperative Cell Source for Cartilage Repair, J Orthop Res., 2006, pp. 1261-1270, vol. 24, No. 6.
Lucht, U. et al, Fibrin sealant in bone transplantation. No effects on blood flow and bone formation in dogs, Acta Orthop Scand., 1986, pp. 19-24, vol. 57, No. 1.
Mahomed, M.N. et al, The long-term success of fresh, small fragment osteochondral allografts used for intraarticular post-traumatic defects in the knee joint, Orthopedics, 1992, pp. 1191-1199, vol. 15, No. 10.
Maletius, W. and Lundberg, M., Refixation of large chondral fragments on the weight-bearing area of the knee joint: a report of two cases, Arthroscopy., 1994, pp. 630-633, vol. 10, No. 6.
Mankin, H.J., Localization of Tritiated Thymidine in Articular Cartilage of Rabbits: II. Repair in Immature Cartilage, JBJS, 1962, pp. 688-698, vol. 44.
Mankin, H.J., Localization of Tritiated Thymidine in Articular Cartilage of Rabbits: III. Mature Articular Cartilage, JBJS, 1963, pp. 529-540, vol. 45.
Mankin, H.J., Current Concepts Review, The Response of Articular Cartilage to Mechanical Injury, JBJS, 1982, pp. 460-466, vol. 64, No. 3.
Marcacci, M. et al, Articular cartilage engineering with Hyalograft C: 3-year clinical results, Clin Orthop Relat Res., 2005, pp. 96-105, No. 435.
Marcacci, M. et al, Use of autologous grafts for reconstruction of osteochondral defects of the knee, Orthopedics, 1999, pp. 595-600, vol. 22, No. 6.
Marchac, D. And Sandor, G., Face lifts and sprayed fibrin glue: an outcome analysis of 200 patients, Br J Plast Surg., 1994, pp. 306-309, vol. 47, No. 5.
Marchac, D. et al, Fibrin glue fixation in forehead endoscopy: evaluation of our experience with 206 cases, Plast Reconstr Surg., 1997, pp. 713-714, vol. 100, No. 3.
Matras, H., Fibrin Seal: The State of the Art, J. Oral Maxilofac Surg, 1985, pp. 605-611, vol. 43.
Matsusue, Y. et al, Biodegradable Pin Fixation of Osteochondral Fragments of the Knee, Clin Ortho Rel Res, 1996, pp. 166-173, No. 322.
McDermott, A.G.P. et al, Fresh Small-Fragment Osteochondral Allografts, Clin Orthop Relat Res., 1985, pp. 96-102, No. 197.
McKibbin, B, Immature Joint Cartilage and the Homograft Reaction, JBJS, 1971, pp. 123-135, vol. 53B, No. 1.
Meachim, G. and Roberts, C., Repair of the joint surface from subarticular tissue in the rabbit knee, J Anat., 1971, pp. 317-327, vol. 109, Part 2.
Meyers, M.H. and Herron, M., A Fibrin Adhesive Seal for the Repair of Osteochondral Fracture Fragments, Clin Ortho Rel Res, 1984, pp. 258-263, No. 182.
Mitchell, N. and Shepard, N., The resurfacing of adult rabbit articular cartilage by multiple perforations through the subchondral bone, JBJS, 1976, pp. 230-233, vol. 58, No. 2.
Mithofer, K. et al, Functional outcome of knee articular cartilage repair in adolescent athletes, Am J Sports Med., 2005, pp. 1147-1153, vol. 33, No. 8.
Miura, Y et al, Brief exposure to high-dose transforming growth factor-beta1 enhances periosteal chondrogenesis in vitro: a preliminary report, JBJS, 2002, pp. 793-799, vol. 84-A, No. 5.
Murray, M.M. and Spector, M, The migration of cells from the ruptured human anterior cruciate ligament into collagen-glycosaminoglycan regeneration templates in vitro, Biomaterials, 2001, pp. 2393-2402, vol. 22.
Nageotte, J., The Organization of Matter in its Connections with Life. Studies of General Anatomy and Experimental Morphology on teh Connective Tissue and the Nerve, L'Organisation De La Matiere, 1922, pp. 95-98.
Niekisch, V.R., English Summary only of Possible methods of using fibrin-glue protection in maxillo facial surgery, Zahn Mund Kieferheilkd Zentralbl, 1980, pp. 555-561, vol. 68, No. 6.
Nixon, A.J., et al, Isolation, propagation, and cryopreservation of equine articular chondrocytes, AM J Vet Res, 1992, pp. 2364-2370, vol. 53, No. 12.
Nixon, A.J., and Fortier, L.A, New Horizons in Articular Cartilage Repair, AAEP Proceedings, 2001, pp. 217-226, vol. 47.
O'Driscoll, S.W. et al, The chondrogenic potential of free autogenous periosteal grafts for biological resurfacing of major full-thickness defects in joint surfaces under the influence of continuous passive motion. An experimental investigation in the rabbit, J Bone Joint Surg Am, 1986, pp. 1017-1035, vol. 68, No. 7.
O'Driscoll, S.W. and Salter, R.B., The Repair of Major Osteochondral Defects in Joint Surfaces by Neochondrogenesis with Autogenous Osteoperiosteal Grafts Stimulated by Continuous Passive Motion, Clin Ortho Rel Res, 1986, pp. 131-140, No. 208.
Oegema, T.R. and Thompson, R.C. Jr, Characterization of a hyaluronic acid-dermatan sulfate proteoglycan complex from dedifferentiated human chondrocyte cultures, J Biol Chem., 1981, pp. 1015-1022, vol. 256, No. 2.
Ohlsen, L. and Widenfalk, B., The Early Development of Articular Cartilage After Perichondrial Grafting, Scand J. Plast Reconstr Surg, 1983, pp. 163-177, vol. 17.
Outerbridge, H.K. et al, The Use of a Lateral Patellar Autologous Graft for the Repair of a Large Osteochondral Defect in the Knee, J Bone Joint Surg Am., 1995, pp. 65-72, vol. 77, No. 1.
Paar, O. et al,Cartilage Adhesion at the Knee Joint, Clinical Follow up Examination, Akt. Traumatol, 1984, pp. 15-19, vol. 14.
Paccola, C.A. et al, Fresh Immature Articular Cartilage Allografts—A Study on the Integration of Chondral and Osteochondral Grafts Both in Normal and in Papain-Treated Knee Joints of Rabbits, Arch Orthop Traumat Surg., 1979, pp. 253-259, vol. 93.
Park, J.J. et al, Comparison of the Bonding Power of Various Autologous Fibrin Tissue Adhesives, Am J Otology, 1997, pp. 655-659, vol. 18, No. 5.

(56) References Cited

OTHER PUBLICATIONS

Park, M.S., Tympanoplasty using autologous crushed cartilage, Rev Laryngol Otol Rhinol, 1995, pp. 365-368, vol. 116, No. 5.

Pascone, M. and Dioguardi, D., Fibrin Sealant in Plastic Surgery of the Head, Plastic Surgery Nerve Repair Burns, Fibring Sealing in Surgical and Nonsurgical Fields, 1995, pp. 11-15, vol. 3, Springer-Verlag, Berlin Heidelberg.

Passl, R. et al, Problems of Pure Homologous Articular Cartilage Transplantation, Verh Anat Ges, 1976, pp. 675-678, vol. 70.

Punzet, G. et al, Morphological and Therapeutic Aspects of Osteochondrosis dissecans and Aseptic Bone Necroses, Acta Medica Austriaca, 1978, pp. 17-18, Suppl. No. 11.

Passl, R. et al, Fibrin Gluing of Cartilage Surfaces—Experimental Studies and Clinical Results, Med. u. Sport, 1979, pp. 23-28, vol. 19 (1/2).

Passl, R. et al, Homologous Cartilage Transplants in Animal Experiments, 4th Orthopedics Symposium, Heidelberg, 1981, pp. 102-105, Horst Cotta and Arnim Braun (eds), Georg Thieme Verlag Stuttgart, New York.

Schaffer, D.J. et al, English abstract only of foreign patent No. WO00/74741 A2, international filing date, Jun. 8, 2000, one page.

Schaffer, D.J. et al, English abstract only of foreign patent No. WO00/74741 A3, international filing date, Jun. 8, 2000, one page.

Cherubine, P. et al, English abstract only of Autologous chondrocyte implantation using a bilayer collagen membrane: a preliminary report, J. Orthop Surg (Hong)Kong), 3002, pp. 10-15, vol. 11, No. 1.

Yamamoto, K, et al, English abstract only of Japanese publication No. 2006230749A, publication date Sep. 7, 2006, one page.

Verwerd, C.D.A. et al, Wound Healing of Autologous Implants in the Nasal Septal Cartilage, ORL, 1991, pp. 310-314, vol. 53.

Wilflingseder, P., Cancellous Bone Grafts, S Afr Med J., 1957, pp. 1267-1271, vol. 31, No. 50.

Wilfingseder, P., Treatment of Mandibular Facial Dysostosis, S Afr Med J., 1957, pp. 1296-1298, vol. 31, No. 51.

Hunter, W., VI. Of the Structure and Difeafes of Articulating Cartilages, Academiae Grypeswaldensis Bibliotheca, 1775, pp. 514-521, vol. 1.

Mannhelm, A., Abstract-Free Autoplastic Cartilage Transplantation, J. Am Med Assoc., 1926, pp. 2132, vol. 87, No. 25.

Williamson, A.K., et al, Compressive properties and function composition relationships of developing bovine articular cartilage, J. Orthopaedic Research, 2001, pp. 1113-1121, vol. 19.

Specchia, N. et al, Fetal chondral homografts in the repair of articular cartilage defects, Bulletin Hospital for Joint Diseases, 1996, pp. 230-235, vol. 54, No. 4.

Brown, K.R. et al, English Abstract of Japanese publication No. 2003-102755, 1 page.

Cheung, H.S. and Haak, M.H., Growth of osteoblasts on porous calcium phosphate ceramic: an in vitro model for biocompatibility study, Biomaterials, 1989, pp. 63-67., vol. 10.

Lapchinsky, A.G., et al., English abstract only of Apparatus for grinding cartilage in plastic surgery, 1960, primenenija Moskva, pp. 209-213, No. 4.

Imbert, L. et al, English translated Abstract only of Research on cartilage grafts hetero-plastic, 1916, Rev. de chir., pp. 111-128, vol. 52.

Iwamoto, Y. et al, English abstract of WO2005/011765, published Feb. 10, 2005, 1 page.

Ochi, M. et al, English abstract of Japanese publication No. 2002-233567, 1 page.

Sengupta, S. and Lumpur, K, The fate of transplants of articular cartilage in the rabbit, 1974, JBJS, pp. 167-177, vol. 56B, No. 1.

Didier R., English translated Abstract only of the production of cartilage and bone grafts in living and dead rabbits, 1928, Compt. rend. Soc de biol, pp. 443-445, vol. 98.

Pirsig, W., English Abstract only of Regeneration of septal cartilage in children after septoplasty. A histological study, Acta Otolaryngol, 1975, pp. 451-459, vol. 79, No. 5-6.

Passl, R. et al, Homologous articular cartilage transplantation in animal experiments. Preliminary studies on sheep (author's transl), Arch Orthop Unfallchir., 1976, pp. 243-256, vol. 86, No. 2.

Wikipedia print out of website—http://en.wikipedia.org/wiki/Alpha-2-Macroglobulin, 8 pages.

Kallio, K.E., Arthroplastia Cutanea, Discussion by T. Heirtom, ACTA Orhtopaedica Scandinavica, 1957, pp. 327-328, vol. 26.

Peer, L.A., Transplanation of Tissues—Cartilage, Bone, Fascia, Tendon, and Muscle, The Williams & Wilkins Company, 1955, pp. 69-137 and 392-393, vol. 1, Baltimore, Maryland, USA.

Mannhelm, A., Abstract—Free Autoplastic Cartilage Transplantation, J. Am Med Assoc., 1926, pp. 2132, vol. 87, No. 25.

Nehrer, S. and Minas, T., Treatment of Articular Cartilage Defects, Investigative Radiology, 2000, pp. 639-646, vol. 35, No. 10.

Prudden, T.M., Experimental studies on the transplantation of cartilage, Am. J. M. Sc., 1881, pp. 360-370, vol. 82.

Shands, A.R., Jr., The regeneration of hyaline cartilage in joints. An experimental study, Arch. Surg., 1931, pp. 137-178, vol. 22.

Cheung, H.S. and Haak, M.H., Growth of osteoblasts on porous calcium phosphate ceramic: an in vitro model for biocompatibility study, Biomaterials, 1989, pp. 63-67, vol. 10.

Sittinger, M. et al, Engineering of cartilage tissue using bioresorbable polymer carriers in perfusion culture, Biomaterials, 1994, pp. 451-456, vol. 15, No. 6.

Polettini, B., English abstract only Experimental Grafts of Cartilage and Bone, J.A.M.A., 1923, p. 360, vol. 80.

Braun, A and Heine, W.D., Abstract of The Use of Fibrin Adhesive in Fixation of Osteochondral Fragments, Year unknown, Canadian Orthopaedic Research Society, pp. 215-216.

Rohrbach, JM et al, Abstract only of Biological corneal replacement an alternative to keratoplasty and keratoprosthesis? A pilot study with heterologous hyaline cartilage in the rabbit model, 1995, Klin Monatsbl. Augenheilkd., pp. 191-196, vol. 207, No. 3.

Fontana, A et al, Abstract only of Cartilage chips synthesized with fibrin glue in rhinoplasty, Aestetic Plast Surg, 1991, pp. 237-240, vol. 15, No. 3.

Mainil-Varlet, P et al, Abstract only of Articular cartilage repair using a tissue engineered cartilage like implant: an animal study, Osteoarthritis Cartilage, 2001, pp. s:6-s:15, vol. 9.

Erol, OO, The Turkish delight: a pliable graft for rhinoplasty, Plast Reconstro Surg, 2000, pp. 2229-2241, vol. 105, No. 6.

Degroot, J. et al, Age related decrease in Proteoglycan synthesis of human articular chondrocytes, 1999, Arthritis & Rheumatism, pp. 1003-1009, vol. 42, No. 5.

Feder, J. et al, The promise of chondral repair using neocartilage, 2004, Tissue engineering in musculoskeletal clinical practice, 1st Edition, American Academy of Orthopaedic Surgeons, pp. 219-226, Chapter 22, Section 3.

Morales, T.I., Review: Chondrocyte moves: clever strategies?, Osteoarthritis and Cartilage, 2007, pp. 861-871, vol. 15.

Namba, R.S. et al, Spontaneous repair of superficial defects in articular cartilage in a fetal lamb model, 1998, JBJS, pp. 4-10, vol. 80, No. 1.

Aston, J.E. and Bently, G., Repair of articular surfaces by allografts of articular and growth-plate cartilage, Journal of Bone and Joint Surgery, 1986, pp. 29-35, vol. 68-B, No. 1.

Bacsich, P. and Wyburn, G.M., XXXVIII.—The Significance of the Mucoprotein Content on the Survival of Homografts of Cartilage and Cornea, Mucoprotein Content on the Survival of Homografts of Cartilage and Cornea, Dec. 19, 1947, pp. 321-330, vol. LXII.

Bentley, G. and Greer, III R.B., Homotransplantation of Isolated Epiphyseal and Articular Cartilage Chondrocytes into Joint Surfaces of Rabbits, Nature, 1971, pp. 385-388, vol. 230.

Brighton, C.T. et al, Articular Cartilage Preservation and Storage I. Application of Tissue Culture Techniques to the Storage of Viable Articular Cartilage, Arthritis and Rheumatism, 1979, pp. 1093-1101, vol. 22, No. 10.

Buckwalter, J.A., Articular Cartilage Injuries, Clinical Orthopaedics and Related Research, 2002, pp. 21-37, No. 402.

Bujia, J. et al, Culture and Cryopreservation of Chondrocytes from Human Cartilage: Relevance for Cartilage Allografting in Otolaryngology, ORL, 1992, pp. 80-84, vol. 54.

(56) References Cited

OTHER PUBLICATIONS

Chen, F.S. et al, Repair of Articular Cartilage Defects: Part II. Treatment Options, Am. J. Ortho., 1999, pp. 88-96.
Cherubino, P. et al, Autologous chondrocyte implantation using a bilayer collagen membrane: A preliminary report, J. Orthopaedic Surgery, 2003, pp. 10-15, vol. 11, No. 1.
Craigmyle, M.B.L., Studies of Cartilage Autografts and Homografts in the Rabbit, British J. Plastic Surgery, 1955, pp. 93-100.
Dupertuis, S.M., Actual Growth of Young Cartilage Transplants in Rabbits, Achives of Surgery, 1941, pp. 32-63, vol. 43.
Gibson, T. et al, The Long-Term Survival of Cartilage Homografts in Man, British Journal of Plastic Surgery, 1958, pp. 177-187.
He, Q. et al, Repair of flexor tendon defects of rabbit with tissue engineering method, Chinese J. of Traumatology, 2002, pp. 200-208, vol. 5, No. 4.
Jin, C.Z. et al, Human Amniotic Membrane as a Delivery Matrix for Articular Cartilage Repair, Tissue Engineering, 2007, pp. 693-703, vol. 13, No. 4.
Kon, E. et al, Second Generation Issues in Cartilage Repair, Sports Med Arthorosc Rev., 2008, pp. 221-229, vol. 16, No. 4.
Loeb, L., Autotransplantation and homoiotransplantation of cartilage in the guinea-pig, Am. J. Pathology, 1926, pp. 111-122, vol. II.
Mankin, H. J., Localization of Tritiated Thymidine in Articular Cartilage of Rabbits: II. Repair in Immature Cartilage, JBJS, 1962, pp. 688-698, vol. 44.
Mankin, H. J., Localization of Tritiated Thymidine in Articular Cartilage of Rabbits: III. Mature Articular Cartilage, JBJS, 1963, pp. 529-540, vol. 45.
Marcacci, M. et al, Articular Cartilage Engineering with Hyalograft C, Clinical Orthopaedics and Related Research, 2005, pp. 96-105, vol. 435.
Mcdermott, A.G.P. et al, Fresh Small-Fragment Osteochondral Allografts, Clin Ortho Rel Res, 1985, pp. 96-102, No. 197.
McKibbin, B., Immature Joint Cartilage and the Homograft Reaction, JBJS, 1971, pp. 123-135, vol. 53-B, No. 1.
Nixon, A.J. et al, Isolation, propagation, and cryopreservation of equine articular chondrocytes, Am J Vet Res, 1992, pp. 2364-2370, vol. 53, No. 12.
Nixon, A.J. and Fortier, L.A., New Horizons in Articular Cartilage Repair, AAEP Proceedings, 2001, pp. 217-226, vol. 47.
Peretti, G.M. et al, Bonding of Cartilage Matrices with Cultured Chondrocytes: An Experimental Model, J. Orthop Res., 1998, pp. 89-95, vol. 16.
Peretti, G.M. et al, Biomechanical Analysis of a Chondrocyte-Based Repair Model of Articular Cartilage, Tissue Engineering, 1999, pp. 317-326, vol. 5, No. 4.
Peretti, G.M. et al, Cell-based bonding of articular cartilage: An extended study, Wiley Periodicals, Inc. 2003, pp. 517-524.
Peretti, G.M. et al, In vitro bonding of pre-seeded chondrocytes, Sport Sci Health, 2007, pp. 29-33, vol. 2.
Robinson, D. et al, Regenerating Hyaline Cartilage in Articular Defects of Old Chickens Using Implants of Embryonal Chick Chondrocytes Embedded in a New Natural Delivery Substance, Calcif Tissue Int., 1990, pp. 246-253, vol. 46.
Schwan, B.L., Human Amniotic Membrane Transplantation for the Treatment of Ocular Surface Disease, http://www.dcmsonline.org/jax-medicine/2002journals/augsept2002/amniotic.htm, 2002, 7 pages.
Silverman, R.P. et al, Injectable Tissue-Engineered Cartilage Using a Fibrin Glue Polymer, American Society of Plastic Surgery, 1999, pp. 1809-1818, vol. 103, No. 7.
Tuan, R.S., A second-generation autologous chondrocyte implantation approach to the treatment of focal articular cartilage defects, Arthritis Research & Therapy, 2007, pp. 109-112, vol. 9.
Xu, J.W. et al, Injectable Tissue-Engineered Cartilage with Different Chondrocyte Sources, Plastic and Reconstructive Surgery, 2004, pp. 1361-1371, vol. 113, No. 5.
Zalzal, G.H. et al, Cartilage Grafts-Present Status, Head & Neck Surgery, 1986, pp. 363-374.

Ishizaki, Y. et al, Autocrine Signals Enable Chondrocytes to Survive in Culture, J. Cell Biol, 1994, pp. 1069-1077, vol. 126, No. 4.
Lu, Y. et al, Minced Cartilage without Cell Culture Serves as an Effective Intraoperative Cell Source for Cartilage Repair, J. Orthop Res, 2006, pp. 1261-1270, vol. 24, No. 6.
Non-Final Office Action regarding U.S. Appl. No. 11/010,779 issued Apr. 15, 2009, 10 pages.
Non-Final Office Action regarding U.S. Appl. No. 11/010,779 issued Feb. 17, 2010, 4 pages.
European Search Report regarding European Application No. 11154746 dated May 10, 2001, 2 pages.
European Search Report regarding European Application No. 11154748 dated May 10, 2001, 2 pages.
European Search Report regarding European Application No. 11154747 dated May 22, 2001, 2 pages.
Passl, R. and Plenk, H. Jr, Histological observations after replantation of articular cartilage, Unfallchirurgie, 1986, pp. 194-199, vol. 12, No. 4.
Passl, R. and Plenk, H. Jr, Fibrin Sealing of Cartilage Surfaces, Beitr. Orthop. Traumatol, 1989, pp. 503-507, vol. 36, No. 10.
Pech, A., et al, Tissuecol in Septorhinoplasties, Ann. Oto-Laryng., 1988, pp. 629-634, vol. 105.
Peer, L.A., Extended Use of Diced Cartilage Grafts, Meeting of the American Association of Plastic Surgeons, Apr. 21, 23, 1954, pp. 178-185.
Peer, L.A., The Fate of Living and Dead Cartilage Transplanted in Humans, Surg, Gynec, and Obst., 1939, pp. 603-610, vol. 68.
Peer, L.A., Fate of Autogenous Septal Cartilage After Transplantation in Human Tissues, Archv of Otolaryngology, 1941, pp. 696-709, vol. 34, No. 4.
Peer, L.A., The Neglected Septal Cartilage Graft (With Experimental Observations on the Growth of Human Cartilage Grafts), Arch Otolaryngol Head Neck Surg.,1945, pp. 384-396, vol. 42, No. 5.
Peretti, G.M. et al, Bonding of Cartilage Matrices with Cultured Chondrocytes: An Experimental Model, J. Orthopaedic Res, 1998, pp. 89-95, vol. 16.
Peretti, G.M. et al, Cell-Based Tissue-Engineered Allogeneic Implant for Cartilage Repair, Tissue Engineering, 2000, pp. 567-576, vol. 6, No. 5.
Peretti, G.M. et al, Cell-Based bonding of articular cartilage: An extended Study, J. Biomed Mater Res, 2003, pp. 517-524, vol. 64A.
Phemister, D.B. and Miller, E.M., The Method of New Joint Formation in Arthroplasty, Surgery, Gynecology and Ostetrics, 1918, pp. 406-447, vol. 26.
Pierce, G.W. and O'Connor, G.B., XXXVI. Reconstruction Surgery of the Nose, Ann. Otol. Rhin. and Laryng., 1938, pp. 437-452, vol. 47.
Piragine, F. et al, Use of Bovine Heterologous Cartilage and Fibrin Sealant in Middle Ear Reconstructive Surgery, Neurosurgery Ophthalmic Surgery ENT, Fibrin Sealing in Surgical and Nonsurgical Fields, 1994, pp. 193-198, vol. 5, Springer-Verlag, New York, USA.
Pitman, M.I. et al, The Use of Adhesives in Chondrocyte Transplantation Surgery: In-Vivo Studies, Bull Hosp Jt Dis Orthop Inst., 1989, pp. 213-220, vol. 49, No. 2.
Plaga, B.R. et al, Fixation of osteochondral fractures in rabbit knees. A comparison of Kirschner wires, fibrin sealant, and polydioxanone pins, J Bone Joint Surg Br., 1992, pp. 292-296, vol. 74, No. 2.
Plenk, H. Jr and Passl, R., Trans- and Replantation of Articular Cartilage Using the Fibrinogen Adhesive System, Gastpar, H. (ed.): Biology of the articular cartilage in health and disease, 1980, pp. 439-447, Schattauer, Stuttgart-New York, USA.
Plenk, H. Jr and Passl, R., Articular Cartilage Transplants in Experiments and Clinical Practice, ACA, Acta Chirurgica Austriaca 21st Seminar of the Austrian Association of Surgical Research, Nov. 13 to 15, 1997, pp. 1-4, vol. 29, Suppl. No. 137.
Pridie, K.H., A method of resurfacing osteoarthritic knee joints, JBJS, 1959, pp. 618-619, vol. 41B, No. 3.
Prin, A. et al, Effect of purified growth factors on rabbit articular chondrocytes in Monolayer Culture, I. DNA Synthesis, Arthritis & Rheumatism, 1982, pp. 1217-1227, vol. 25, No. 10.
Prudden, T., Article IV. Experimental Studies on the Transplantation, American Journal of the Medical Sciences: Oct. 1881, pp. 360-370, vol. 82, No. 164.

(56) References Cited

OTHER PUBLICATIONS

Vachon, A., et al, Neochondrogenesis in free intra-articular, periosteal, and perichondrial autografts in horses, Am J Vet Res, 1989, pp. 1787-1794, vol. 50, No. 10.
Redl, H. et al, Methods of Fibrin Seal Application, Thorac. Cardiovasc. Surgeon, 1982, pp. 223-227, vol. 30.
Roberts, S. et al, Autologous chondrocyte implantation for cartilage repair: monitoring its success by magnetic resonance imaging and histology, Arthritis Res and Therapy, 2003, pp. R60-R73, vol. 5.
Robinson, D. et al, Regenerating hyaline cartilage in articular defects of old chickens using implants of embryonal chick chondrocytes embedded in a new natural delivery substance, Calcif Tissue Int., 1990, pp. 246-253, vol. 46, No. 4.
Ruano-Ravina, A. and Diaz, M.J., Autologous chondrocyte implantation: a systematic review, Osteoarthritis and Cartilage, 2006, pp. 47-51, vol. 14.
Rudderman, R.H., et al, The Fate of Fresh and Preserved, Noncrushed and Crushed Autogenous Cartilage in the Rabbit Model, Ann Plast Surg, 1994, pp. 250-254, vol. 32.
Rupp, G. et al, Fibrin Adhesion of Transposed Autologous Cartilage Bone Grafts to Repair Knee-Joint Defects, Langenbeck's Archives of Surgery, 1978, pp. 676-677, vol. 347, No. 1.
Saidi, K. et al, Articular Knee Transplant in the Rabbit: Experimental Study and Clinical Projections, Union Medicale du Canada, 1971, pp. 88-99, vol. 100, No. 1.
Salter, R.B., et al, The Biological Effect of Continuous Passive Motion on the Healing of Full-Thickness Defects in ARticular Cartilage, JBJS, 1980, pp. 1232-1251, vol. 62-A, No. 8.
Sampath, T.K., et al, In vitro transformation of mesenchymal cells derived from embryonic muscle into cartilage in response to extracellular matrix components of bone, Proc Natl Acad Sci U S A, 1984, pp. 3419-3423, vol. 81, No. 11.
Schlag, G. and Redl, H., Fibrin Sealant in Orthopedic Surgery, Clin Ortho Rel Res, 1988, pp. 269-285, vol. 227.
Schlag, G. and Redl, H., Fibrin adhesive system in bone healing, Acta Orthop Scand., 1983, pp. 655-658, vol. 54, No. 4.
Schobel, H., Compound Prosthesis and Cartilage Layer: Two New Applications of Fibrin Sealing in Reconstructive Middle Ear Surgery, Neurosurgery Ophthalmic Surgery Ent, Fibrin Sealing in Surgical and Nonsurgical Fields, 1994, pp. 186-192, vol. 5, Springer-Verlag, New York, USA.
Schreiber, R.E. et al, A Method for Tissue Engineering of Cartilage by Cell Seeding on Bioresorbable Scaffolds, Ann N Y Acad Sci., 1999, pp. 398-404, vol. 875.
Schwam, B.L., Human Amniotic Membrane Transplantation for the Treatment of Ocular Surface Disease, Northeast Florida Medicine Journal, http://www.dcmsonline.org/jax-medicine/2002journals/augsept2002/amniotic.htm, 2002, print date Mar. 3, 2009, pp. 1-7.
Schwartz, E.R., et al, Sulfate Metabolism in Human Chondrocyte Cultures, J. Clin Investigation, 1974, pp. 1056-1063, vol. 54.
Schwarz, N., et al, The Influence of Fibrin Sealant on Demineralized Bone Matrix-Dependent Osteoinduction, Clin Ortho Rel Re, 1989, pp. 282-287, No. 238.
Shoemaker, S. et al, Effects of fibrin sealant on incorporation of autograft and xenograft tendons within bone tunnels. A preliminary study, JAm J Sports Med., 1989, pp. 318-324, vol. 17, No. 3.
Silverman, R.P., et al, Injectable Tissue-Engineered Cartilage Using a Fibrin Glue Polymer, American Society of Plastic Surgeons, 1999, pp. 1809-1818, vol. 103, No. 7.
Simms, G.F., et al, Diced Homologous Cartilage in Hernioplasty, Jour. Med. Soc. J.J., 1952, pp. 406-407, vol. 49, No. 9.
Sosna, A. and Vavra, J., Use of Fibrin Glue in Orthopedics, Acta Chir. Orthop. Traum., 1984, pp. 8-91, vol. 51, No. 2.
Specchia, N. et al, Fetal chondral homografts in the repair of articular cartilage defects, Blletin Hospital for Joint Diseases, 1996, pp. 230-235, vol. 54, No. 4.
Stoksted, P. and Ladefoged, C., Crushed cartilage in nasal reconstruction, J. Laryngology and Otology, 1986, pp. 897-906, vol. 100.
Tanaka, H. et al, A Study on Experimental Homocartilage Transplantation, Arch Orthop Traumat Surg, 1980, pp. 165-169, vol. 96.

Tanaka, H. and Shinno, N., Histochemical Studies on Regeneration of Articular Cartilage, Tokushima J Exp Med., 1971, pp. 63-73, vol. 18.
Temenoff, J.S. and Mikos, A.G., Review: Tissue engineering for regeneration of articular cartilage, Biomaterials, 2000, pp. 431-440, vol. 21, No. 5.
Tuan, R.S., A second-generation autologous chondrocyte implantation approach to the treatment of focal articular cartilage defects, Arthritis Res Ther., 2007, pp. 109 (1-4), vol. 9, No. 5.
Peretti, G.M. et al, A Biomechanical Analysis of an Engineered Cell-Scaffold Implant for Cartilage Repair, 2001, Ann Plast Surg, pp. 533-537, vol. 46.
"U.S. Appl. No. 12/101,553, Response filed Mar. 13, 2013 to Final Office Action mailed Dec. 28, 2012", 15 pgs.
"U.S. Appl. No. 12/861,404, Response filed Apr. 1, 2013 to Non Final Office Action mailed May 16, 2012", 6 pgs.
"U.S. Appl. No. 12/976,689, Response filed Apr. 1, 2013 to Non Final Office Action mailed May 17, 2012", 7 pgs.
"U.S. Appl. No. 13/428,873, Notice of Allowance mailed Mar. 25, 2013", 6 pgs.
"English translation of Abstract for CA2285382", (Oct. 15, 1998), 1 pg.
"English translation of Abstract of AU7100398", (Oct. 30, 1998), 1 pg.
"English translation of Abstract of JP 2006230749", (Feb. 25, 2005), 1 pg.
"English translation of Abstract of JP2001519700", (Oct. 23, 2001), 1 pg.
"European Application Serial No. 04813849.9, Office Action mailed Jun. 10, 2011", 3 pgs.
"European Application Serial No. 04813849.9, Office Action mailed Jul. 21, 2006", 2 pgs.
"European Application Serial No. 04813849.9, Office Action mailed Dec. 30, 2010", 4 pgs.
"European Application Serial No. 04813849.9, Response filed Aug. 21, 2006 to Office Action mailed Jul. 21, 2006", 4 pgs.
"European Application Serial No. 11154746.9, Office Action mailed Jan. 7, 2013", 3 pgs.
"European Application Serial No. 11154746.9, Office Action mailed Mar. 5, 2012", 33 pgs.
"European Application Serial No. 11154746.9, Office Action mailed Nov. 15, 2012", 1 pg.
"European Application Serial No. 11154746.9, Response filed Jul. 5, 2012 to Office Action mailed Mar. 5, 2012", 7 pgs.
"European Application Serial No. 11154747.7, Office Action mailed Mar. 5, 2012", 4 pgs.
"European Application Serial No. 11154747.7, Office Action mailed Jul. 23, 2012", 3 pgs.
"European Application Serial No. 11154747.7, Office Action mailed Nov. 21, 2012", 4 pgs.
"European Application Serial No. 11154747.7, Response filed Jun. 25, 2012 to Office Action mailed Mar. 5, 2012", 8 pgs.
"European Application Serial No. 11154747.7, Response filed Sep. 5, 2012 to Office Action mailed Jul. 23, 2012", 3 pgs.
"European Application Serial No. 11154747.7, Response filed Dec. 13, 2011 to Extended European Search Report mailed May 23, 2011", 3 pgs.
"European Application Serial No. 11154748.5, Office Action mailed Apr. 13, 2012", 5 pgs.
"Japanese Application Serial No. 2008-528250, Office Action mailed Mar. 5, 2013", 3 pgs.
"U.S. Appl. No. 12/063,291, Notice of Allowance mailed Mar. 4, 2013", 7 pgs.
"U.S. Appl. No. 13/327,265, Final Office Action mailed Jan. 31, 2013", 8 pgs.
"U.S. Appl. No. 13/327,286, Non Final Office Action mailed Feb. 7, 2013", 9 pgs.
"U.S. Appl. No. 13/428,873, Response filed Feb. 12, 2013 to Final Office Action mailed Dec. 12, 2012", 6 pgs.
"International Application Serial No. PCT/US08/60078, International Search Report mailed Sep. 3, 2008", 3 pgs.
Adibi, Siamak A, et al., "Removal of Glycylglutamine from Plasma by Individual Tissues: Mechanism and Impact on Amino Acid Fluxes

(56) References Cited

OTHER PUBLICATIONS in Postabsorption and Starvation", The Journal of Nutrition, Symposium: Nutritional and Hormonal Regulation of Amino Acid Metabolism, (1993), 325-331.

Brighton, Carl T, et al., "In Vitro Rabbit Articular Cartilage Organ Model II. 35S Incorporation in Various Oxygen Tensions", Arthritis and Rheumatism vol. 17, No. 3, (May 1974), 245-252.

Butler, M, et al., "Nutritional aspects of the growth of animal cells in culture", Journal of Biotechnology 12, (1989), 97-110.

Butler, Michael, et al., "Adaptation of mammalian cells to non-ammoniagenic media", Cytotechnology 15, (1994), 87-94.

Chesterman, P. J., et al., "Cartilage as a Homograft", The Journal of Bone and Joint Surgery. Proceedings and reports of councils and associations, (1968), 878.

Christie, A, et al., "Glutamine-based dipeptides are unilized in mammalian cell culture by extracellular hydrolysis catalyzed by a specific peptidase", Journal of Biotechnology 37, (1994), 277-290.

Frisbie, David D, et al., "In Vivo Evaluation of Autologous Cartilage Fragment-Loaded Scaffolds Implanted Into Equine Articular Defects and Compared With Autologous Chondrocyte Implantation", The American Journal of Sports Medicine 37, (Nov. 24, 2009), 71S-80S.

Glacken, Michael W, "Catabolic Control of Mammalian Cell Culture", Biotechnology vol. 6, (Sep. 1998), 1041-1050.

Hammarqvist, Folke, et al., "Alanyl-glutamine Counteracts the Depletion of Free Glutamine and the Postoperative Decline in Protein Synthesis in Skeletal Muscle", Ann. Surg, (Nov. 1990), 637-644.

Hassell, T, et al., "Growth Inhibition in Animal Cell Culture: The Effect of Lactate and Ammonia", Applied Biochemistry and Biotechnology, vol. 30, (1991), 29-41.

McCormick, F., "Minced Articular Cartilage—Basic Science, Surgical Technique, and Clinical Application", Sports Med. Arthrosc. Rev., vol. 16, No. 4, (Dec. 2008), 217-220.

McIlwraith, C W, et al., "In-Vivo Evaluation of a One-Step Autologous Cartilage Resurfacing Technique (CAIS)—Comparison of Three Different Scaffolds", 6th Symposium of the International Cartilage Repair Society, (Jan. 2006), p. 3-6.

Minamoto, Yoshiki, et al., "Development of a serum-free and heat-sterilizable medium and continuous high-density cell culture", Cytotechnology, vol. 5, (1991), S35-S51.

Newland, M, et al., "Hybridoma growth limitations: The roles of energy metabolism and ammonia production", Cytotechnology, vol. 3, (1990), 215-229.

Reitzer, Lawrence J, et al., "Evidence that Glutamine, Not Sugar, is the Major Energy Source for Cultured HeLa Cells", The Journal of Biological Chemistry, vol. 254, No. 8, (Apr. 1979), 2669-2676.

Roth, E, et al., "Influence of Two Glutamine-Containing Dipeptides on Growth of Mammalian Cells", In Vitro Cellular & Developmental Biology, vol. 24, No. 7, (Jul. 1988), 696-698.

Zielke, Ronald H, et al., "Glutamine: a major energy source for mammalian cells", Federation Proceedings, vol. 43, No. 1, (Jan. 1984), 121-125.

"U.S. Appl. No. 10/374,772, 1.132 Declaration of Julia Hwang filed Jan. 5, 2009", 3 pgs.

"U.S. Appl. No. 10/374,772, Response filed Jan. 6, 2009 to Non-Final Office Action mailed Sep. 2, 2008", 5 pgs.

"U.S. Appl. No. 10/874,402, Final Office Action mailed Feb. 22, 2011", 10 pgs.

"U.S. Appl. No. 10/874,402, Final Office Action mailed Apr. 17, 2009", 17 pgs.

"U.S. Appl. No. 10/874,402, Final Office Action mailed Apr. 19, 2010", 13 pgs.

"U.S. Appl. No. 10/874,402, Non Final Office Action mailed Apr. 10, 2008", 9 pgs.

"U.S. Appl. No. 10/874,402, Non Final Office Action mailed Sep. 22, 2010", 11 pgs.

"U.S. Appl. No. 10/874,402, Non Final Office Action mailed Oct. 27, 2009", 15 pgs.

"U.S. Appl. No. 11/010,779, Examiner Interview Summary mailed Apr. 5, 2010", 4 pgs.

"U.S. Appl. No. 11/010,779, Examiner Interview Summary mailed Dec. 7, 2009", 3 pgs.

"U.S. Appl. No. 11/010,779, Non Final Office Action mailed Feb. 17, 2010", 4 pgs.

"U.S. Appl. No. 11/010,779, Non Final Office Action mailed Apr. 15, 2009", 8 pgs.

"U.S. Appl. No. 11/010,779, Notice of Allowance mailed Jul. 8, 2010", 4 pgs.

"U.S. Appl. No. 11/010,779, Response filed Feb. 12, 2009 to Restriction Requirement mailed Jan. 12, 2009", 3 pgs.

"U.S. Appl. No. 11/010,779, Response filed Apr. 19, 2010 to Non Final Office Action mailed Feb. 17, 2010", 13 pgs.

"U.S. Appl. No. 11/010,779, Response filed Jul. 15, 2009 to Non Final Office Action mailed Apr. 15, 2009", 16 pgs.

"U.S. Appl. No. 11/010,779, Response filed Dec. 3, 2009 to Non Final Office Action mailed Apr. 15, 2009", 13 pgs.

"U.S. Appl. No. 11/010,779, Restriction Requirement mailed Jan. 12, 2009", 16 pgs.

"U.S. Appl. No. 11/413,419, Final Office Action mailed Aug. 25, 2009", 13 pgs.

"U.S. Appl. No. 11/413,419, Non Final Office Action mailed Jun. 26, 2008", 12 pgs.

"U.S. Appl. No. 11/613,250, Advisory Action mailed Jul. 9, 2008", 13 pgs.

"U.S. Appl. No. 11/613,250, Final Office Action mailed Apr. 15, 2008", 9 pgs.

"U.S. Appl. No. 11/613,250, Non Final Office Action mailed Mar. 28, 2011", 9 pgs.

"U.S. Appl. No. 11/613,250, Non Final Office Action mailed May 28, 2009", 12 pgs.

"U.S. Appl. No. 11/613,250, Non Final Office Action mailed Sep. 20, 2007", 17 pgs.

"U.S. Appl. No. 11/613,250, Non Final Office Action mailed Sep. 21, 2010", 15 pgs.

"U.S. Appl. No. 11/613,250, Non Final Office Action mailed Oct. 16, 2008", 11 pgs.

"U.S. Appl. No. 11/613,250, Non Final Office Action mailed Dec. 23, 2009", 15 pgs.

"U.S. Appl. No. 11/613,250, Notice of Allowance mailed Dec. 23, 2011", 9 pgs.

"U.S. Appl. No. 11/613,250, Response filed Jan. 16, 2009 to Non Final Office Action mailed Oct. 16, 2008", 9 pgs.

"U.S. Appl. No. 11/613,250, Response filed Jan. 19, 2011 to Non Final Office Action mailed Sep. 21, 2010", 13 pgs.

"U.S. Appl. No. 11/613,250, Response filed Mar. 23, 2010 to Non Final Office Action mailed Dec. 23, 2009", 9 pgs.

"U.S. Appl. No. 11/613,250, Response filed Jun. 16, 2008 to Final Office Action mailed Apr. 15, 2008", 19 pgs.

"U.S. Appl. No. 11/613,250, Response filed Aug. 28, 2009 to Non Final Office Action mailed May 28, 2009", 12 pgs.

"U.S. Appl. No. 11/613,250, Response filed Sep. 28, 2011 to Non Final Office Action mailed Mar. 28, 2011", 9 pgs.

"U.S. Appl. No. 11/613,250, Response filed Dec. 20, 2007 to Non Final Office Action mailed Sep. 20, 2007", 19 pgs.

"U.S. Appl. No. 11/613,319, Advisory Action mailed Jan. 19, 2010", 3 pgs.

"U.S. Appl. No. 11/613,319, Final Office Action mailed Jun. 18, 2012", 11 pgs.

"U.S. Appl. No. 11/613,319, Final Office Action mailed Oct. 26, 2009", 7 pgs.

"U.S. Appl. No. 11/613,310, Information Disclosure Statement mailed Mar. 20, 2007", 9 pgs.

"U.S. Appl. No. 11/613,310, Information Disclosure Statement mailed Jun. 30, 2008", 6 pgs.

"U.S. Appl. No. 11/613,310, Information Disclosure Statement mailed Sep. 3, 2010", 5 pgs.

"U.S. Appl. No. 11/613,310, Information Disclosure Statement mailed Dec. 20, 2007", 6 pgs.

"U.S. Appl. No. 11/613,319, Non Final Office Action mailed Mar. 13, 2009", 7 pgs.

"U.S. Appl. No. 11/613,319, Non Final Office Action mailed Dec. 29, 2011", 9 pgs.

(56) References Cited

OTHER PUBLICATIONS

"U.S. Appl. No. 11/613,319, Response filed Jan. 26, 2009 to Restriction Requirement mailed Dec. 26, 2008", 7 pgs.
"U.S. Appl. No. 11/613,319, Response filed Jan. 26, 2010 to Advisory Action mailed Jan. 19, 2010", 9 pgs.
"U.S. Appl. No. 11/613,319, Response filed Mar. 29, 2012 to Non Final Office Action mailed Dec. 29, 2011", 15 pgs.
"U.S. Appl. No. 11/613,319, Response filed Jun. 11, 2009 to Non Final Office Action mailed Mar. 13, 2009", 8 pgs.
"U.S. Appl. No. 11/613,319, Response filed Sep. 17, 2012 to Final Office Action mailed Jun. 18, 2012", 19 pgs.
"U.S. Appl. No. 11/613,319, Response filed Dec. 7, 2009 to Final Office Action mailed Oct. 26, 2009", 8 pgs.
"U.S. Appl. No. 11/613,319, Restriction Requirement mailed Dec. 26, 2008", 6 pgs.
"U.S. Appl. No. 11/613,456, Advisory Action mailed Aug. 11, 2009", 3 pgs.
"U.S. Appl. No. 11/613,456, Final Office Action mailed Jun. 4, 2009", 7 pgs.
"U.S. Appl. No. 11/613,456, Non Final Office Action mailed Jan. 23, 2009", 6 pgs.
"U.S. Appl. No. 11/613,456, Non Final Office Action mailed Sep. 11, 2009", 5 pgs.
"U.S. Appl. No. 11/613,456, Notice of Allowance mailed Jan. 19, 2010", 5 pgs.
"U.S. Appl. No. 11/613,456, Response filed Apr. 3, 2009 to Non Final Office Action mailed Jan. 23, 2009", 8 pgs.
"U.S. Appl. No. 11/613,456, Response filed Aug. 4, 2009 to Final Office Action mailed Jun. 4, 2009", 9 pgs.
"U.S. Appl. No. 11/613,456, Response filed Jan. 6, 2008 to Restriction Requirement mailed Oct. 7, 2008", 7 pgs.
"U.S. Appl. No. 11/613,456, Response filed Dec. 7, 2009 to Non Final Office Action mailed Sep. 11, 2009", 9 pgs.
"U.S. Appl. No. 11/613,456, Restriction Requirement mailed Oct. 7, 2008", 6 pgs.
"U.S. Appl. No. 12/063,291, Final Office Action mailed Mar. 15, 2012", 10 pgs.
"U.S. Appl. No. 12/063,291, Final Office Action mailed Mar. 22, 2011", 8 pgs.
"U.S. Appl. No. 12/063,291, Non Final Office Action mailed Sep. 15, 2010", 6 pgs.
"U.S. Appl. No. 12/063,291, Notice of Allowance mailed Aug. 8, 2012", 9 pgs.
"U.S. Appl. No. 12/063,291, Notice of Allowance mailed Oct. 11, 2012", 8 pgs.
"U.S. Appl. No. 12/063,291, Preliminary Amendment filed Feb. 8, 2008", 9 pgs.
"U.S. Appl. No. 12/063,291, Response filed Jan. 21, 2011 to Non Final Office Action mailed Sep. 15, 2010", 12 pgs.
"U.S. Appl. No. 12/063,291, Response filed Jul. 16, 2012 to Final Office Action mailed Mar. 15, 2012", 13 pgs.
"U.S. Appl. No. 12/063,291, Response filed Sep. 22, 2011 to Final Office Action mailed Mar. 22, 2011", 10 pgs.
"U.S. Appl. No. 12/101,553, Response filed Aug. 15, 2011 to Restriction Requirement mailed Jul. 13, 2011", 11 pgs.
"U.S. Appl. No. 12/101,553, Final Office Action mailed Sep. 14, 2012", 9 pgs.
"U.S. Appl. No. 12/101,553, Final Office Action mailed Dec. 28, 2012", 9 pgs.
"U.S. Appl. No. 12/101,553, Non Final Office Action mailed Nov. 9, 2011", 8 pgs.
"U.S. Appl. No. 12/101,553, Response filed May 9, 2012 to Non Final Office Action mailed Nov. 9, 2011", 14 pgs.
"U.S. Appl. No. 12/101,553, Restriction Requirement mailed Ju. 13, 2011", 17 pgs.
"U.S. Appl. No. 12/751,230, Non Final Office Action mailed Sep. 1, 2010", 9 pgs.
"U.S. Appl. No. 12/751,230, Preliminary Amendment filed Mar. 31, 2010", 7 pgs.
"U.S. Appl. No. 12/751,230, Response filed Jul. 30, 2010 to Restriction Requirement mailed Jul. 21, 2010", 5 pgs.
"U.S. Appl. No. 12/751,230, Restriction Requirement mailed Jul. 21, 2010", 53 pgs.
"U.S. Appl. No. 12/861,404, Non Final Office Action mailed May 16, 2012", 6 pgs.
"U.S. Appl. No. 12/861,404, Preliminary Amendment filed Aug. 23, 2010", 6 pgs.
"U.S. Appl. No. 12/976,689, Non Final Office Action mailed May 17, 2012", 7 pgs.
"U.S. Appl. No. 13/327,238, Non Final Office Action mailed Jan. 2, 2013", 8 pgs.
"U.S. Appl. No. 13/327,238, Preliminary Amendment filed Jun. 1, 2012", 6 pgs.
"U.S. Appl. No. 13/327,238, Response filed Dec. 7, 2012 to Restriction Requirement mailed Sep. 7, 2012", 6 pgs.
"U.S. Appl. No. 13/327,238, Restriction Requirement mailed Sep. 7, 2012", 11 pgs.
"U.S. Appl. No. 13/327,265, Non Final Office Action mailed Apr. 2, 2012", 10 pgs.
"U.S. Appl. No. 13/327,265, Response filed Sep. 4, 2012 to Non Final Office Action mailed Apr. 2, 2012", 7 pgs.
"U.S. Appl. No. 13/327,286, Preliminary Amendment filed Jun. 1, 2012", 7 pgs.
"U.S. Appl. No. 13/428,873 , Response filed Oct. 17, 2012 to Non Final Office Action mailed Jul. 18, 2012", 9 pgs.
"U.S. Appl. No. 13/428,873, Final Office Action mailed Dec. 12, 2012", 6 pgs.
"U.S. Appl. No. 13/428,873, Non Final Office Action mailed Jul. 18, 2012", 9 pgs.
"U.S. Appl. No. 13/428,873, Preliminary Amendment filed Mar. 23, 2012", 6 pgs.
"Application Serial No. 2008240191, First Examination Report mailed Sep. 21, 2012".
"Australian Application Serial No. 2006282754, Office Action mailed Nov. 8, 2011", 3 pgs.
"Combine", Merriam-Webster Online Dictionary, [Online] Retrieved From Internet: <http://www.merriam-webster.com/dictionary/combine>, (Jul. 13, 2011), 2 pgs.
"European Application Serial No. 04813849.9, Extended European Search Report mailed Apr. 8, 2008", 3 pgs.
"European Application Serial No. 04813849.9, Office Action mailed Feb. 16, 2009", 5 pgs.
"European Application Serial No. 04813849.9, Response filed Aug. 20, 2009 to Office Action mailed Feb. 16, 2009", 18 pgs.
"European Application Serial No. 07862720.5, Notice of Allowance mailed Feb. 25, 2011", 6 pgs.
"European Application Serial No. 07862720.5, Office Action mailed Feb. 26, 2010", 3 pgs.
"European Application Serial No. 07862720.5, Response filed Sep. 1, 2010 to Office Action mailed Feb. 26, 2010", 10 pgs.
"European Application Serial No. 11154746.9, Response filed Feb. 14, 2012 to Office Action mailed Nov. 15, 2012", 4 pgs.
"European Application Serial No. 11154746.9, Search Report mailed May 23, 2011", 4 pgs.
"European Application Serial No. 11154747.7, Response filed Dec. 14, 2012 to Office Action mailed Nov. 21, 2012", 4 pgs.
"European Application Serial No. 11154747.7, Search Report mailed May 23, 2011", 4 pgs.
"European Application Serial No. 11154748.5, Search Report mailed May 24, 2011", 4 pgs.
"International Application Serial No. PCT/US2008/60078, International Search Report mailed Sep. 3, 2008", 1 pg.
"International Application Serial No. PCT/US2004/041591, Written Opinion mailed Jun. 12, 2006", 4 pgs.
"International Application Serial No. PCT/US2006/33687, International Preliminary Report on Patentability mailed Feb. 26, 2008", 7 pgs.
"International Application Serial No. PCT/US2006/33687, Written Opinion mailed Aug. 8, 2007", 6 pgs.
"International Application Serial No. PCT/US2007/025252, International Preliminary Report on Patentability mailed Jun. 23, 2009", 8 pgs.

(56) References Cited

OTHER PUBLICATIONS

"International Application Serial No. PCT/US2007/025252, International Search Report mailed Apr. 18, 2008", 3 pgs.
"International Application Serial No. PCT/US2007/025252, Written Opinion mailed Apr. 18, 2008", 7 pgs.
"International Application Serial No. PCT/US2007/086468, International Preliminary Report on Patentability mailed Jun. 23, 2009", 10 pgs.
"International Application Serial No. PCT/US2007/086468, International Search Report Jun. 5, 2008", 4 pgs.
"International Application Serial No. PCT/US2007/086468, Written Opinion mailed Jun. 20, 2009", 9 pgs.
"Japanese Application Serial No. 2008-528250, Office Action mailed Jun. 22, 2012", 5 pgs.
"Japanese Application Serial No. 2008-528250, Response filed Nov. 22, 2012 to Office Action mailed Jun. 22, 2012", 9 pgs.
"Morsel", Merriam-Webster Online Dictionary, [Online] Retrieved From Internet: <http://www.merriam-webster.com/dictionary/morsel>, (Jul. 13, 2011), 2 pgs.
"Pulverize", Merriam-Webster Online Dictionary, [Online] Retrieved From Internet: <http://www.merriam-webster.com/dictionary/pulverize>, (Jul. 13, 2011), 2 pgs.
Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.
Akens, M K, et al., "In Vitro Studies of a Photo-oxidized Bovine Articular Cartlage", Journal of Veterinary Medicine, vol. 49, Blackwell Wissenschafts-Verlag, Berlin, (2002), 39-45.
Alfredson, Hakan, et al., "Superior results with continuous passive motion compared to active motion after periosteal transplantation", vol. 7, Knee Surg sports Trautnatol Arthrosc, Springer-Verlag, Germany, (1999), 232-238.
Alston, et al., "New method to prepare autologous fibrin glue on demand", Translational Research vol. 149, (2007), 187-195.
Augenstein, D C, et al., "Effect of Shear on the Death of Two Strains of Mammalian Tissue Cells", vol. XIII, Biotechnology and Bioengineering, USA, (1971), 409-418.
Aulthouse, Amy Lynn, et al., "Expression of the Human Chondrocyte Phenotype in Vitro", vol. 25, No. 7, In Vitro Cellular & Developmental Biology, USA, (1989), 659-668.
Azizkhan, et al., "Chondrocytes contain a growth factor that is localized in the nucleus and is associated with chomatin", Proc. Natl. Acad. Sci., vol. 77, No. 5, (1980), 2762-2766.
Bartlett, W, et al., "Autologous chondrocyte implantation at the knee using a bilayer collagen membrane with bone graft", vol. 87-B, The Journal of Bone & Joint Surgery [Br], London, (2005), 330-332.
Bartlett, W, et al., "Autologous chondrocyte implantation versus matrix-induced autologous chondrocyte implantation for osteochondral defects of the knee", vol. 87-B, No. 5, The Journal of Bone & Joint Surgery [Br], London, (2005), 640-645.
Bassleer, C, et al., "Human Chondrocytes in Tridimensional Culture", vol. 22, No. 3, Pl. I, In Vitro Cellular & Developmental Biology, UK, (1986), 113-119.
Behrens, Peter, et al., "Matrix-associated autologous chondrocyte trnasplantationlimplantation (MACTIMACI)—5-year follow-up", vol. 13, The Knee, Elsevier, UK, (2006), 194-202.
Ben-Zeev, A, et al., "Protein synthesis requires cell-surface contact while nuclear events respond to cell shape in anchorage-dependent fibroblasts", Cell, vol. 21., (1980), 365-372.
Binette, F, et al., "Tenninally Redifferentiated Human Articular Chondrocytes Express Hyaline Cartilage Markers without Hypertrophy", Genzyrne Tissue Repair, 43rd Annual Meeting, Orthopaedic Research Society, USA, (1997), 520 pgs.
Black, J., "Biological Performance of Tantalum", Clinical Materials, vol. 16., (1994), 167-173.
Bobyn, J D, et al., "Effect of pore size on the peel strength of attachment of fibrous tissue to porous-surfaced implants", J. Biomed. Mater. Res., vol. 16., (1982), 571-584.
Bobyn, JD, et al., "Characteristics of bone ingrowth and interface mechanics of a new porous tantalum biomaterial", J. Bone Joint Surg Br., 81, (1999), 907-914.
Bobyn, JD, et al., "Tissue response to porous tantalum acetabular cups", a canine model. J. Arthroplasty, 14, (1999), 347-54.
Boumediene, et al., "Modulation of rabbit articular chondrocyte (RAC) proliferation by TGF-B isoforms", Cell Prolif., vol. 28, (1995), 221-234.
Bujia, et al., "Synthesis of human cartilage using organotypic cell culture", ORL, vol. 55, (1993), 347-351.
Bujia, J, et al., "Effect of Growth Factors on Cell Proliferation by Human Nasal Septal Chondrocytes Cultured in Monolayer", Acta Otolaryngol, vol. 114, Scandinavian University Press, Sweden, (1994), 539-543.
Chang, et al., "Cartilage-Derived Morphogenetic Proteins", J. Biol. Chem., 269, (1994), 28227-28234.
Chawla, K, et al., "Short-term retention of labeled chondrocyte subpopulations in stratified tissue-engineered cartilaginous constructs implanted in vivo in mini-pigs", Tissue Engineering vol. 13, No. 7, (2007), 1525-1538.
Cherry, R S, et al., "Hydrodynamic effects on cells in agitated tissue culture reactors", Bioprocess Engineering, vol. I, Springer-Verlag, USA, (1986), 29-41.
Cherry, Robert S, et al., "Physical Mechanisms of Cell Damage in Microcarrier Cell Culture Bioreactors", Biotechnology and Bioengineering, vol. 32, John Wiley & Sons, Inc., USA, (1988), 1001-1014.
Cherry, Robert S, et al., "Understanding and Controlling Fluid-Mechanical Injury of Animal Cells in Bioreactors", Animal Cell Biotechnology, vol. 4, Academic Press Limited, USA, (1990), 71-121.
Choi, Ye Chin, et al., "Effect of Platelet Lysate on Growth and Sulfated Glycosaminoglycan Synthesis in Articular Chondrocyte Cultures", Arthritis and Rheumatism, vol. 22, No. 2, USA, (1980), 220-224.
Christel, P, et al., "Osteochondral Grafting using the Mosaicplasty Technique", [Online] Retrieved from the internet Dec. 16, 2008: <www.maitrise-orthop.com/corpusmaitri/orthopaedic/mo76_mosaicplasty/index.shtm>, 20 pgs.
Convery, F.R., et al., "The Repair of Large Osteochondral Defects", An Experimental Study in Horses, Clin. Orthrop. 82., (1972), 253-262.
Coutts, Richard D, et al., "Rib Periochondrial Autografts in Full-Thickness Articular Cartilage Defects in Rabbits", Clinic Orthopaedics and Related Research, No. 275, USA, (1989), 263-273.
Craigmyle, M B, "Studies of cartilage autografts and homografts in the rabbit", British Journal of Plastic Surgery 8, (1955), 93-100.
Croughan, Matthew Shane, et al., "Hydrodynamic Effects on Animal Cells Grown in Microcarrier Cultures", Biotechnology and Bioengineering, vol. XXIX, John Wiley & Sons, Inc., USA, (1987), 130-141.
Delbruck, Axel, et al., "In-Vitro Culture of Human Chondrocytes from Adult Subjects", Connective Tissue Research, Gordon and Breach, Science Publishers, Inc., USA, (1986), 155-172.
Dewey, Jr, C F, et al., "The Dynamic Response of Vascular Endothelial Cells to Fluid Shear Stress", Journal of Biomechnical Engineering, vol. 103, USA, (1981), 177-185.
Didier, R, et al., "The production of cartilage and bone grafts in living and dead rabbits", Compt. rend. Soc de bioi, vol. 98, (1928), 443-445.
Dogterom, A A, et al., "Matrix depletion of young and old human articular cartilage by cultured autologous synovium fragments; a chondrocyte-independent effect", Rheumatology International, vol. 5, Springer-Verlag, UK, (1985), 169-173.
Dowthwaite, Gary P, et al., "The surface of articular cartilage contains a progenitor cell population", Journal of Cell Science vol. 117, The Company of Biologists, 2004 UK, (2004), 889-897.
Drobnic, M. MD, et al., "Comparison of four techniques for the fixation of a collagen scaffold in the human cadaveric knee", Osteoarthritis and Cartilage, vol., 14 Elsevier Ltd., UK, (2006), 337-344.
Elima, Kati, et al., "Expression of mRNAs for collagens and other matrix components in dedifferentiating and redifferentiating human

(56) References Cited

OTHER PUBLICATIONS chondrocytes in culture", FEBS Letters, vol. 258 No. 2, Elsevier Science Publishers B.V. (Biomedical Division), UK, (1989), 195-198.
Evans, Robin C, et al., "Solute diffusivity correlates with mechanical properties and matrix density of compressed articular cartilage", Archives of Biochemistry and Biophysics, vol. 442, Elsevier, UK, (2005), 1-10.
Farmer, S R, et al., "Altered Translatability of Messenger RNA from Suspended Anchorage-Dependent Fibroblasts", Reversal upon Cell Attachment to a Surface, Cell, vol. 15., (1978), 627-637.
Feder, J, "Tissue Engineering in Musculoskeletal Clinical Practice: The Promise of Chondral Repair Using Neocartilage", Am. Acad. Orthop. Surg., Chapter 22., (2004), 219-226.
Feder, Joseph, et al., "The Large-Scale Cultivation of Mammalian Cells", Scientific American, Inc USA, (1983), 36-43.
Folkman, J, et al., "Role of cell shape in growth control", Nature, vol. 273., (1978), 345-349.
Frangos, John, et al., "Flow Effects on Prostacyclin Production by Cultured Human Endothelial Cells", Science, vol. 227, Texas, USA, (1985), 1477-1479.
Freed, L E, et al., "Neocartilage formation in virtro and invivo using cells cultured on synthetic biodegradable polymers", J. Biomed. Mater. Res. vol. 27 (1), (1993), 11-23.
Freed, L. E, et al., "Cartilage Tissue Engineering Based on Cell-Polymer Constructs", Tissue Engineering of Cartilage, CRC Press, Inc., USA, (1995), 1788-1806.
Freed, L. E, et al., "Composition of Cell-Polymer Cartilage Implants", Biotechnology and Bioengineering, vol. 43, John Wiley & Sons, Inc., USA, (1994), 605-614.
Freed, L. E, et al., "Cultivation of Cell-Polymer Cartilage Implants in Bioreactors", Journal of Cellular Biochemistry, vol. 51, Wiley-Liss, Inc., USA, (1993), 257-264.
Freed, L. E, et al., "Cultivation of Cell-Polymer Tissue Constructs in Simulated Microgravity", Biotechnology and Bioengineering, vol. 46, John Wiley & Sons, Inc., USA, (1995), 306-313.
Freed, Lisa E, et al., "Tissue engineering of cartilage in space", Proc. Natl. Acad. Sci., vol. 94, The National Academy of Sciences, USA, (1997), 13885-13890.
Fry, Donald, "Acutte Vascular Endothelial Changes Associated with Increased Blood Velocity Gradients,", Journal of the American Heart Association, vol. XXII, American Heart Association, USA, (1968), 165-197.
Fu?, M, et al., "Characteristics of human chondrocytes, osteoblasts and fibroblasts seeded onto a type I/II collagen sponge under different culture conditions", Annals of Anatomy, vol. 182, Urban & Fischer Verlag, Germany, (2000), 303-310.
Galera, et al., "Effect of transforming growth factor-B1 (TGF-B1) on matrix synthesis by monolayer cultures of rabbit chondrocytes during the dedifferentiating process", Experimental Cell Research, vol. 200, (1992), 379-392.
Gibble, et al., "Fibrin glue: the perfect operative sealant", Transfusion, 1990, vol. 30, No. 8., 741-747.
Gille, J, et al., "Migration pattern, morphology and viability of cells suspended in or sealed with fibrin glue: A histomorphologic study", Tissue and Cell, Vo. 37, Elsevier, UK, (2005), 339-348.
Girotto, Davide, et al., "Tissue-specific gene expression in chondrocytes grown on three-dimensional hyaluronic acid scaffolds", Biomaterials, vol. 24, Elsevier, UK, (2003), 3265-3275.
Gooch, K J, et al., "Effects of Mixing Intensity on Tissue-Engineered Cartilage", Biotechnology and Bioengineering, vol. 72, No. 4, John Wiley & Sons, Inc., USA, (2001), 402-407.
Guilak, F, et al., "Functional tissue engineering: the role of biomechanics in articular cartilage repair", Clin Orthop Relat Res, vol. 391S., (2001), 295-305.
Haart, et al., "Optimization of chondrocyte expansion in culture", Acta Orthop Scand, vol. 70, No. 1, (1999), 55-61.
Hacking, S A, et al., "Fibrous tissue ingrowth and attachment to porous tantalum", J. Biomed. Mater. Res., vol. 52, No. 4., (2000), 631-638.

Han, et al., "Scaffold-free Grafts for Articular Cartilage Defects", Clin Orthop Relat Res. vol. 466, (2008), 1912-1920.
Harrison, et al., "Osteogenin promotes reexpression of cartilage phenotype by dedifferentiated articular chondrocytes in serum-free medium", Experimental Cell Research, vol. 192, (1991), 340-345.
Harrison, et al., "Transforming growth factor-beta: Its effect on phenotype reexpression by dedifferentiated chondrocytes in the presence and absence of osteogenin", In Vitro Cell Dev. Biol., vol. 28A, (1992), 445-448.
Hiraki, et al., "Effect of transforming growth factor B on cell proliferation and glycosaminoglycen synthesis by rabbit growth-plate chondrocytes in culture", Biochimica et Biophysica Acta, vol. 969, (1988), 91-99.
Hollander, Anthony P, et al., "Maturation of Tissue Engineered Cartilage Implanted in Injured and Osteoarthritic Human Knees,", Tissue Engineering, vol. 12, No. 7, Mary Ann Leibert, Inc., UK, (2006), 1787-1798.
Hollinger, Jeffrey O, et al., "Poly(alpha-hydroxy acids): carriers for bon morphogenetic proteins", Biomaterial, vol. 17, (1996), 187-194.
Horton, et al., "Transforming growth factor-beta and fibroblast growth factor act synergistically to inhibit collagen II synthesis through a mechanism involving regulatory DNA sequences", Journal of Cellular Physiology, vol. 141, (1989), 8-15.
Hu, Wei-Shou, "Bioreactors for Animal Cell Cultivation", Recent Advances in Biotechnology, Kluwer Academic Publishers, Netherlands, (1992), 243-261.
Huang, et al., "Tissue Engineering", vol. 8, No. 3, (2002), 469-481.
Hunziker, E.B., et al., "Quantitative structural organization of normal adult human articular cartilage", Osteoarthritis and Cartilage 10, (2002), 564-572.
Iwasa, J, et al., "Clinical application of scaffolds for cartilage tissue engineering", Surg Sports Traumalol Arthorsc vol. 13, No. 4, (2007), 693-703.
Jones, C W, et al., "Matrix-induced autologous chondrocyte implantation in sheep: objective assessments including confocal arthroscopy", J. Orthopaedic Research vol. 26, (2008), 292-303.
Jurgensen, K, et al., "A New Biological Glue for Cartilage-Cartilage Interfaces: Tissue Transglutaminase", JBJS (Am), 1997, vol. 79., (1997), 185-193.
Kandel, et al., "Fetal bovine serum inhibits chondrocyte collagenase production: interleukin 1 reverses this effect", Biochim. Biophys. Acta.: 1053(2-3), (1990), 130-134.
Kato, Y, et al., "Sulfated Proteoglycan Synthesis by Confluent Cultures of Rabbit Costal Chondrocytes Grown in the Presence of Fibroblast Growth Factor", J. Cell Biology, vol. 100., (1985), 477-485.
Kavalkovich, Karl W, et al., "Chondrogenic Differentiation of Human Mesenchymal Stem Cells Within an Alginate Layer Culture System", In Vitro Cell. Dev. Biol.-Animal, vol. 38, Society for In Vitro Biology, USA, (2002), 457-466.
Kim, et al., "OsteoArthritis and Cartilage", vol. 11, (2003), 653-664.
Kimura, Tomoatsu, et al., "Chondrocytes Embedded in CoHagen Gels Maintain Cartilage Phenotype During Long-term Cultures", ?Clinical Orthopaedics and related Research, vol. 186, Japan, (1984), 231-239.
Klagsbrun, et al., "Purification of a cartilage-derived growth factor", The Journal of Biological Chemistry, vol. 255, No. 22, (1980), 10859-10866.
Klagsbrun, et al., "The stimulation of DNA synthesis and cell division in chondrocytes and 3T3 cells by a growth factor isolated from cartilage", Exp Cell Res, vol. 105, (1977), 99-108.
Klein, T J, et al., "Tailoring secretion of proteoglycan 4 (PRG4) in tissue-engineered cartilage", Tissue Engineering, vol. 12, No. 6., (2006), 1429-1439.
Klein, T J, et al., "Tissue engineering of stratified articular cartilage from chondrocyte subpopulations", OsteoArthritis and Cartilage vol. 11, (2003), 595-602.
Kon, E, et al., "Arthroscopic second generation autologous chondrocyte implantation at 48 months follow up", Osteoarthritis and Cartilage vol. 15, Suppl. B, (2007), B44-45.
Kon, E, et al., "Arthroscopic Second-generation Autologous Chondrocyte Implantation Compared with Microfracture of Chondral Lesions of the Knee", Am J. Of Sports Medicine vol. 37, No. 1, (2009), 33-41.

(56) References Cited

OTHER PUBLICATIONS

Krueger, John W, et al., "An In Vitro Study of Flow Response by Cells", Journal of Biomechanics, vol. 4, Pergamon Press, Great Britain, (1971), 31-36.

Kuettner, Klaus E, et al., "Synthesis of Cartilage Matrix by Mammalizn Chondrocytes in Vitro.I. Isolation, Culture Characteristics, and Morphology", The Journal of Cell Biology, vol. 93, The RockefeHer University Press, USA, (1982), 743-750.

Kujawa, et al., "Hyaluronic acid bonded to cell culture surfaces inhibits the program of myogenesis", Developmental Biology, vol. 113, (1986), 10-16.

Kujawa, Mary J, et al., "Hyaluronic Acid Bonded to Cell-Culture Surfaces Timulates Chondrogenesis inStage 24 Limb Mesenchyme Cell Cultures", Developmental Biology, vol. 114, Academic Press, Inc., USA, (1986), 504-518.

Kujawa, Mary J, et al., "Substrate-Bonded Hyaluronic Acid Exhibits a Size-Dependent Stimulation of Chondrogenic Differentiation of Stage 24 Limb Mesenchymal Cells in Culture", Developmental Biology, vol. 114, Academic Press, Inc., USA, (1986), 519-528.

Lee, et al., "Primary cultured chondrocytes of different origins respond differently to bFGF and TGF-B", Life Sciences, vol. 61, No. 3, (1997), 293-299.

Lin, Z, et al., "Gene Expression Profiles of Human Chondrocytes during Passaged Monolayer Cultivation", J. Orthopaedic Research, vol. 26, (2008), 1230-1237.

Liu, Lin-Shu, et al., "An osteoconductive collagen/hyaluronate matrix for bone regeneration", Biomaterials vol. 20, Elsevier, UK, (1999), 1097-1108.

Lucas, Paul A, et al., "Ectopic induction of cartilage and bone by water-soluble proteins from bovine bone using a collagenous delivery vehicle", Journal of Biomedical Materials Research: Applied Biomaterials, vol. 23, No. AI, (1989), 23-39.

Luyten, Frank P, et al., "Articular Cartilage Repair: Potential Role of Growth and Differentiation Factors", Biological Regulation of the Chondrocytes, USA, 227-236.

Mackay, et al., "Chondrogenic differentiation of cultured human mesenchymal stem cells from marrow", Tissue Engineering, vol. 4, No. 4, (1998), 415-430.

Malemud, C J, et al., "The effect of chondrocyte growth factor on membrane transport by articular chondrocytes in monolayer culture", Connective Tissue Research, vol. 6, (1978), 1-9.

Mandl, E W, et al., "Multiplication of human chondrocytes with low seeding densities accelerates cell yield without losing redifferentiation capacity", Tissue Engineering, vol. 10, No. 1/2, (2004), 109-120.

Mandl, E W, et al., "Serum-free medium supplemented with high-concentration FGF2 for cell expansion culture of human ear chondrocytes promotes redifferentiation capacity", Tissue Engineering, vol. 8, No. 4, (2002), 573-582.

Mannheim, A, "Free Autoploastic Cartilage transplantation—Uber freie autoplastische Knorpeltransplantation", Arch. F klin Chir, (1926), 668-672.

Marcacci, M, et al., "Multiple Osteochondral Arthroscopic Grafting (Mosaicplasty) for Cartilage Defects of the Knee: Prospective Study Results at 2-Year Follow-up", J. Arthroscopic & Related Surgery, vol. 21, No. 4., (2005), 462-470.

Marlovits, S, et al., "Changes in the ratio of type-I and type-II collagen expression during monolayer culture of human chondrocytes", JBJS, vol. 86-B, (2004), 286-95.

Marlovits, Stefan, et al., "Early postoperative adherence of matrix-induced autologous chondrocyte implantation for the treatment of full-thickness cartilage defects of the femoral condyle", Knee Surg Sports Traumatol Arthorosc, vol. 13, Springer-Verlag, Austria, (2005), 451-457.

Marvin, H M, "The Value of the Xanthine Diuretics in Congestive Heart Failure", The Journal of the American Medical Association, vol. 87, No. 25, Abstract only, (Dec. 18, 1926), 2131-2132.

Mathiowitz, Edith, et al., "Biologically erodable microspheres as potential oral drug delivery systems", Nature, vol. 386, (Mar. 1997), 410-414.

McNickle, Allison G, et al., "Overview of Existing Cartilage Repair Technology", Sports Med Arthorosc Rev., vol. 16, No. 4, Lippincott Williams & Wilkins, USA, (2008), 196-201.

McQueen, Anne, et al., "Flow Effects on the Viability and Lysis of Suspended Mammalian Cells", Biotechnology Letters, vol. 9, No. 12, California Institute of Technology, USA, (1987), 831-836.

Merchuk, Jose Celman, "Shear Effects on Suspended Cells", Advances in Biochemical Engineering Biotechnology, vol. 44, Springer-Verlag Berlin Heidelberg, (1988).

Merchuk, Jose C, et al., "Why use air-lift bioreactors?", Tibtech, vol. 8, Elsevier Science Publishers Ltd., UK, (1990), 66-71.

Mienaltowski, M J, et al., "Differential gene expression associated with postnatal equine articular cartilage maturation", BMC Musculoskeletal Disorders, vol. 9., (2008), 149-162.

Minas, T, et al., "Current Concepts in the Treatment of Articular Cartilage Defects", Orthopedics, vol. 20., (1997), 525-538.

Mow, V C, et al., "Experimental Studies on Repair of Large Osteochondral Defects at a High Weight Bearing Area of the Knee Joint: A Tissue Engineering Study", Transactions of the ASME, Journal of Biomechanical Engineering, vol. 113, USA, (1991), 198-207.

Nixon, Alan J, et al., "Temporal matrix synthesis and histologic features of a chondrocyte-laden porous collagen cartilage analogue", American Journal of Veterinary Research, vol. 54, No. 2, USA, (1993), 349-356.

Oldshue, J Y, et al., "Comparison of Mass Transfer Characteristics of Radial and Axial Flow Impellers", Mixing Proceedings of the 6th European Conference, Pavia, Italy,, (1988), 345-350.

Papoutsakis, Eleftherios T, "Fluid-mechanical damage of animal cells in bioreactors", TibTech, vol. 9, Elsevier Science Publishers Ltd. (UK), (1991), 427-437.

Pavesio, Allesandra, et al., "Hyaluronan-based scaffolds (Hyalograft C) in the treatment of knee cartilage defects; preliminary clinical findings", Hyaluronan Scaffolds in Cartilage Repair, UK, (2003), 203-217.

Peer, Lyndon, "Diced Cartilage Grafts—New Method for Repair of Skull Defects, Mastoid Fistula and Other Deformities", Archives of Otolaryngology, vol. 38, No. 2, (1943), 156-165.

Peretti, G M, et al., "Meniscal repair using engineered tissue", J. Orthop Res, vol. 19, No. 2., (2001), 278-85.

Polettini, Bruno, "Su neoformazioni carilaginee ed ossee determinate da innesti di frammenti di cartilagine e d'osso fissati", (1922), 179-192.

Reginato, et al., "Formation of nodular structures resembling mature articular cartilage in long-term primary cultures of human fetal epiphyseal chondrocytes on a hydrogel substrate", Arthritis & Rheumatism, vol. 37, No. 9, (1994), 1338-1349.

Ronga, Mario, et al., "Arthroscopic Autologous Chondrocyte Implantation for the Treatment of a Chondral Defect in the Tibial Plateau of the Knee", Arthroscopy: The Journal of Arthroscopic and Related Surgery, vol. 20, No. 1, Italy, (2004), 79-84.

Ronga, Mario, et al., "Tissue Engineering Techniques for the Treatment of a Comples Knee Injury", Arthroscopy: The Journal of Arthroscopic and Related Surgery, vol. 22 No. 5, Italy, (2006), 576.e1-576.e3.

Rosier, R N, et al., "Transforming growth factor bela: an autocrine regulator of chondrocytes", Connective Tissue Research vol. 20., (1989), 295-301.

Rosselot, G, et al., "Development of a serum-free system to study the effect of growth hormone and insulinlike growth factor-I on cultured postembryonic growth plate chondrocytes", In Vitro Cell Dev Biol vol. 28A., (1992), 235-244.

Russlies, M., et al., "A cell-seeded biocomposite for cartilage repair", Annals of Anatomy vol. 184, Urban & Fischer Verlag, UK, (2002), 317-323.

Saini, Sunil, et al., "Concentric Cylinder Bioreactor for Production of Tissue Engineered Cartilage; Effect of Seeding Density and Hydrodynamic Loading on Construct Development", Biotechnol Prog., vol. 19, American Chemical Society and American Institute of Chemical Engineers, USA, (2003), 510-521.

Salter, Robert B, et al., "The Biological Concept of Continuous Passive Motion of Synovial Joints: The First 18 Years of Basic

(56) References Cited

OTHER PUBLICATIONS

Research and Its Clinical Application", Articular Cartilage and Knee Joint Function : Basic Science and Arthroscopy, Raven Press, Ltd., NY, USA, (1990), 335-353.
Schmidt, Tannin A, et al., "Synthesis of Proteoglycan 4 by Chondrocyte Subpopulations in Cartilage Explants, Monolayer Cultures, and Resurfaced Cartilage Cultures", Arthritis & Rheumatism, vol. 50, No. 9, American College of Rheumatology, USA, (2004), 2849-2857.
Schwan, B L, "Human Amniotic Membrane Transplantation for the Treatment of Ocular Surface Disease", Human Amniotic Membrane Transplantation, (2002), 1-7.
Schwarz, Ray P, et al., "Cell Culture for Three-Dimensional Modeling in Rotating-Wall Vessels: An Application of Simulated Microgravity", Journal of Tissue Culture Meth., Tissue Culture Association, TX, USA, (1992), 51-58.
Shahgaldi, B F, et al., "Repair of Cartilage Lesions Using Biological Implants—A Comparative Histological and Biomechanical Study in Goats", Journal of Bone & Joint Surgery, vol. 73-5, UK, (1991), 57-64.
Smith, R. Lane, et al., "Effects of Fluid-Induced Shear on Articular Chondrocyte Morphology and Metabolism In Vitro", Journal of Orthopaedic Research, The Journal of Bone and Joint Surgery, Inc., vol. 13, USA, (1995), 824-831.
Sokoloff, L, et al., "In vitro culture of articular chondrocytes", Federation Proc vol. 32., (1973), 1499-1502.
Sokoloff, L., et al., "Sulfate Incorporation by Articular Chondrocytes in Monolayer Culture", Arthritis and Rheumatism vol. 13, No. 2., (1970), 118-124.
Song, C. X, et al., "Formulation and Characterization of Biodegradable Nanoparticles for Intravascular Local Drug Delivery", Journal of Controlled Release vol. 43, No. 2/03,, XP00632668, (Jan. 18, 1997), 197-212.
Spangenberg, K M, et al., "Histomorphometric Analysis of a Cell-Based Model of Cartilage Repair", Tissue Engineering, vol. 8, No. 5., (2002), 839-46.
Stathopoulos, N. A, et al., "Shear Stress Effects on Human Embryonic Kidney Cells in Vitro", Biotechnology and Bioengineering, vol. XXVII, John Wiley & Sons, Inc., USA, (1985), 1021-1026.
Stewart, Matthew C, et al., "Phenotypic Stability of Articular Chondrocytes In Vitro: the Effects of Culture Models, Bone Morphogenetic Protein 2, and Serum Supplemenation", Journal of Bone and Mineral Research, vol. 15, No. 1, (2000), 166-174.
Stiles, C. D, et al., "Dual control of cell growth by somatomedins and platelet-derived growth factor", PNAS vol. 76, No. 3., (1979), 1279-1283.
Stockwell, R. A, "The cell density of human articular and costal cartilage", J. Anal. vol. 101,No. 4., (1967), 753-763.
Thilly, W. G, et al., "Microcarrier Culture: A Homogeneous Environment for Studies of Cellular Biochemistry", Methods in Enzymology vol. LVIII, ISBN 0-12-181958-2, Academic Press, Inc., New York, New York, United States., (1979), 184-194.
Thilly, W. G, et al., "Microcarriers and the problem of high density cell culture", From Gene to Protein: Translation in Biotechnology vol. 19, Academic Press, Inc., New York, New York, United States., (1982), 75-103.
Trattnig, S., et al., "Differentiating normal hyaline cartilage from post-surgical repair tissue using fast gradient echo imaging in delayed gadolinium-enhanced MRI (dGEMRIC) at 3 Tesla", Eur Radial vol. 18., (2008), 1251-1259.
Trattnig, S., et al., "Quantitative T2 Mapping of Matrix-Associated Autologous Chondrocyte Transplantation at 3 Tesla an in vivo Cross-Sectional Study", Investigative Radiology vol. 42, No. 6., (2007), 442-448.
Trattnig, Siegfried, et al., "Matrix-based autologous chondrocyte implantation for cartilage repair: noninvasive monitoring by high-resolution magnetic resonance imaging", Magnetic Resonance Imaging, vol. 23, Elsevier, Austria, (2005), 779-787.
Vacant!, C. A, et al., "Synthetic Polymers Seeded with Chondrocytes Provide a Template for New Cartilage Formation", Plastic and Reconstructive Surgery, vol. 88, No. 5, (1991), 753-759.
Vanderploeg, E. J, et al., "Articular chondrocytes derived from distinct tissue zones differentially respond to in vitro oscillatory tensile loading", Osteoarthritis and Cartilage vol. 16., (2008), 1228-1236.
Venkat, Raghavan V, et al., "Study of Hydrodynamics in Microcarrier Culture Spinner Vessels: A Particle Tracking Velocimetry Approach", Biotechnology and Bioengineering, vol. 49, John Wiley & Sons, Inc., USA, (1996), 456-466.
Verwoerd, C.D.A., et al., "Wound Healing of Autologous Implants in the Nasal Septal Cartilage", Department of Otorhinolaryngology and Pathology, ORL vol. 53, (1991), 310-314.
Vishwakarma, G. K, et al., "Isolation & cryo-preservation of human foetal articular chondrocytes", Indian J. Med Res vol. 98., (1993), 309-313.
Von Schroeder, Herbert P, et al., "The use of polylatic acid matrix and periosteal grafts for the reconstruction of rabbit knee articular defects", Journal of Biomedical Materials Research, vol. 25, (1991), 329-339.
Willers, Craig, et al., "Articular cartilage repair: procedures versus products", Expert Rev. Med. Devices, vol. 4., No. 3, Future Drugs Ltd, US, (2007), 373-392.
Xu, et al., "Injectable Tissue-Engineered Cartilage with Different Chondrocyte Sources", vol. 113, (2004), 1361-1371.
Yamashita, F., et al., "The Transplantatoin of Autogeneic Osteochondral Fragment for Osteochondritis Dissecans of the Knee", Orthopedics 15, (1992), 1191-1199.
Yoshihashi, Yuji, et al., "Tissue Reconstitution by Isolated Articular Chondrocytes in vitro", J. Jpn. Orthop. Assoc., vol. 58, (1983), pp. 629-641.
Zheng, M H, et al., "Matrix-induced autologous chondrocyte implantation (MACI): Biological and Histological Assessment", Tissue Engineering, vol. 13, No. 4., (2007), 737-746.
Zimber, M P, et al., "TGF-β Promotes the Growth of Bovine Chondrocytes in Monolayer Culture and the Formation of Cartilage Tissue on Three-Dimensional Scaffolds", Tissue Engineering, vol. 1, No. 3., (1995), 289-300.
"U.S. Appl. No. 13/327,238, Notice of Allowance mailed Apr. 30, 2013", 6 pgs.
"U.S. Appl. No. 13/327,238, Response filed Apr. 2, 2013 to Non Final Office Action mailed Apr. 2, 2013", 6 pgs.
"U.S. Appl. No. 13/327,265 , Response filed May 21, 2013 to Final Office Action mailed Jan. 31, 2013", 7 pgs.
"U.S. Appl. No. 13/327,286, Notice of Allowance mailed Apr. 24, 2013", 6 pgs.
"U.S. Appl. No. 13/327,286, Response filed Apr. 2, 2013 to Non Final Office Action mailed Feb. 7, 2013", 6 pgs.
"U.S. Appl. No. 13/327,286, Supplemental Notice of Allowability mailed May 15, 2013", 2 pgs.
"U.S. Appl. No. 13/327,286, Supplemental Notice of Allowability mailed May 28, 2013", 4 pgs.
"Australian Application Serial No. 2006282754, Response filed May 7, 2013 to First AU Examiner Report mailed Nov. 8, 2011", 13 pgs.
"Australian Application Serial No. 2006282754, Subsequent Examiners Report mailed Jun. 14, 2013", 3 pgs.
"European Application Serial No. 08745639.8, Extended European Search Report mailed Apr. 3, 2013", 7 pgs.
Egkher, E., Indications and Limits of Fibrin Adhesive Applied to Traumatological Patients, Traumatology and Orthopaedics, 1986, pp. 144-151, vol. 7, Springer-Verlag, Berlin Heidelberg.
Erikson, U. et al, English abstract only, A roentgenological method for the determination of renal blood flow. A preliminary report, Acta Soc Med Ups, 1965, pp. 213-6, vol. 70, No. 3.
Erol, O.O., The Turkish Delight: A Pliable Graft for Rhinoplasty, Plast. Reconstr. Surg., 2000, pp. 2229-2241, vol. 105.
Evans, C.H., et al, Experimental Arthritis Induced by Intraarticular Injection of Allogenic Cartilageinous Particles into Rabbit Knees, Arthritis and Rheumatism, 1984, pp. 200-207, vol. 27, No. 2.
Farrior, R.T., Implant Materials in Restoration of Facial Contour, Laryngoscope, 1966, pp. 934-954, vol. 76, No. 5.

(56) References Cited

OTHER PUBLICATIONS

Feldman, M.D., et al, Compatibility of Autologous Fibrin Adhesive With Implant Materials, Arch Otolaryngol Head Neck Surg, 1988, pp. 182-185, vol. 114.
Fontana, A., et al, Cartilage Chips Synthesized with Fibrin Glue in Rhinoplasty, Aesth Plast Surg, 1991, pp. 237-240, vol. 15.
Furukawa, T. et al, Biochemical Studies on Repair Cartilage Resurfacing Experimental Defects in the Rabbit Knee, J Bone Joint Surg Am, 1980, pp. 79-89, vol. 62, No. 1.
Gaudernak, T., et al, Clinical Experiences Using Fibrin Sealant in the Treatment of Osteochondral Fractures, Fibrin Sealant in Operative Medicine-Traumatology and Orthopaedics, 1986, pp. 91-102, vol. 7, Springer-Verlag, Berlin Heidelberg.
Gerngross, H. et al, Experimental Studies on the Influence of Fibrin Adhesive, Factor XIII, and Calcitonin on the Incorporation and Remodeling of Autologous Bone Grafts, Arch Orthop Trauma Surg, 1986, pp. 23, 31, vol. 106.
Gersdorff, M.C.H., and Robillard, T.A., "How I Do It"—Otology and Neurotology. A Specific Issue and Its Solution. A New Procedure for Bone Reconstruction in OTO-Microsurgery: A Mixture of Bone Dust and Fibrinogen Adhesive, Laryngoscope, 1985, pp. 1278-1280, vol. 95.
Ghadially, J.A. and Ghadially, F.N., Evidence of Cartilage Flow in Deep Defects in Articular Cartilage, Virchows Arch B. Cell Path, 1975, pp. 193-204, vol. 18.
Ghadially, J.A. et al, Long-Term Results of Deep Defects in Articular Cartilage, Virchows Arch B. Cell Path, 1977, pp. 125-136, vol. 25.
Ghazavi, M.T. et al, Fresh Osteochondral Allografts for Post-Traumatic Osteochondral Defects of the Knee, JBJS, 1997, pp. 1008-1013, vol. 79-B.
Gibson, T. et al, The Long-Term Survival of Cartilage Homografts in Man, British Journal of Plastic Surgery, 1958, pp. 177-187, vol. 11.
Gooding, C.R. et al, Abstract only of a prospective, randomised study comparing two techniques of autologous chondrocyte implantation for osteochondral defects in the knee: Periosteum covered versus type I/III collagen covered, Knee, 2006, pp. 203-210, vol. 13, No. 3.
Greco, F. et al, Experimental Investigation into Reparative Osteogenesis With Fibrin Adhesive, Arch Orthop Trauma Surg, 1988, pp. 99-104, vol. 107.
Hamra, S.T., Crushed Cartilage Grafts over Alar Dome Reduction in Open Rhinoplasty, Plast Reconstr Surg., 1993, pp. 352-356, vol. 92, No. 2.
Hangody, L. et al, English Abstract only, Autogenous Osteoctiondralf Craft Technique for Replacing Knee Cartilage Defects in Dogs, Autogenous Osteochondral Mosaicplasty, Orthop Int, 1997, pp. 175-181, vol. 5, No. 3.
Hangody, L. and Fules, P., Autologous Osteochondral Mosaicplasty for the Treatment of Full-Thickness Defects of Weght-Bearing Joints: Ten Years of Experimental and clinical Experience, JBJS, 2003, pp. 25-32, vol. 85.
Hangody, L. et al, Mosaicplasty for the Treatment of Articular Defects of the Knee and Ankle, Clin Orthopaedics and Rel Res, 2001, pp. S328-S336, No. 391S.
Harbin, M. and Moritz, A.R., Autogenous Free Cartilage Transplanted into Joints, Archives of Surgery, 1930, pp. 885-896, vol. 20, No. 6.
He, Q. et al, Repair of flexor tendon defects of rabbit with tissue engineering method, Chinese Journal of Traumatology, 2002, pp. 200-208, vol. 5, No. 4.
Helidonis, E. et al, Laser Shaping of Composite Cartilage Grafts, Am. J. Otolaryngology, 1993, pp. 410-412, vol. 14, No. 6.
Homminga, G.N. et al, Perichondral Grafting for Cartilage Lesions of the Knee, British Editorial Society of Bone and Joint Surgery, 1990, pp. 1003-1007, vol. 72B.
Homminga, G.N., Repair of Chrondral Lesions of the Knee with a Perichondrial Graft, Fibrin Sealant in Operative Medicine-Orthopedic Surgery Maxillofacial Surgery, 1986, pp. 61-69, vol. 4, Springer-Verlag, Berlin Heidelberg.
Hoover, N.W. et al, Skin Arthroplasty of the Hip, An Experimental Study in Dogs, JBJS, 1961, pp. 1155-1166, vol. 43-A, No. 8.

Horas, U. et al, Autologous Chondrocyte Implantation and Osteochondral Cylinder Transplantation in Cartilage Repair of the Knee Joint: A Prospective, Comparative Trial, JBJS, 2003, pp. 185-192, vol. 85.
Horton, W.A. et al, Characterization of a type II collagen gene (COL2A1) mutation identified in cultured chondrocytes from human hypochondrogenesis, PNAS, 1992, pp. 4583-4587, vol. 89.
Hunziker, E.B., Articular cartilage repair: basic science and clinical progress. A review of the current status and prospects, Osteoarthritis and Cartilage, 2001, pp. 432-463, vol. 10.
Hurtig, M.B. et al, Effects of Lesion Size and Location on Equine Articular Cartilage Repair, Can J. Vet Res, 1988, pp. 137-146, vol. 52.
Hurtig, M.B., Use of autogenous cartilage particles to create a model of naturally occurring degenerative joint disease in the horse, Equine Vet J Suppl, 1988, pp. 19-22, No. 6.
Imhoff, A.B., et al, English Abstract only of Autologous Osteochondral transplantation on various joints, Orthopade, 1999, pp. 33-44, vol. 28, No. 1.
Ishida, T., English Abstract only of the Use of a Fibrin Adhesive for a Cartilage Graft Basic and Clinical Studies, Japanese J. of Plastic and Reconstructive Surgery, 1990, pp. 215-230, vol. 33, No. 1.
Ishizaki, Y. et al, Autocrine Signals Enable Chondrocytes to Survive in Culture, J. Cell Biol. 1994, pp. 1069-1077, vol. 126, No. 4.
Ito, Y. et al, Localization of chondrocyte precursors in periosteum, Osteoarthritis and Cartilage, 2001, pp. 215-223, vol. 9.
Ittner, G. et al, English Abstract only of Treatment of flake fracture of the talus, Z. Orthop Ihre Grenzgeb, 1989, pp. 183-186, vol. 127, No. 2.
Jakob, R.P. et al, Autologous Osteochondral Grafting in the Knee: Indication, Results and Reflections, Clinical Orthopaedics and Rel Res, 2002, pp. 170.184, No. 401.
Jin, C.Z. et al, Human Amniotic Membrane as a Delivery Matrix for Articular Cartilage Repair, Tissue Engineering, 2007, pp. 693-702, vol. 13, No. 4.
Johnson, L.L., Arthroscopic Abrasion Arthroplasty Historical and Pathologic Perspective: Present Status, Arthroscopy: The Journal of Arthroscopic and Related Surgery, 1986, pp. 54-69, vol. 2, No. 1.
Kanzaki, J. et al, Use of Fibrin Glue in Intracranial Procedures Following Acoustic Neuroma Surgery: Application in Facial Nerve Reconstruction and Prevention of Cerebrospinal Fluid Rhinorrhea, Fibrin Sealing in Surgical and Nonsurgical Fields-Neurosurgery Ophthalmic Surgery ENT, 1994, pp. 162-168, vol. 5, Springer-Verlag, Berlin Heidelberg.
Kaplonyi, G. et al, The use of fibrin adhesive in the repair of chondral and osteochondral injuries, Injury. 1988, pp. 267-272, vol. 19.
Kawamura, M. and Urist, M.R., Human Fibrin Is a Physiologic Delivery System for Bone Morphogenetic Protein, Clin Ortho Rel Res, 1988, pp. 302-310, No. 235.
Keller, J. et al, Fixation of osteochondral fractures, Acta Orthop Scand, 1985, pp. 323-326, vol. 56.
Kettunen, K.O., Skin Arthroplasty in the Light of Animal Experiments With Special Reference to Functional Metaplasia of Connective Tissue, Acta Ortho Scand, 1958, pp. 9-69, Suppl. XXIX.
Kirilak, Y. et al, Fibrin sealant promotes migration and proliferation of human articular chondrocytes: possible involvement of thrombin and protease-activated receptors, Int. J. Mol. Med, 2006, pp. 551-558, vol. 17, No. 4.
Knutsen, G. et al, Autologous Chondrocyte Implantation Compared with Microfracture in the Knee. A Randomized Trial, JBJS, 2004, pp. 455-464, vol. 86.
Kon, E. et al, Second Generation Issues in Cartilage Repair, Sports Med Arthrosc Rev., 2008, pp. 221-229, vol. 16.
Korhonen, R.K. et al, Importance of the superficial tissue layer for the indentation stiffness of articular cartilage, Medical Eng. Phys, 2002, pp. 99-108, vol. 24.
Lane, J.M. et al, Joint Resurfacing in the Rabbit Using an Autologous Osteochondral Graft, JBJS, 1977, pp. 218-222, vol. 59-A, No. 2.
Dupertuis, S.M., Growth of Young Human Autogenous Cartilage Grafts, Plast Reconstr Surg, 1946, pp. 486-493, vol. 5, No. 6.
Albrecht, F. et al, Closure of Osteochondral Lesions Using Chondral Fragments and Fibrin Adhesive, Arch Orthop Trauma Surg, 1983, pp. 213-217, vol. 101.

(56) References Cited

OTHER PUBLICATIONS

Albrecht, F., English Abstract of German article Closure of joint cartilage defects using cartilage fragments and fibrin glue, Fortschr Med., 1983, pp. 1650-1652, vol. 101, No. 37.
Dupertuis, S. M., Actual Growth of Young Cartilage Transplants in Rabbits, Archives of Surgery, 1941, pp. 32-63, vol. 43.
Eberlin, J.L. et al, Osteocartilagenous Reconstruction, Plastic Surgery Nerve Repair Burns, Fibrin Sealing in Surgical and Nonsurgical Fields, 1995, pp. 20-24, vol. 3 Springer-Verlag, Berlin, Heidelberg.
De Kleine, E.H., The Chondrojet, A Simplified Method for Handling of Diced Cartilage, Plast Reconstr Surg, 1946, pp. 95-102, vol. 3, No. 1.
Aston, J.E. and Bentley G., Repair of Articular Surfaces by Allografts of Articular and Growth-Plate Cartilage, J Bone Joint Surg Br.,1986, pp. 29-35, vol. 68, No. 1.
Bacsich, P. and Wyburn, G.M., XXXVIII. The Significance of the Mucoprotein Content on the Survival of Homografts of Cartilage and Cornea, 1947, P.R.S.E., pp. 321-327, vol. LXII, B, Part III.
Bayliss, M.T. and Roughley, P.J., The properties of proteoglycan prepared from human articular cartilage by using associative caesium chloride gradients of high and low starting densities, Biochem. J., 1985, pp. 111-117, vol. 232.
Bently, G. and Greer, R.B. III, Homotransplantation of Isolated Epiphyseal and Articular Cartilage Chondrocytes into Joint Surfaces of Rabbits, Nature, 1971, pp. 385-388, vol. 230.
Berlet, G.C. et al, Treatment of Unstable Osteochondritis Dissecans Lesions of the Knee Using Autogenous Osteochondral Grafts (Mosaicplasty), J. Arthroscopic and Related Surgery, 1999, pp. 312-316, vol. 15, No. 3.
Decher, H., Reduction of Radical Cavities by Means of Homologous Cartilage Chips, Larying. Rhinol. Otol., 1985, pp. 423-426, vol. 64.
Bodo, G. et al, Arthroscopic Autologous Osteochondral Mosaicplasty for the Treatment of Subchondral Cystic Lesion in the Medial Femoral Condyle in a Horse, Acta Veterinaria Hungarica, 2000, pp. 343-354, vol. 48, Vo. 3.
Craigmyle, M.B.L., Cellular Survival in Long-Term Cartilage Grafts in the Rabbit, Transplantation Bulletin, 1958, pp. 123, vol. 5, No. 1.
Craigmyle, M.B.L., An Autoradiographic and Histochemical Study of Long-Term Cartilage Grafts in the Rabbit, J. of Anatomy, 1954, pp. 467-473, vol. 92, Part 3.
Coster, D.J. and Galbraith, J.E.K., Diced cartilage grafts to correct enophthalmos, British J. Ophthalmology, 1980, pp. 135-136, vol. 64.
Chesterman, P.J. et al, Homotransplantation of Articular Cartilage and Isolated Chondrocytes, An Experimental Study in Rabbits, JBJS, 1968, pp. 184-197.
Breadon, G.E., et al, Autografts of Uncrushed and Crushed Bone and Cartilage, Bone and Cartilage Autografts, 1979, pp. 75-80, vol. 105.
Brighton, C.T., et al, Articular Cartilage Preservation and Storage I. Application of Tissue Culture Techniques to the Storage of Viable Articular Cartilage, Arthritis Rheum., 1979, pp. 1093-1101, vol. 22, No. 10.
Brittberg, M. et al, Treatment of Deep Cartilage Defects in the Knee With Autologous Chondrocyte Transplantation, The New England Journal of Medicine, 1994, pp. 889-895, vol. 331, No. 14.
Brittberg, M. Autologous Chondrocyte Transplantation, Clinical Orthopaedics and Related Research, 1999, pp. S147-S155, No. 367S.
Brittberg, M. et al, Treatment of Deep Cartilage Defects in the Knee with Autologous Chondrocyte Transplantation, N Engl J Med., 1994, pp. 889-895, vol. 331, No. 14.
Brodkin, H.A. and Peer, L.A., Diced Cartilage for Chest Wall Defects, 1954, pp. 97-102, vol. 28, No. 1.
Brown, B.L. et al, Transplantation of Fresh Allografts (Homografts) of Crushed and Uncrushed Cartilage and Bone: A 1-Year Analysis in Rabbits, The Laryngoscope, 1980, pp. 1521-1532, vol. 90.
Bruns, J. et al, Long-Term Follow up Results after Gluing Osteochondral Fragments in Patients with Osteochondrosis Dissecans Langenbecks Arch Chir, 1993, pp. 160-166, vol. 378.
Bruns, J. et al, Autologous rib perichondrial grafts in experimentally induced osteochondral lesions in the sheep-knee joint: morphological results, Virchows Archiv A. Pathol Anat, 1992, pp. 1-8, vol. 421.

Wagner, P.D. and Westen, E., et al, Improved blood buffering in high-altitude natives?, J Appl Physiol, 2002, pp. 2214-2215, vol. 93.
Wakitani, S., et al, Repair of Rabbit Articular Surfaces With Allograft Chondrocytes Embedded in Collagen Gel, JSJS, 1989, pp. 74-80, vol. 71-B.
Wei, X., et al, The Effect of Sodium Selenite on Chondrocytes in Monolayer Culture, Arthritis and Rheumatism, 1986, pp. 660-664, vol. 29, No. 5.
Welsh, F., The alar cartilage morseler: a new instrument, Br. J. Plastic Surgery, 1983, pp. 483-484, vol. 36.
Wilfilingseder, P., Cranioplasties by means of diced cartilage and split rib grafts, Min Chir, 1983, pp. 837-843, vol. 38, No. 12.
Wischhofer, E., et al, English abstract only of The Behaviour of Autologous Spongiosa Transplants from the Dial Crest With and Without Fibrinadhesive in the Canine Femoral Epiphysis, Unfallheilkunde, 1982, ppl. 250-252, vol. 85.
Xu, J.W. et al, Injectable Tissue-Engineered Cartilage with Different Chondrocyte Sources, Plast. Reconstr. Surg., 2004, pp. 1361-1371, vol. 113.
Yamamoto, E. et al, Use of Micro-Sliced Homograft Cartilage Plates in Tympanoplasty, Acta Otolaryngol, 1985, pp. 123-129, vol. 419.
Yamashita, F. et al, The Transplantation of an Autogeneic Osteochondral Fragment for Osteochondritis Dissecans of the Knee, Clin Ortho Rel Res, 1985, pp. 43-50, vol. 201.
Yilmaz, S. et al, Viability of Diced, Crushed Cartilage Grafts and the Effects of Surgicel (Oxidized Regenerated Cellulose) on Cartilage Grafts, Plast. Reconstru. Surg. 2001, pp. 1054-1060, vol. 108.
Young, F., Autogenous Cartilage Grafts, An Experimental Study, Surgery, 1941, pp. 7-20, vol. 10.
Young, F., The use of autogenous rib cartilage grafts to repair surface defects in dog joints, Surgery, 1940, pp. 254-263, vol. 7.
Zahn, F., On the Fate of Tissues Implanted in the Organism, Int. Med. Congr. In Geneva, Biology Section—Meeting of Sep. 11, 1877, pp. 1-4.
Zalzal, G.H. et al, Cartilage Grafts-Present Status, Head and Neck Surgery, 1986, pp. 363-374, vol. 8.
Zilch, V.H. and Talke, M., Gluing Small Osteochondral Fragments with Fibrin Glue in Hand Surgery. Clinical Experiences, Handchirurgie, 1980, pp. 77-81, vol. 12.
Zilch, V.H., Animal Experiments Investigating the Fixation of Small Osteochondral Fragments by Means of Fibrin Glue, Handchirurgie, 1980, pp. 71-75, vol. 12.
Zilch, H. and Friedebold, G., English summary only of Fixing of Osteochondral Fragments with Fibrinogen Clue. Clinical Experiences, Akt. Traumatol., 1981, pp. 136, vol. 11.
Zilch, H. and Talke, M., English summary only of Fibrin sealant in cases of little osteochondral fragments of the upper limb, Ann. Chir. Main, 1987, pp. 173-176, vol. 6, No. 2.
Zilch, H. and Talke, M., English summary only of Fixation of Small Osteochondral Fragments with the Fibrinogen Adhesive, Clinical Report, Ann. Chir. Main, 1980, pp. 77-81, vol. 12.
Adkisson, H.D., IV et al, In Vitro Generation of Scaffold Independent Neocartilage, Clin Ortho Rel Res, 2001, pp. S280-S294, No. 391S.
Caruso, E. et al, Repopulation of Laser-Perforated Chondroepiphyseal Matrix with Xenogeneic Chondrocytes: An Experimental Model, JBJS, 1996, pp. 102-107, vol. 14.
Cheng, N.C. et al, Chondogenic Differentiation of Adipose-Derived Adult Stem Cells by a Porous Scaffold Derived from Native Articular Cartilage Extracellular Matrix, Tissue Engineering, Part A, 2009, pp. 231-241, vol. 15, No. 2.
Davis, J.S., Some of the Problems of Plastic Surgery, Ann Surg., 1917, pp. 88-94, vol. 66, No. 1.
Davis, W.B. and Gibson, T., Absorption of Autogenous Cartilage Grafts in Man, British Journal of Plastic Surgery, 1957, pp. 177-185, vol. 9.
Gelse, K. et al, Paracrine Effect of Transplanted Rib Chondrocyte Spheroids Supports Formation of Secondary Cartilage Repair Tissue, J. Ortho Res, 2009, pp. 1216-1225, vol. 27.
Hendrickson, D.A. et al, Chondrocyte-Fibrin Matrix Transplants for Resurfacing Extensive Articular Cartilage Defects, J. Ortho Res, 1994, pp. 485-497, vol. 12 No. 4.
Homminga, G.N. et al, Chondrocyte behavior in fibrin glue in vitro, Acta Orthop Scand, 1993, pp. 441-445, vol. 64, No. 4.

(56) References Cited

OTHER PUBLICATIONS

Howard, R.D., et al, Long-term fate and effects of exercise on sternal cartilage autografts used for repair of large osteochondral defects in horses, Am J Vet Res, 1994, pp. 1158-1167, vol. 55, No. 8.
Hutchinson, J., Observations on bone transplants in the anterior chamber of the eye, Glasgow Med J., 1949, pp. 357-363, vol. 30, No. 10.
Jeffries, D.J.R., and Evans, P.H.R., Cartilage regeneration following septal surgery in young rabbits, J. Laryngology and Otology, 1984, pp. 577-583, vol. 98.
Gu, J.D., et al, True Denisity of Normal and Enzymatically Treated Bovine Articular Cartilage, Trans Orthop Res Soc., 1999, pp. 642, vol. 24.
Kim, M.K. et al, Autologous chondrocyte implantation in the knee using fibrin, Knee Surg. Sports Traumatol. Arthrosc., 2010, pp. 528-534, vol. 18.
Libera, J., et al, Cartilage Engineering, Fundamentals of Tissue Engineering and Regenerative Medicine, 2009, pp. 233-242, Chapter 18, Springer-Verlag, Berlin Heidelberg.
Liu, X., et al, In vivo ectopic chondrogenesis of BMSCs directed by mature chondrocytes, Biomaterials, 2010, pp. 9406-9414, vol. 31.
Longacre, J.J. et al, Further observations of the behavior of autogenous split-rib grafts in reconstruction of extensive defects of the cranium and face, Plas Reconstr Surg, 1957, pp. 281-296, vol. 20, No. 4.
Marmotti, A., et al, One-Step osteochondral repair with cartilage fragments in a composite scaffold, Knee Surg Sports Traumatol Arthrosc., Feb. 21, 2012, [Epub ahead of print], 12 pages.
McKibbin B. and Holdsworth, F.W., The dual nature of epiphysial cartilage, J Bone Joint Surg Br., 1967, pp. 351-361, vol. 49, No. 2.
Medawar, P.B., Immunity to homologous grafted skin; the fate of skin homografts transplanted to the brain, to subcutaneous tissue, and to the anterior chamber of the eye, Br J Exp Pathol., 1948, pp. 58-69, vol. 29, No. 1.
Munirah, S. et al, Articular cartilage restoration in load-bearing osteochondral defects by implantation of autologous chondrocyte-fibrin constructs: an experimental study in sheep, J Bone Joint Surg Br., 2007, pp. 1099-1109, vol. 89, No. 8.
Nehrer, S. et al, Three-year clinical outcome after chondrocyte transplantation using a hyaluronan matrix for cartilage repair, Eur J Radiol., 2006, pp. 3-8, vol. 57, No. 1.
Obradovic, B., et al, Integration of engineered cartilage, J Orthop Res., 2001, pp. 1089-1097, vol. 19, No. 6.
Verwoerd, C.D.A. et al, Stress and woundhealing of the cartilaginous nasal septum, Acta Otolaryngol., 1989, pp. 441-445, vol. 107, Nos. 5-6.
Pierce, A. et al, Surgicel: macrophage processing of the fibrous component, Int J Oral Maxillofac Surg., 1987, pp. 338-345, vol. 16, No. 3.
Roemhildt, M.L. et al, Material properties of articular cartilage in the rabbit tibial plateau, J. Biomech, 2006, pp. 2331-2337, vol. 39, No. 12.
Schubert, T. et al, Long-term effects of chondrospheres on cartilage lesions in an autologous chondrocyte implantation model as investigated in the SCID mouse model, International Journal of Molecular Medicine, 2009, pp. 455-460, vol. 23.
Selktar, D., Lecture Bulletin Natures Healing Matrix, Technion Focus, May 2006, 1 page.
Silverman, R.P., et al, Adhesion of Tissue-Engineered Cartilage to Native Cartilage, Plast. Reconstr Surg, 2000, pp. 1393-1398, vol. 105.
Sin, Y.M. et al, Studies on the mechanism of cartilage degradation, J Pathol., 1984, pp. 23-30, vol. 142, No. 1.
Van Susante, J.L.C. et al, Resurfacing potential of heterologous chondrocytes suspended in fibrin glue in large fullthickness defects of femoral articular cartilage: an experimental study in the goat, Biomaterials, 1999, pp. 1167-1175, vol. 20, No. 13.
Buckwalter, J.A., Articular Cartilage Injuries, Clinical Orthopaedics and Related Research, 2002, pp. 21-37, vol. 402.
Bujia, J. et al, Culture and Cryopreservation of Chondrocytes from Human Cartilage Relevance for Cartilage Allografting in Otolaryngology, ORL, 1992, pp. 80-84, vol. 54.
Bujia, J., Determination of the Viability of Crushed Cartilage Grafts: Clinical Implications for Wound Healing in Nasal Surgery, Ann Plast Surg, 1994, pp. 261-265, vol. 32.
Cherubino, P. et al, Autologous chondrocyte implantation using a bilayer collagen membrane: A preliminary report, J. Ortho Surg, 2003, pp. 10-15, vol. 11, No. 1.
Calandruccio, R. A. and Gilmer, W.S., Proliferation, Regeneration, and Repair of Articular Cartilage of Immature Animals, JBJS, 1962, pp. 431-455, vol. 44A, No. 3.
Chen, F.S. et al, Repair of Articular Cartilage Defects: Part II. Treatment Options, Am. J. Ortho, 1999, pp. 88-96.
US 8,382,851, 02/2013, Gage et al. (withdrawn)

\* cited by examiner

Figure 1, Chondral Defect – Uniform Distribution
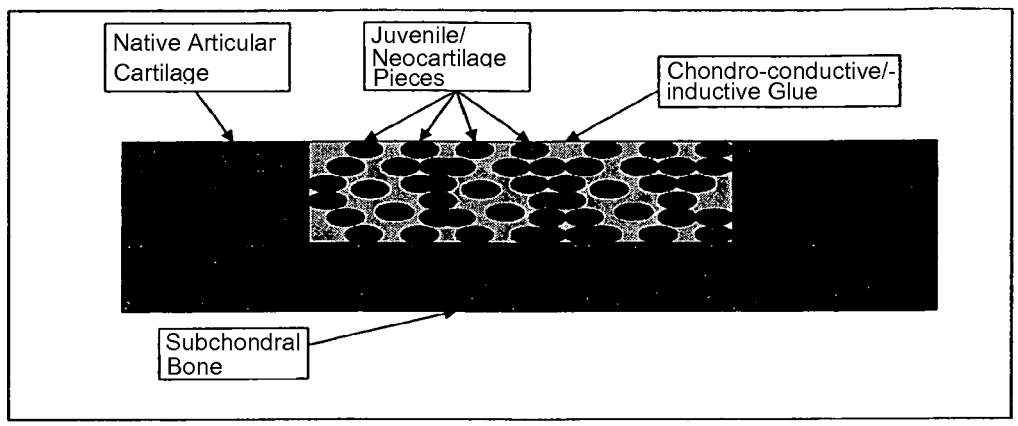
Figure 2, Chondral Defect – Packed Cartilage
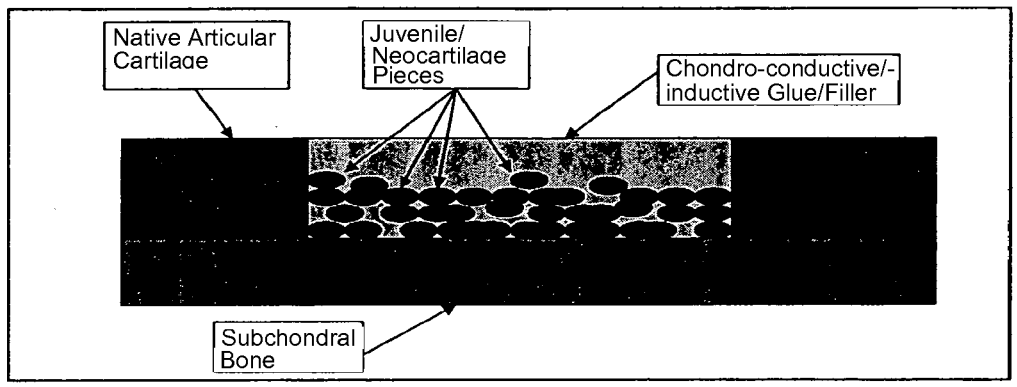
Figure 3, Osteochondral Defect
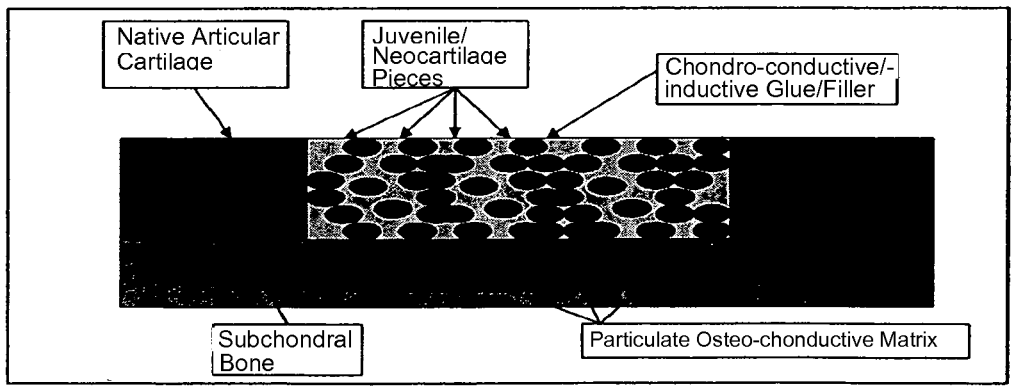

JUVENILE CARTILAGE COMPOSITION

CROSS-REFERENCE TO RELATED APPLICATIONS

This application is a continuation of copending U.S. patent application Ser. No. 12/861,404 filed Aug. 23, 2010, which is a continuation of U.S. patent application Ser. No. 11/010,779 filed Dec. 13, 2004, now U.S. Pat. No. 7,824,711, which claims priority to Provisional Application Ser. No. 60/528,865 filed on Dec. 11, 2003, which is incorporated herein by reference in its entirety.

STATEMENT REGARDING FEDERALLY SPONSORED RESEARCH OR DEVELOPMENT

Not Applicable.

REFERENCE TO A SEQUENCE LISTING

Not Applicable.

BACKGROUND OF THE INVENTION

Injuries and damage to articular cartilage result in lesions in the cartilage that often lead to disability, pain and reduced or disturbed functionality. Historically there has been limited success in the repair of these injuries and lesions, (i.e., characterized by a repair that re-establishes a structurally and functionally competent articular cartilage tissue of a lasting nature). Many injuries and defects to articular cartilage penetrate the bone and bone-marrow spaces as well (i.e., an osteochandral defect).

Articular cartilage tissue has a tough and elastic character; it covers the ends of bones in joints and enables the bones to move smoothly over one another. Numerous diseases, including osteoarthritis, and traumatic injuries from activities and accidents cause damage to articular cartilage.

Articular cartilage lacks a direct blood supply, is aneural, alymphatic, and contains a single cell type, the chondrocyte. Its lack of vascularization, high matrix-to-cell ratio and lack of a local source of undifferentiated cell reserves results in a limited capacity to regenerate following injury or degenerative loss. Repair of damaged or diseased mature articular cartilage historically has been difficult because of its very limited ability to self-repair. Adult human articular cartilage usually does not self-repair or only partially heals under normal biological conditions.

In the past, repair interventions based on the use of adult human tissue or isolated chondrocyte autografts or allografts have not provided completely satisfactory results, from the standpoint of a restoration of the architecture of the articulating surface.

Grafting of pure articular cartilage alone has shown little or no success, nor has the implantation of isolated cartilage flakes after traumatic dissociation or ablation without a bony support, as cartilage does not adhere to bony surfaces nor is bone able to facilitate cartilage fixation.

In vitro culture of chondrocytes under controlled conditions can give rise to normal articular cartilage tissue growth. Adkisson, U.S. Pat. Nos. 6,235,316 and 6,645,764. However, normal adult chondrocytes generally have lost their potential to reproduce and generate new cartilage in vivo, although they are responsible for maintaining tissue homeostasis. Accordingly, there exists a need for improved compositions and methods for repairing articular cartilage.

BRIEF SUMMARY OF THE INVENTION

One aspect of the present invention is directed to compositions including a cartilage or a neocartilage construct of juvenile cartilage particles and biocompatible chondro-conductive/inductive matrix. Some embodiments may further include an osteo-conductive matrix. The cartilage may be distributed throughout substantially all of the biocompatible chondro-conductive matrix or just a portion of the matrix, the portion may range from 90 to 10%. In some embodiments the surface-to-volume ratio of the cartilage particles is greater than 1. In any embodiment the biocompatible chondro-conductive/inductive matrix may be fibrinogen, fibrinogen/thrombin, albumin, in-situ forming poly(ethylene glycol) (PEG) hydrogel, fibrin/hyaluronate, fibrin/collagen/hyaluronate, PEG/hyaluronate, PEG/collagen, other plasma and protein-based adhesives and sealants, other natural adhesives and sealants and any combination thereof. In any embodiment the composition may further comprise an osteo-conductive matrix. The osteo-conductive matrix may be fibrinogen, fibrinogen/thrombin, fibrin/tri-calcium phosphate, fibrin/collagen/tri-calcium phosphate, fibrin/hyaluronate/tri-calcium phosphate, in-situ forming PEG hydrogel sealants, PEG/tri-calcium phosphate, PEG/collagen, demineralized bone matrix, and any combination thereof. In any embodiment the composition may include an associated matrix containing collagen, polylactic acid (PLA) and polyglycolic acid (PGA).

In any embodiment the composition may include other cartilage tissues, such as costal cartilage, nasal cartilage, trachea cartilage, sternum cartilage and any other cartilage tissue that contains Collagen II and not Collagen I and III.

Another aspect of the invention may include a composition containing neocartilage or juvenile cartilage particles from a non-autologous source.

Another aspect of the invention is directed toward or includes methods of using the inventive compositions for inducing articular cartilage (i.e., a chondral defect) formation, repairing articular cartilage or repairing articular cartilage together with filling a bone defect in vertebrates (i.e., an osteochondral defect). The methods include disposing the inventive compositions in a site where regeneration, augmentation, the induction of articular cartilage formation, the repairing of articular cartilage or the repairing of articular cartilage and also filling a bone defect, is desired.

Another aspect of the invention includes a device including any of the compositions of the invention and the device may also be used in a method of articular cartilage repair by disposing the device in a defect in need of repair.

Yet another aspect of the invention includes a method of preparing any of the compositions of the invention, scoring a surface of juvenile cartilage or neocartilage; separating at least a portion of the scored cartilage from underlying bone; and adding a preservative to the separated cartilage.

Another aspect of the invention includes a kit for repairing cartilage including any of the compositions of the invention, a pouch having a hollow interior; a sterile container positioned in the hollow interior having a receptacle therein; and one or more particles of juvenile cartilage and/or neocartilage positioned in the receptacle of the container.

These and other features, aspects, and advantages of the present invention will become better understood with regard to the following description, appended claims and accompanying figures where:

BRIEF DESCRIPTION OF THE SEVERAL VIEWS OF THE DRAWINGS AND FIGURES

FIG. 1 shows an embodiment of the invention wherein cartilage particles are distributed throughout substantially all of the biocompatible chondro-conductive/inductive matrix.

FIG. 2 shows an embodiment of the invention wherein cartilage particles are distributed throughout approximately 75% or less of the biocompatible chondro-conductive/inductive matrix.

FIG. 3 shows an embodiment of the invention wherein cartilage particles are distributed throughout substantially all of the biocompatible chondro-conductive/inductive matrix and further comprises a particulate osteo-conductive matrix.

DETAILED DESCRIPTION OF THE INVENTION

Figure 4:
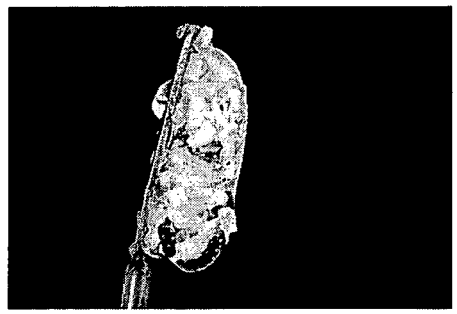
FIG. 4 shows juvenile cartilage particles encapsulated within a hyaluronate hydrogel.

The term "juvenile cartilage" refers to a chondrocyte cell, cells, cartilage tissue, or progeny or derivatives thereof, that are committed to become cartilage, or progenitor cells which are capable of undergoing proliferation growth, differentiation and maturation into chondrocytes and formation of cartilaginous tissue. In general, such chondrocytes are most readily found in tissue from individuals who encompass allograft, autograft and xenograft sources. In humans, preferably chondrocytes are from those less than fifteen years of age, and more preferably, less than two years of age. Typically, immature or juvenile chondrocytes express an enhanced ability to synthesize and organize a hyaline cartilage extra-cellular matrix. This activity usually is highest in cells freshly isolated from donor tissue and decays during subsequent manipulation such as passage and expansion.

The term "neocartilage" refers to cartilage characterized by one or more of the following attributes: containing membrane phospholipids enriched in Mead acid, containing membrane phospholipids depleted in linoleic or arachidonic acid, being substantially free of endothelial, bone and/or synovial cells, having a sulfated glycosaminoglycan S-GAG content of at least 400 mg/mg, positive for type II collagen expression, being substantially free of type I, III and X collagen, containing a matrix substantially free of biglycan, having multiple layers of cells randomly arranged, rather than separated into distinct zones of chondrocyte maturation, being enriched in high molecular weight aggrecan, being produced in vitro and essentially free of non-cartilage material, or being characterized by having multiple layers of cells surrounded by a substantially continuous insoluble glycosaminoglycan and collagen-enriched hyaline extracellular matrix.

The term "biocompatible" refers to materials which, when incorporated into the invention, have acceptable toxicity, acceptable foreign body reactions in the living body, and acceptable affinity with living tissues.

The term "chondro-inductive" refers to the ability of a material to induce the proliferation, growth differentiation and/or other maturation of chondrocytes or chondroprogenitor cells and/or proliferation, growth differentiation and/or maturation of chondrocytes or chondroprogenitor cells or production of articular cartilage from neocartilage progenitor cells, chondrocytes or cartilage. A chondro-inductive material may act directly as a growth factor which interacts with precursor cells to induce chondrocyte proliferation, growth differentiation and/or maturation, or the material may act indirectly by inducing the production of other chondro-inductive factors, such as growth factors. This induction may optionally include without limitation signaling, modulating, and transforming molecules.

The term "chondro-conductive" refers to materials which provide an environment for proliferation, differentiation, growth, ingrowth and/or orientation of cartilage tissue, chondrocyte cells or chondroprogenitor cells from surrounding tissues.

The term "chondro-inductive/conductive" refers to the characteristic of being both chondro-inductive and chondro-conductive.

The term "matrix" refers to substance(s) which adhered to or partially embedded within which something is contained.

The term "osteo-conductive" refers to materials which provide an environment for proliferation, differentiation, growth, ingrowth and/or orientation of osteogenic cells.

The term "flap" refers to an autologous or allogenic membrane of live cells, natural or synthetic material that can be vital or devitalized. The flap contains the matrix with cartilage particles that can be attached to natural cartilage or underlying bone in vivo by sutures or sutureless attachment such as chemical tissue welding or gluing, or by physical attachment devices such as tacks or staples.

The compositions and methods as described herein comprise useful repair of damaged or diseased articular cartilage. The compositions and methods include a cartilage matrix or particles and a biocompatible chondro-conductive/inductive matrix.

In another aspect of the invention a device as described herein may be disposed into a site of cartilage repair, regeneration or augmentation.

In another aspect of the invention, the compositions further comprise a particulate osteo-conductive matrix.

In other embodiments the cartilage matrix comprises a cartilage growth-enhancing material selected from the group consisting of at least one juvenile cartilage particle, at least one neocartilage particle, a combination thereof, and any of the above together with an associated matrix.

The compositions may be used according to the methods of the invention, for implanting or transplanting or otherwise disposing a reparative construct into a site in need of articular cartilage repair, regeneration or growth.

In another aspect of the invention a device may be formed from the inventive compositions and the device may be disposed in a site in need of articular cartilage repair.

In some embodiments the compositions further comprise a particulate osteo-conductive matrix.

The biocompatible chondro-conductive/inductive matrix of the invention comprises any appropriate compound or combination of compounds that is inductive or conductive for the formation or repair of articular cartilage in the inventive compositions and methods.

The chondro-conductive/inductive matrix may comprise fibrinogen. The fibrinogen may be from any suitable source. For example, one skilled in the art will recognize that fibrinogen may be derived from blood bank products—either heterologous (pooled or single-donor) or autologous cryoprecipitate or fresh frozen plasma. Fibrinogen can also be derived from autologous fresh or platelet-rich plasma, obtained using cell-saver or other techniques. U.S. Pat. No. 5,834,420 also discloses a method for obtaining fibrinogen.

In other embodiments the biocompatible chondro-conductive/inductive matrix comprises thrombin. The thrombin may be from any suitable source. One skilled in the art will recognize that thrombin can be isolated by well known means or purchased commercially. See U.S. Pat. No. 4,965,203, and Berliner, J L, Thrombin: Structure and Function (Ed) Plenum Pub Corp; (1992) for exemplary methods of isolation and/or purification.

In any embodiment the biocompatible chondro-conductive/inductive matrix may comprise a combination of fibrinogen and thrombin. The chondro-conductive/inductive matrix may contain equal proportions of fibrinogen and thrombin or more of either fibrinogen than thrombin or more thrombin than fibrinogen. When used in combination the two may be in any proportion, ranging from one part of either compared to the amount of the other up to equal proportions of each of the two.

Regardless of whether the fibrinogen or the thrombin are mixed with the neocartilage, juvenile cartilage or are separate components of the biocompatible chondro-conductive/inductive matrix, when practicing certain embodiments of the invention the fibrinogen and thrombin components preferably are kept separate from each other prior to the time of use. The fibrinogen and the thrombin are then brought into contact with each other at the time of use. A common type of applicator that may be used for this purpose consists of a double syringe, joined by a Y-connector where the components mix as they emerge. This type of applicator, used with a blunt cannula, is useful for combining the thrombin and the fibrinogen and also useful in the methods of the invention for disposing or transplanting the inventive compositions to a site wherein articular cartilage repair is desired. In cases where the articular cartilage repair site is open for repair, the fibrinogen and/or thrombin can also be used with a spray attachment to cover surfaces; or the fibrinogen and/or thrombin may be applied to an absorbable carrier or dressing, such as a cellulose sponge, collagen fleece, vital or devitalized periosteum or any other suitable means.

In various embodiments the chondro-conductive/inductive matrix may comprise one or more of fibrinogen, thrombin, fibrinogen/thrombin (Tisseel or Crosseal), albumin, in-situ forming poly (ethylene glycol) (PEG) hydrogel, fibrin, hyaluronate, fibrin/hyaluronate, collagen hyaluronate, fibrin/collagen/hyaluronate, PEG/hyaluronate, PEG/collagen, PEG base sealants (CoSeal), or other plasma and protein-based adhesives and/or sealants, other natural adhesives and/or sealants and combinations thereof, that are biocompatible with regard to the articular cartilage repair or replacement and are inductive or conductive for the cartilage matrix or cartilage growth-enhancing material in the repair or replacement of articular cartilage.

The biocompatible chondro-conductive/inductive matrix, may in some embodiments optionally function to facilitate anchoring and/or fixation of the composition in the methods of the invention to repair the desired articular cartilage.

The invented compositions may also include materials which are not yet known, but which provide characteristics relating to these components which are similar to the materials described herein.

The cartilage tissue in certain embodiment of the inventive composition also may comprise neocartilage or juvenile cartilage or a combination of neocartilage or juvenile cartilage. The neocartilage and juvenile cartilage may be in any proportion to each other, ranging from one cell or part of either compared to the other up to equal proportions of each of the two. For example, the cartilage matrix or cartilage growth-enhancing material may contain equal proportions of neocartilage and juvenile cartilage or more of either neocartilage than juvenile cartilage or more juvenile cartilage than neocartilage. In some embodiments the compositions of the invention further comprise a particulate osteo-conductive matrix. The neocartilage or juvenile cartilage is in the form of particles in the cartilage matrix or cartilage growth-enhancing material. The particles increase the surface to volume ratio in the cartilage matrix or cartilage growth-enhancing material, which allows for improved integration and metabolite and growth factor exchange, which advantageously results in enhanced viability and shelf life for the compositions. The neocartilage and juvenile cartilage particles may vary in size ranges from 1 to 27 mm 3. Thus, the neocartilage and juvenile cartilage particles placed in cartilage matrix or cartilage growth-enhancing material also may vary in size from single cells with associated matrix to 100 mm 3 in size depending on application or defect type. For a somewhat typical defect of 2 cm, at least $1 \times 10\ 6$ to $2 \times 10^6$ cells would be disposed, preferably $2 \times 10\ 6$ to $4 \times 10\ 6$, and most preferably $10 \times 10\ 6$ to $20 \times 10\ 6$. The amount of cells used may vary depending on the specific circumstances of a defect in need of repair and the goals of the patient. For example, one skilled in the art would recognize that on average, adult tissue has about a 5 to 10% cell mass per gram of tissue. This equates to about a 7% fill. However, some cell death will likely occur during maturation so a higher initial cell count is typically preferable.

In terms of providing economic ratios of tissue to percentage fill of defects, to maximize tissue use, approximately 300 mg of tissue would provide for about a 50% defect fill, although less, approximately 200 mg, for a 30% defect fill, and most preferably, for a 10% defect fill, 60 mg would be utilized.

The matrix portion of the cartilage matrix or cartilage growth-enhancing material may comprise thrombin, fibrinogen, media or fibrinogen in combination with media or thrombin in combination with media. Any suitable media may be used for the media component. Examples of suitable media include, but are not limited to a conditioned growth medium adapted for use in growing cartilage cell cultures which contains heparin-binding growth factors, at least one of which is a cartilage-derived morphogenetic protein (Chang et al., J. Biol Chem 269: 28227-28234), other pre-conditioned medias, Dulbecco's modified Eagle's medium (DMEM), Minimum Essential Medium and RPMI (Roswell Park Memorial Institute) medium. The culture medium may also comprise ascorbate, and/or exogenous autocrine growth factors.

The juvenile cartilage in the invention may be from any suitable source. The juvenile cartilage or chondrocytes used in the composition may be harvested from donor tissue and prepared by dividing or mincing the donor cartilage into small pieces or particles. The juvenile cartilage particles may comprise juvenile cells or tissue, which may be intact, minced or disrupted, such as by homogenizing the tissue. Examples of sources of donor cartilage include autologous, allogenic or xenogenic sources. In the case of autologous grafts, cartilage is harvested from cartilaginous tissue of the patient's own body. Typical sources for autologous donor cartilage include the articular joint surfaces, intercostals cartilage, and cartilage from the ear or nasal septum. In the case of allografts, the cartilage may be taken from any appropriate non-identical donor, for example from a cadaveric source, other individuals or a transgenic source or similar appropriate source.

In any embodiment of the invention the cartilage matrix or cartilage growth-enhancing material may comprise juvenile cartilage (without neocartilage) in any suitable tissue culture media. The juvenile cartilage may also comprise juvenile cartilage tissue in a matrix of thrombin or juvenile cartilage in a matrix of fibrinogen.

In any embodiment that includes neocartilage, the cartilage matrix or cartilage growth-enhancing material may comprise neocartilage cells in any suitable tissue culture media. The neocartilage matrix or cartilage growth-enhancing material may also comprise neocartilage in a thrombin matrix or neocartilage in a fibrinogen matrix.

In embodiments having neocartilage, the neocartilage may be from any suitable source. The neocartilage particles may comprise neocartilage cells or tissue, which may be intact, minced or disrupted, such as by homogenizing the tissue. The neocartilage may be either autologous or allogenic. Examples of suitable sources include commercially available sources, such as Carticel® (Genzyme Biosurgery, Cambridge, Mass.), embryonic sources, tissue culture sources or any other suitable source. For example a cell culture may be produced to grow neocartilage by isolating immature chondrocytes, e.g., fetal, neonatal, and pre-adolescent chondrocytes from donor articular cartilage. The neocartilage of the inventive cartilage matrix or cartilage growth-enhancing material may be obtained by culturing chondrocytes under suitable culture conditions known in the art, such as growing the cell culture at 37 degrees C. in a humidified atmosphere with the addition of 2-10% carbon dioxide, preferably 5%. Chondrocytes may be isolated by methods known in the art such as by sequential enzyme digestion techniques. The isolated chondrocytes may then be seeded directly on a tissue culture vessel in any suitable media. Also see, for examples of other sources, U.S. Pat. No. 5,326,357 which describes methods to produce a continuous cartilaginous tissue and U.S. Pat. No. 6,235,316 which discloses neocartilage compositions and uses, which are incorporated by reference, herein in their entirety.

The juvenile or neo cartilage tissue for the cartilage matrix or cartilage growth-enhancing material can be mammalian or avian replacement tissue, most preferably from the same species as the recipient, for example human donor tissue for human replacement and equine tissue for equine use. Furthermore, mammalian replacement tissue can be produced using chondrocytes from transgenic animals which may have been genetically engineered to prevent immune-mediated xenograft rejection.

In embodiments where the matrix portion of the cartilage matrix or cartilage growth-enhancing material comprises tissue culture media, without fibrinogen or thrombin, then the biocompatible chondro-conductive/inductive matrix preferably comprises fibrinogen and thrombin.

In embodiments where the matrix portion of the cartilage matrix or cartilage growth-enhancing material comprises media and fibrinogen, then the biocompatible chondro-conductive/inductive matrix preferably comprises thrombin.

In embodiments where the matrix portion of the cartilage matrix or cartilage growth-enhancing material comprises media and thrombin, then the biocompatible chondro-conductive/inductive matrix preferably comprises fibrinogen.

In different embodiments various combinations of the cartilage matrix or cartilage growth-enhancing material and the biocompatible chondro-conductive/inductive matrix are possible. By way of non-limiting example, an embodied composition may comprise juvenile cartilage and thrombin in the cartilage matrix with the biocompatible chondro-conductive/inductive matrix comprising media and fibrinogen.

In another embodiment the cartilage matrix or cartilage growth-enhancing material may comprise neocartilage and thrombin with the biocompatible chondro-conductive/inductive matrix comprising media and fibrinogen.

In another embodiment the cartilage matrix or cartilage growth-enhancing material may comprise a combination of juvenile and neocartilage in thrombin with the biocompatible chondro-conductive/inductive matrix comprising media and fibrinogen.

In any embodiment the compositions may further comprise an osteo-conductive matrix. The osteo-conductive matrix comprises bone particles. The bone particles may be from any suitable source. The osteo-conductive matrix may include but not be limited to fibrinogen/thrombin (Tisseel, Crosseal), fibrin/tri-calcium phosphate, fibrin/collagen/tri-calcium phosphate, fibrin/hyaluronate/tri-calcium phosphate PEG base sealants (CoSeal), PEG/tri-calcium phosphate, PEG/collagen (FibroGen) and any of the above components mixed with demineralized bone matrix. The osteo-conductive matrix may be purchased from commercial sources, such as the demineralized bone matrix compositions Grafton® (Osteotech, Eatontown, N.J.). Examples of other sources suitable for the osteo-conductive matrix include those disclosed in U.S. Pat. No. 5,356,629, U.S. Pat. No. 6,437,018 and U.S. Pat. No. 6,327,257. Suitable compositions may comprise demineralized bone, demineralized bone matrix, nondecalcified bone, cancellous bone or combinations of the same and a gel material. The osteo-conductive matrix may also comprise a porous solid, semisolid, paste or gel material including materials such as gelatin, hyaluronic acid, collagen, amylopectin, demineralized bone matrix, and/or calcium carbonate fibrinogen/thrombin, fibrin/tri-calcium phosphate, fibrin/collagen/tri-calcium phosphate, fibrin/hyaluronate/tri-calcium phosphate, in-situ forming PEG hydrogel sealants in-situ forming PEG hydrogel sealants, PEG/tri-calcium phosphate, PEG/collagen, demineralized bone matrix, and any combination thereof.

Osteoconductive materials are generally porous materials and are able to provide latticework structures such as the structure of cancellous bone or similar to cancellous bone. Such materials may generally facilitate blood-vessel incursion and new bone formation into a defined passive trellis-like support structure, as well as potentially supporting the attachment of new osteoblasts and osteoprogenitor cells. Osteoconductive materials may provide an interconnected structure through which new cells can migrate and new vessels can form.

Examples of materials suitable for the osteoconductive matrix include those disclosed in U.S. Pat. No. 5,356,629 which discloses a composition of polymethylacrylate biocompatible particles dispersed in a matrix of cellulose ether, collagen or hyaluronic acid and U.S. Pat. No. 6,437,018 which includes a composition of demineralized bone matrix (DBM) in an aqueous carrier that is sodium hyaluronate in a phosphate buffered aqueous solution. U.S. Pat. No. 6,327,257 discloses compositions with demineralized bone, nondecalcified bone, cancellous bone and a gel material. There are also compositions that are available commercially, including demineralized bone matrix compositions such as Grafton® (Osteotech, Eatontown, N.J.). These compositions typically comprise a porous solid, semisolid, paste or gel material including materials such as gelatin, hyaluronic acid, collagen, amylopectin, demineralized bone matrix, and/or calcium carbonate, to create an osteoconductive environment.

In some embodiments the composition optionally further comprises other components or compounds to address the needs of a particular articular cartilage injury or circumstance or a specific patient's individual needs. By way of non-limiting example the biocompatible chondro-conductive/inductive matrix may in some instances comprise albumin, in-situ forming PEG hydrogel, fibrin/hyaluronate, fibrin/collagen/ hyaluronate, PEG/hyaluronate, PEG/collagen, other plasma and protein-based adhesives and sealants, other natural adhesives and sealants and any combination of these.

In any embodiment the cartilage matrix may be distributed throughout substantially all of the biocompatible chondro-conductive/inductive matrix, as shown in FIG. 1. Alternatively the cartilage matrix may be distributed throughout a portion of the biocompatible chondro-conductive/inductive matrix, as shown in FIG. 2. The cartilage matrix may be distributed throughout 90% or less of the biocompatible chondro-conductive/inductive matrix. The cartilage matrix may also be distributed throughout 80% or less of the biocompatible chondro-conductive/inductive matrix. The cartilage matrix may also be distributed throughout 70% or less of the biocompatible chondro-conductive/inductive matrix. The cartilage matrix may also be distributed throughout 60% or less of the biocompatible chondro-conductive/inductive matrix. The cartilage matrix may also be distributed throughout 50% or less of the biocompatible chondro-conductive/inductive matrix. The cartilage matrix may also be distributed throughout 40% or less of the biocompatible chondro-conductive/inductive matrix. The cartilage matrix may also be distributed throughout 30% or less of the biocompatible chondro-conductive/inductive matrix. The cartilage matrix may also be distributed throughout 20% or less of the biocompatible chondro-conductive/inductive matrix. The cartilage matrix may also be distributed throughout 10% or less of the biocompatible chondro-conductive/inductive matrix.

Similarly, in embodiments where the compositions and methods further comprise an osteo-conductive matrix, the osteo-conductive matrix may be distributed throughout substantially all of the composition. Alternatively the osteo-conductive matrix may be distributed throughout a portion of the composition. It may be desirable in some embodiments to have the osteo-conductive matrix disposed to contact bone in a defect that has involvement of both bone and articular cartilage, as shown in FIG. 3. The osteo-conductive matrix may be distributed throughout 90% or less of the composition. The osteo-conductive matrix may also be distributed throughout 80% or less of the composition. The osteo-conductive matrix may also be distributed throughout 70% or less of the composition. The osteo-conductive matrix may also be distributed throughout 60% or less of the composition. The osteo-conductive matrix may also be distributed throughout 50% or less of the composition. The osteo-conductive matrix may also be distributed throughout 40% or less of the composition. The osteo-conductive matrix may also be distributed throughout 30% or less of the composition. The osteo-conductive matrix may also be distributed throughout 20% or less of the composition. The osteo-conductive matrix may also be distributed throughout 10% or less of the composition.

In one embodiment a method of use comprises disposing a cartilage matrix of neocartilage or juvenile cartilage, or a combination thereof and a biocompatible chondro-conductive/inductive matrix in any location where repair or replacement of articular cartilage is desired.

In one embodiment a method of use comprises disposing a cartilage matrix of neocartilage or juvenile cartilage, or a combination thereof and a biocompatible chondro-conductive/inductive matrix and an osteo conductive matrix in any location where repair or replacement of articular cartilage is desired. Compositions and methods of the invention comprising the osteo conductive matrix are useful for repair of replacement of articular cartilage at a site that also includes a bone defect.

In other embodiments a method of use comprises disposing any embodiment of the compositions of the invention into a defect and overlaying the composition with a retainer. The retainer may be of any suitable size and material that functions to maintain the particle in the site where the particle(s) is disposed. The retainer may be for example a flap, plug, disc, sheet or patch. In one embodiment the retainer comprises a flap. The flap is made up of either live cells, such as periosteum cells, other natural tissue membrane or synthetic membrane. The periosteal flap may be vital or devitalized and may be an autologous or an allograft.

Any of the embodiments of the inventive compositions may be used in any of the embodiments of the methods of the invention. The compositions may be extruded or otherwise disposed into the targeted site or configured into a device for transplanting into a desired site (FIG. 1). Typically a multi-unit dispensing device such as a double or triple syringe, joined by a Y-connector, or similar converging connector from the dispensing unit may be used where the components mix as they emerge from a blunt cannula or catheter or other similar device. Any embodiment of the compositions may be delivered to the defect site through an arthroscopic portal from a mixing mechanism that automatically meters the components in the correct ratio, into the desired site for articular cartilage repair or replacement.

Delivery of the compositions may be in a variety of forms and combinations; by way of non-limiting example the cartilage matrix may be in media and mixed with biocompatible chondro-conductive/inductive matrix comprising fibrinogen and thrombin just prior to use as a 3 part mixture. Alternatively, the cartilage matrix may include thrombin and be combined with a fibrinogen biocompatible chondro-conductive/inductive matrix at the time of use, as a 2 part mixture. In another alternative, the cartilage matrix may include fibrinogen and be combined with a biocompatible chondro-conductive/inductive matrix comprising thrombin at the time of use, as a 2 part mixture.) By changing the particles included in the matrix, for example the juvenile cartilage pieces, in vitro-grown neocartilage and the components that comprise the chondro-inductive matrix and/or the osteo-conductive matrix, the nature of the repair graft can be varied from partial thickness through full thickness into osteochondral defects, as desired and/or in response the to the specific site where repair or replacement is desired. Another alternative for delivery is that various combinations of the cartilage matrix and the biocompatible chondro-conductive/inductive matrix may be preformed and implanted as a single construct. By way of non-limiting example, an embodied composition may comprise juvenile cartilage pre-cast in a biocompatible chondro-conductive/inductive matrix comprising fibrin.

The juvenile neocartilage replacement tissue or pre-cast construct made up of the juvenile cartilage, a chondro conductive/inductive matrix and/or an osteoconductive matrix can also be attached to natural cartilage or underlying bone in vivo by sutures or sutureless attachment such as chemical tissue welding or gluing, or by physical attachment devices such as tacks or staples. The neocartilage may be grown to various size specifications to facilitate implantation.

Any of the compositions may be configured to form a device of the present invention and the device may then be implanted, inserted or otherwise suitably disposed in a site where repair or replacement of articular cartilage is desired. For example any embodiment of the compositions may be extruded or delivered into a form or mold to produce a specific shape or configuration of device and the produced device may then be appropriately implanted or otherwise disposed in the site where replacement or repair of articular cartilage is desired.

Figure 8:
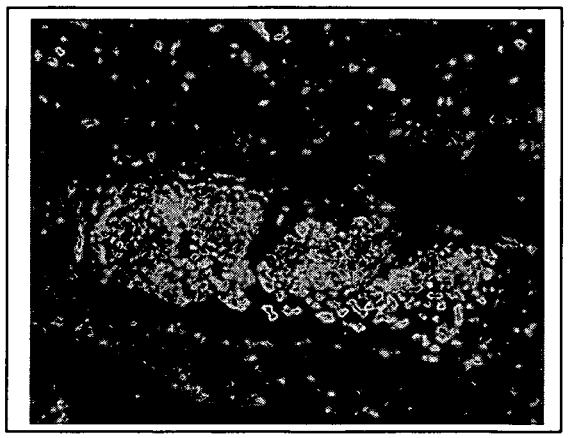
FIG. 8 shows viable human juvenile cartilage implanted into a goat femoral condyle 6 weeks after surgery.

In all cases, the compositions and devices of the invention will have a period of plasticity during which they can be implanted and/or molded to the defect being repaired. These methods of delivery advantageously make implantation of the repair articular cartilage possible in a single arthroscopic procedure, if desired. Once implanted, the cartilage fragments coalesce and replace the matrix with hyaline cartilage tissue. This method can also be extended to neocartilage grown in vitro with the advantage that some expansion of chondrocytes/neocartilage can be done, generating more repair tissue from a single donation of juvenile cartilage. Juvenile chondrocytes and/or juvenile cartilage/neocartilage can be combined with the biocompatible matrix using a uniform distribution as illustrated in FIG. 1 or a non-uniform distribution to increase the cartilage/chondrocyte density as illustrated in FIG. 2 and FIG. 8, where the cartilage is at a higher density near the bottom of the defect.

Similarly, different components can be mixed with the biocompatible matrix to fill chondral and osteochondral defects. FIG. 3 illustrates a potential usage wherein the bone defect is filled with an osteo-conductive matrix up to the tide mark, above which the chondral defect is filled with juvenile chondrocytes and/or juvenile cartilage/neocartilage matrix combined with the biocompatible matrix.

The cartilage may be harvested from cartilage donors such as juvenile animals. For example, the donors may be prepubescent humans aged between about 20 weeks and about 13 years. The cartilage may be harvested from a variety of cartilage sites, including facing surfaces of bones positioned at articulating joints. Among particularly desirable harvest sites are femoral condyles, tibial plateaus and interior surfaces of patella. To harvest the cartilage, the harvest sites are exposed. The surface of a harvest site is scored with a blade such as a #10 scalpel having a ceramic coated edge (e.g., an IonFusion scalpel blade available from IonFusion Surgical, a division of Molecular Metallurgy, Inc. of El Cajon, Calif.) Although the site may be scored in other patterns without departing from the scope of the present invention, in one embodiment the site is scored in a square grid pattern having sides measuring about one millimeter. Further, although the site may be scored to other depths without departing from the scope of the present invention, in one embodiment the site is scored to a depth of between about one millimeter and about three millimeters or more. Once the site is scored, at least a portion of the scored cartilage is separated from underlying bone, such as by shaving the scored surface with the aforementioned scalpel. As will be appreciated by those skilled in the art, separating the cartilage in this fashion results in small generally cube-shaped particles of cartilage having sides of about one millimeter. Tissue other than cartilage, such as vascularized bone and tendons, generally should be avoided when separating the cartilage from the bone.

The separated particles are collected in a container such as a conical tube. The particles may be stored in or rinsed with a saline solution such as a 0.9% saline solution. After rinsing or storage, the saline solution may be removed from the particles by aspiration and another preservative may be added to the particles. For example, a storage solution comprising hydroxyethyl starch (50 g/L)m lactobionic acid (35.8 g/L), adenosine (1.34 gL), NaOH (5M) (5 mL/L), KH2PO4 (3.4 g/L), MgSO4 (0.6 g/L), glutathione (0.92 g/L), raffinose (17.8 g/L), and KOH (5M) (pH to 7.4) may be added to the particles.

A kit for repairing cartilage may be formed using the particles. Generally, the kit includes an outer bag or pouch having a hollow interior, a sterile container positioned in the hollow interior, and cartilage particles positioned in a receptacle of the container. Although the outer pouch may have other configurations without departing from the scope of the present invention, in one embodiment the pouch is formed from two sheets, each of which has a central portion surrounded by a margin. The sheets are separably joined to one another at their margins. One such pouch is available from Amcor Flexibles Healthcare of Ann Arbor, Mich., and is identified as an RLP-041 HS pouch made from a 48 ga PET/ 10 lb LDPE/2 mil peelable film (LFM-101). The pouch is about 4×6 inches and has 15 degree chevron configuration with thumb notch. In one embodiment, the container includes a tray having a teardrop-shaped central cup or receptacle and a lip or flange surrounding the receptacle. One such container is available from Prent Corporation of Janesville, Wis., and is formed from a laminate comprising a Glidex sheet sandwiched between PETG sheets having an overall thickness of about 0.020 inch. A removable cover is attached to the lip of the tray for sealing the receptacle to retain the particles in the receptacle. One such cover is available from Tolas Health Care Packaging of Feasterville, Pa., and is known as a TPC-0777A peelable lamination for sterile device packaging. Although the cover may have other dimensions without departing from the scope of the present invention, in one embodiment the cover has a thickness of about 3.95 mils and is about 1.57×3.15 inches.

In one embodiment, excess liquid is removed from the particles by aspiration and a 50 mg scoop is used to measure a desired quantity of particles into a sterile tray, a desired measure of preservative solution (e.g., 2.5 mL) is added to the tray and the cover is sealed against the rim of the tray to close the container. The container is loaded into a pouch and the pouch is sealed for storage and transport. Once ready for use, the pouch is pealed open and the container is deposited in a sterile environment. The non-sterile pouch is disposed and the container is opened by peeling back the cover to expose the particles of cartilage.

EXAMPLES

Without further elaboration, it is believed that one skilled in the art can, using the preceding description, utilize the present invention to its fullest extent. The following specific examples are offered by way of illustration only and not by way of limiting the remaining disclosure.

Example 1

Juvenile Human Articular Cartilage (JHAC) in a Hyaluronate Matrix

In certain embodiments of the composition as described herein particulate JHAC was embedded within a hyaluronate hydrogel and evaluated for their viscosity and their ability to adhere within a defect. Hyaluronate forms a viscous gel that can hold the cartilage particles within a defect during implantation. Concentrations of hyaluronate ranging from 5 mg/ml to 100 mg/ml were tested in this example. In the mixture illustrated by FIG. 4, JHAC was embedded in a gel containing 50 mg of hyaluronate dissolved in 1 ml of phosphate buffered saline. Although suitable for a matrix, hyaluronate alone lacked cross-linking within the gel. Therefore, in one preferred composition, a component such as fibrin is included to retard or prevent dissolution of the chondro-conductive matrix.

Example 2

In Vitro JHAC Re-Integration

Figure 5:
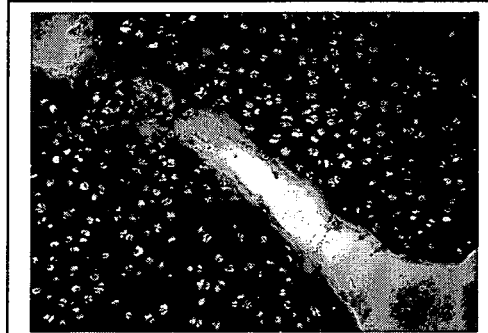
FIG. 5 shows the morphologic appearance of human juvenile cartilage particles, pre-cast in a fibrin matrix, after 60 days of laboratory culture.

When juvenile tissue is maintained in the laboratory embedded within a fibrin matrix, the tissue has the ability to re-integrate. In this experiment, JHAC was minced and cast in human fibrinogen within a cylindrical mold and then cultured for 60 days in a standard cell culture using a proprietary serum-free medium, developed at Isto Technologies, Inc. The tissue composite was then fixed and histological slides were prepared and stained with Safranin-O which stains red in the presence of sulfated glycosaminoglycan (S-GAG). Safranin-O staining is unique to the hyaline cartilage that lines the articular surfaces of the joints. As shown in FIG. 5, the two pieces of tissue have begun to integrate with each other in the fibrin-filled space between the original tissue pieces. The dark red stain (original proof) indicates that the tissue has remained viable and is maintaining a normal hyaline-cartilage phenotype with regard to S-GAG composition.

Example 3

Minced JHAC Implantation

Minced JHAC was implanted into Spanish goats using the methods of the invention, further demonstrating the usefulness of the invention. A six (6) mm circular defect was created in the weight-bearing region of the right, medial femoral condyle. Minced juvenile human articular cartilage was placed into the defect which was subsequently filled with human fibrin and covered with a live periosteal flap sutured into the surrounding cartilage. The limb was then set in a modified Thomas splint for a period of six weeks during which the animal was able to ambulate without exposing the repaired site to full weight-bearing forces.

Figure 6:
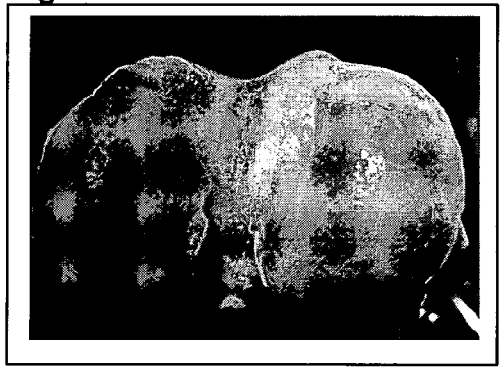
FIG. 6 shows a repaired medial femoral condyle (right side of photograph) of a Spanish goat, 6 weeks after implantation of human juvenile cartilage particles with a fibrin matrix and live periosteal flap.
Figure 7:
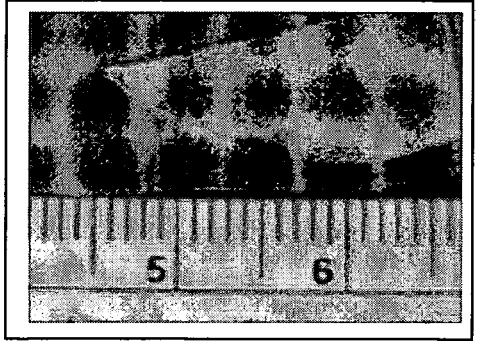
FIG. 7 shows a 1 mm thick section through the defect site represented in FIG. 6

FIG. 6 shows the repaired medial femoral condyle (right side of photograph) six weeks after implantation. The surface of the repair site appears relatively smooth and the tissue has been retained within the original defect. A 1 mm thick section through the defect site is shown in FIG. 7. The section shows that the defect is filled with a white, translucent material including the original tissue pieces. Fluorescent probes stain the nuclear DNA red and identify dead cells while green probes stain living cells within the cartilage matrix. The juvenile cartilage is embedded into a chondro-conductive matrix composed of fibrin that is less cellular. Microscopic examination of the section using a viability-indicating stain indicates that both the original tissue and cells that have migrated into the fibrin matrix stain green (original proof) and are therefore viable (FIG. 8).

Figure 9:
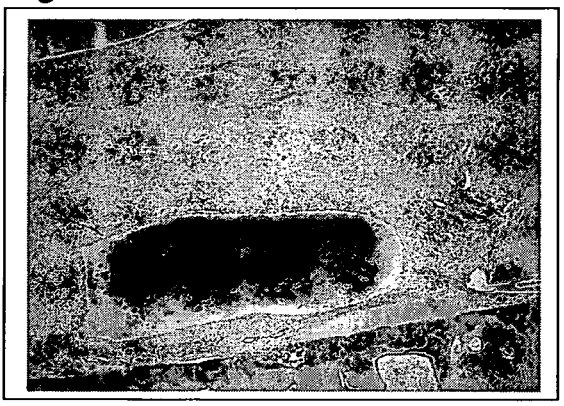
FIG. 9 shows the morphologic appearance of human juvenile cartilage particles implanted into a goat femoral condyle 6 weeks after surgery.

Safranin-O stained histological sections indicate that the defect site is populated not only by the original implanted tissue, but also by cells that have migrated into the defect site as illustrated by FIG. 9. The original tissue retains the red stain (original proof) indicating S-GAG in the extracellular matrix while the cell-populated matrix surrounding the transplanted tissue has not yet been replaced with a hyaline-like extracellular matrix. The juvenile cartilage is embedded into a chondro-conductive matrix composed of fibrin.

These data demonstrate the successful repair of a chondral defect with a viable tissue construct containing juvenile hyaline cartilage according to one embodiment of the present invention.

Other Embodiments

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions of the claims that follow and their equivalents. While some of the examples and descriptions above include some conclusions about the way the invention may function, the inventors do not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

References Cited

All publications, patents, patent applications and other references cited in this application are herein incorporated by reference in their entirety as if each individual publication, patent, patent application or other reference were specifically and individually indicated to be incorporated by reference.

What is claimed is:

1. A cartilage treatment composition comprising:
cadaveric, allogenic human juvenile cartilage tissue particles comprising viable chondrocytes; and
a matrix, wherein the matrix is defined as a chondro-conductive media;
wherein the chondro-conductive media is a media comprising one or more growth factors.

2. The composition of claim 1, wherein the chondro-conductive media is a media suitable for tissue or cell culture.

3. The composition of claim 2, wherein the chondro-conductive media is at least one of conditioned media, Dulbecco's Modified Eagle's Medium, Minimal Essential Medium, RPMI medium, media having one or more growth factors, media having ascorbate, media having fibrinogen, or media having thrombin.

4. The composition of claim 3, wherein the chondro-conductive media is at least one of Dulbecco's Modified Eagle's Medium, Minimal Essential Medium or RPMI medium.

5. The composition of claim 2, wherein the chondro-conductive media is a media having ascorbate.

6. The composition of claim 1, wherein the juvenile cartilage particles are from cadaveric juvenile donors less than fifteen years of age.

7. The composition of claim 6, wherein the juvenile cartilage particles are from cadaveric juvenile donors less than two years of age.

8. The composition of claim 6, wherein the juvenile cartilage particles are from cadaveric juvenile donors from about 20 weeks to about 13 years of age.

9. The composition of any one of claims 1, 2 or 8, wherein the juvenile cartilage particles have a dimension from about one to about three millimeters.

10. The composition of any one of claims 1, 2 or 8, wherein the juvenile cartilage particles range in size from about 1 to about 27 mm$^3$.

11. The composition of any one of claims 1, 2 or 8, wherein the juvenile cartilage particles comprise at least $1 \times 10^6$ chondrocytes.

12. The composition of any one of claims 1, 2 or 8, comprising at least 60 mg of juvenile cartilage particles.

13. The composition of any one of claims 1, 2 or 8, wherein the cartilage particles comprise articular cartilage.

14. The composition of claim 9, wherein the articular cartilage is harvested from a femoral condyle, a tibial plateau or an interior surface of a patella.

15. The composition of claim 2, wherein the chondroconductive media is a media having fibrinogen.

16. The composition of claim 2, wherein the chondroconductive media is a media having thrombin.

17. The composition of claim 2, wherein the chondroconductive media is a conditioned media.

* * * * *